United States Patent
Lidgard et al.

(10) Patent No.: US 11,299,766 B2
(45) Date of Patent: *Apr. 12, 2022

(54) MULTIPLEX AMPLIFICATION DETECTION ASSAY

(71) Applicant: Exact Sciences Corporation, Madison, WI (US)

(72) Inventors: Graham P. Lidgard, Middleton, WI (US); Hatim Allawi, Middleton, WI (US)

(73) Assignee: Exact Sciences Corporation, Madison, WI (US)

(*) Notice: Subject to any disclaimer, the term of this patent is extended or adjusted under 35 U.S.C. 154(b) by 76 days.

This patent is subject to a terminal disclaimer.

(21) Appl. No.: 16/888,375

(22) Filed: May 29, 2020

(65) Prior Publication Data
US 2020/0291458 A1 Sep. 17, 2020

Related U.S. Application Data

(63) Continuation of application No. 15/335,096, filed on Oct. 26, 2016, now Pat. No. 10,704,081.

(Continued)

(51) Int. Cl.
*C12Q 1/68* (2018.01)
*C12Q 1/6806* (2018.01)
(Continued)

(52) U.S. Cl.
CPC ....... *C12Q 1/6806* (2013.01); *C12N 15/1006* (2013.01); *C12Q 1/686* (2013.01);
(Continued)

(58) Field of Classification Search
CPC .................................................. C12Q 1/68
(Continued)

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| CN | 104781421 | 7/2015 |
| WO | WO 1992/02258 | 2/1992 |

(Continued)

OTHER PUBLICATIONS

Andersson et al., Properties of targeted preamplification in DNA and cDNA quantification. Expert Rev Mol Diagn. 2015;15(8):1085-100.

(Continued)

*Primary Examiner* — Aaron A Priest
(74) *Attorney, Agent, or Firm* — Casimir Jones, S.C.; Mary Ann D. Brow

(57) ABSTRACT

Provided herein is technology relating to the amplification-based detection of bisulfite-treated DNAs and particularly, but not exclusively, to methods and compositions for multiplex amplification of low-level sample DNA prior to further characterization of the sample DNA. The technology further provides methods for isolating DNA from blood or blood product samples, e.g., plasma samples.

20 Claims, 37 Drawing Sheets

Specification includes a Sequence Listing.

Related U.S. Application Data

(60) Provisional application No. 62/249,097, filed on Oct. 30, 2015.

(51) Int. Cl.
  *C12Q 1/686* (2018.01)
  *C12N 15/10* (2006.01)
  *C12Q 1/6837* (2018.01)

(52) U.S. Cl.
  CPC ..... *C12Q 1/6837* (2013.01); *C12Q 2600/154* (2013.01); *C12Q 2600/166* (2013.01)

(58) Field of Classification Search
  USPC .......................................................... 435/6.12
  See application file for complete search history.

(56) References Cited

U.S. PATENT DOCUMENTS

| | | | |
|---|---|---|---|
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,786,146 A | 7/1998 | Herman et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,251,594 B1 | 6/2001 | Gonzalgo et al. |
| 6,329,178 B1 | 12/2001 | Patel et al. |
| 6,395,524 B2 | 5/2002 | Loeb et al. |
| 6,602,695 B2 | 8/2003 | Patel et al. |
| 6,605,451 B1 | 8/2003 | Marmaro et al. |
| 6,872,816 B1 | 3/2005 | Hall et al. |
| 7,037,650 B2 | 5/2006 | Gonzalgo et al. |
| 7,087,414 B2 | 8/2006 | Gerdes et al. |
| 7,662,594 B2 | 2/2010 | Kong et al. |
| 8,304,214 B2 | 11/2012 | Gerdes et al. |
| 8,361,720 B2 | 1/2013 | Oldham-Haltom et al. |
| 8,715,937 B2 | 5/2014 | Zou et al. |
| 8,808,990 B2 | 8/2014 | Lidgard et al. |
| 8,916,344 B2 | 12/2014 | Zou et al. |
| 9,000,146 B2 | 4/2015 | Bruinsma et al. |
| 9,096,893 B2 | 8/2015 | Allawi et al. |
| 9,163,278 B2 | 10/2015 | Bruinsma et al. |
| 9,169,511 B2 | 10/2015 | Bruinsma et al. |
| 9,212,392 B2 | 12/2015 | Allawi et al. |
| 9,315,853 B2 | 4/2016 | Domanico et al. |
| 9,428,746 B2 | 8/2016 | Holmberg et al. |
| 9,657,330 B2 | 5/2017 | Lidgard et al. |
| 10,011,878 B2 | 7/2018 | Ahlquist et al. |
| 10,385,406 B2 | 8/2019 | Allawi et al. |
| 10,704,081 B2 | 7/2020 | Lidgard et al. |
| 10,822,638 B2 | 11/2020 | Allawi et al. |
| 2003/0224040 A1 | 12/2003 | Baylin et al. |
| 2003/0224437 A1* | 12/2003 | Gerdes .................. C12Q 1/686 435/6.12 |
| 2004/0175733 A1 | 9/2004 | Andersen et al. |
| 2004/0234960 A1 | 11/2004 | Olek et al. |
| 2005/0048527 A1 | 3/2005 | Allawi et al. |
| 2005/0214926 A1 | 9/2005 | Zielenski et al. |
| 2005/0239101 A1 | 10/2005 | Sukumar et al. |
| 2006/0134663 A1 | 6/2006 | Harkin et al. |
| 2006/0147955 A1 | 7/2006 | Allawi et al. |
| 2006/0171952 A1 | 8/2006 | Mather et al. |
| 2007/0048748 A1 | 3/2007 | Williams et al. |
| 2007/0161062 A1 | 7/2007 | Tacke et al. |
| 2007/0202525 A1 | 8/2007 | Quake et al. |
| 2009/0203011 A1 | 8/2009 | Liebenberg et al. |
| 2009/0253142 A1 | 10/2009 | Allawi et al. |
| 2011/0009277 A1 | 1/2011 | Devos et al. |
| 2011/0123990 A1 | 5/2011 | Baker et al. |
| 2011/0160446 A1 | 6/2011 | Ritt et al. |
| 2011/0287424 A1* | 11/2011 | Chen .................. C12Q 1/6851 435/6.11 |
| 2011/0318738 A1 | 12/2011 | Jones et al. |
| 2012/0122105 A1* | 5/2012 | Oldham-Haltom .......... C12Q 1/6818 435/6.12 |
| 2012/0288868 A1 | 11/2012 | Bruinsma et al. |
| 2014/0087382 A1 | 3/2014 | Allawi et al. |
| 2016/0010081 A1 | 1/2016 | Allawi et al. |
| 2016/0090634 A1 | 3/2016 | Kisiel et al. |
| 2016/0168643 A1 | 6/2016 | Ahlquist et al. |
| 2016/0194721 A1 | 7/2016 | Allawi et al. |
| 2016/0312299 A1 | 10/2016 | Tyler et al. |
| 2017/0121704 A1 | 5/2017 | Allawi et al. |
| 2017/0121757 A1 | 5/2017 | Lidgard et al. |
| 2017/0335401 A1 | 11/2017 | Allawi et al. |
| 2018/0143198 A1 | 5/2018 | Wen et al. |
| 2018/0245157 A1 | 8/2018 | Allawi et al. |
| 2019/0177769 A1 | 6/2019 | Allawi et al. |
| 2019/0330702 A1 | 10/2019 | Allawi et al. |

FOREIGN PATENT DOCUMENTS

| | | |
|---|---|---|
| WO | WO 1993/10820 | 6/1993 |
| WO | WO 1994/22892 | 10/1994 |
| WO | WO 1994/24144 | 10/1994 |
| WO | WO 1995/000669 | 1/1995 |
| WO | WO 1995/015373 | 6/1995 |
| WO | WO 1997/046705 | 12/1997 |
| WO | WO 1999/028498 | 6/1998 |
| WO | WO 2001/94634 | 12/2001 |
| WO | WO 2002/070755 | 9/2002 |
| WO | WO 2005/023091 | 3/2005 |
| WO | WO 2005/098050 | 3/2005 |
| WO | WO 2005/038041 | 4/2005 |
| WO | WO 2006/113770 | 10/2006 |
| WO | WO 2008/084219 | 7/2008 |
| WO | WO 2008/100913 | 8/2008 |
| WO | WO 2012/155072 | 11/2012 |
| WO | WO 2014/039556 | 3/2014 |
| WO | WO 2014/160117 | 10/2014 |
| WO | WO 2015/066695 | 5/2015 |
| WO | WO 2017/075061 | 5/2017 |
| WO | WO 2017/192221 | 11/2017 |
| WO | WO 2017/223216 | 12/2017 |
| WO | WO 2020/112869 | 7/2020 |

OTHER PUBLICATIONS

Arneson et al., GenomePlex Whole-Genome Amplification. Cold Spring Harb. Protoc. 2008; doi:10.1101/pdb.prot4920, 7 pages.

(56) References Cited

OTHER PUBLICATIONS

Ballabio, et al., Screening for steroid sulfatase (STS) gene deletions by multiplex DNA amplification, Human Genetics, 1990, 84(6): 571-573.
Barnay, Genetic disease detection and DNA amplification using cloned thermostable ligase, Proc. Natl. Acad. Sci USA, 1991, 88:189-93.
Bustin, Absolute quantification of mRNA using real-time reverse transcription polymerase chain reaction assays, J. Molecular Endocrinology, 2000, 25:169-193.
Chamberlain et al., Deletion screening of the Duchenne muscular dystrophy locus via multiplex DNA amplification, Nucleic Acids Research, 1988, 16(23):11141-11156.
Don et al., 'Touchdown' PCR to circumvent spurious priming during gene amplification, Nucleic Acids Research, 1991, 19(14):4008.
Fasman, "Practical Handbook of Biochemistry and Molecular Biology", pp. 385-394, 1989, CRC Press, Boca Raton, FL.
Grunau et al., Bisulfite genomic sequencing: systematic investigation of critical experimental parameters. Nucleic Acids Res. Jul. 1, 2001;29(13):E65-5.
Guilfoyle et al., Ligation-mediated PCR amplification of specific fragments from a class-II restriction endonuclease total digest, Nucleic Acids Research, 1997, 25:1854-1858.
Hall et al., Sensitive detection of DNA polymorphisms by the serial invasive signal amplification reaction, PNAS, 2000, 97:8272.
Hayden et al., Multiplex-Ready PCR: A new method for multiplexed SSR and SNP genotyping, BMC Genomics, 2008, 9:80.
Hecker et al., High and low annealing temperatures increase both specificity and yield in touchdown and stepdown PCR, Biotechniques, 1996, 20(3):478-485.
Henegariu et al., Multiplex PCR: critical parameters and step-by-step protocol. Biotechniques. Sep. 1997;23(3):504-11.
Herman et al., Methylation-specific PCR: a novel PCR assay for methylation status of CpG islands. Proc Natl Acad Sci USA 1996; 93: 9821-9826.
Higuchi et al., A general method of in vitro preparation and specific mutagenesis of DNA fragments: study of protein and DNA interactions, Nucleic Acids Research, 1988, 16(15):7351-7367.
Higuchi et al.,Kinetic PCR analysis: real-time monitoring of DNA amplification reactions, Biotechnology, 1993, 11:1026-1030.
Higuchi et al., Simultaneous amplification and detection of specific DNA sequences, Biotechnology, 1992, 10:413-417.
Jiang et al., Lengthening and shortening of plasma DNA in hepatocellular carcinoma patients. Proc Natl Acad Sci U S A. Mar. 1, 20157;112(11):E1317-25.
Kaiser et al., A comparison of eubacterial and archaeal structure-specific 5'-exonucleases. J Biol Chem. Jul. 23, 1999;274(30):21387-94.
Kalinina et al., Nanoliter scale PCR with TaqMan detection, Nucleic Acids Research, 1997, 25:1999-2004.
Korbie et al., Multiplex bisulfite PCR resequencing of clinical Ffpe DNA. Clin Epigenetics. Mar. 17, 2015;7:28.
Leontiou et al., Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058.
Lyamichev et al.,Polymorphism identification and quantitative detection of genomic DNA by invasive cleavage of oligonucleotide probes, Nat. Biotech., 1999, 17:292-296.
Munson et al., Recovery of bisulfite-converted genomic sequences in the methylation-sensitive QPCR. Nucleic Acids Res. 2007;35(9):2893-903.
Noutsias et al., Preamplification techniques for real-time RT-PCR analyses of endomyocardial biopsies. BMC Molecular Biology Jan. 14, 2008;9:3.
Olivier, The Invader assay for SNP genotyping, Mutat Res. Jun. 3, 2005;573(1-2):103-10.
Orpana, Fluorescence resonance energy transfer (FRET) using ssDNA binding fluorescent dye, Biomol Eng. Apr. 2004;21(2):45-50.
Roux, Using mismatched primer-template pairs in touchdown PCR, Biotechniques, 1994, 16(5):812-814.
Ruano et al., Biphasic amplification of very dilute DNA samples via 'booster' PCR. Nucleic Acids Res. Jul. 11, 1989;17(13):5407.
Schouten et al., Relative quantification of 40 nucleic acid sequences by multiplex ligation-dependent probe amplification, Nucleic Acids Research, 2002, 30(12): e57.
Selvin, Fluorescence resonance energy transfer, 1995, Methods Enzymol. 1995;246:300-34.
Stryer, Fluorescence energy transfer as a spectroscopic ruler, Annu Rev Biochem. 1978;47:819-46.
Triglia et al., A procedure for in vitro amplification of DNA segments that lie outside the boundaries of known sequences, Nucleic Acids Res., 1988, 16:8186.
Vogelstein et al., Digital PCR, PNAS, 1999, 96: 9236-41.
Zou et al., Quantification of methylated markers with a multiplex methylationspecific technology. Clin Chem 2012; 58: 375-383.
International Search Report and Written Opinion for PCT/US2016/058875, dated Apr. 21, 2017, 17 pages.
Allawi et al., Abstract 712: Detection of lung cancer by assay of novel methylated DNA markers in plasma. Proceedings: AACR Annual Meeting Apr. 1-5, 2017, Washington, DC. 3 pages.
Antequera et al., High levels of de novo methylation and altered chromatin structure at CpG islands in cell lines. Cell. Aug. 10, 1990;62(3):503-14.
Bibikova, GoldenGate? Assay for Methyltion of BeadArrayTM Technology. Jan. 1, 2009; retrieved from http://agtc.wayne.edu/pdfs/goldengate_methylation_brochure.pdf, retrieved Aug. 29, 2016, 7 pages.
Budd et al., Circulating tumor cells versus imaging-predicting overall survival in metastatic breast cancer. Clin Cancer Res. Nov. 1, 2006;12(21):6403-9.
Carvalho et al., Genome-wide DNA methylation profiling of non-small cell lung carcinomas. Epigenetics Chromatin. Jun. 22, 2012;5(1):9.
Ceska et al., Structure-specific DNA cleavage by 5' nucleases. Trends Biochem Sci. Sep. 1998;23(9):331-6.
Cohen et al., Relationship of circulating tumor cells to tumor response, progression-free survival, and overall survival in patients with metastatic colorectal cancer. J Clin Oncol. Jul. 1, 2008;26(19):3213-21.
Cristofanilli et al., Circulating tumor cells, disease progression, and survival in metastatic breast cancer. N Engl J Med. Aug. 19, 2004;351(8):781-91.
Dammann et al., The CpG island of the novel tumor suppressor gene RASSF1A is intensely methylated in primary small cell lung carcinomas. Oncogene. Jun. 14, 2001;20(27):3563-7.
Devos et al., Circulating methylated SEPT9 DNA in plasma is a biomarker for colorectal cancer. Clin Chem. Jul. 2009;55(7):1337-46.
Eads et al., CpG island hypermethylation in human colorectal tumors is not associated with DNA methyltransferase overexpression. Cancer Res. May 15, 1999;59(10):2302-6.
Feil et al., Methylation analysis on individual chromosomes: improved protocol for bisulphite genomic sequencing. Nucleic Acids Res. Feb. 25, 1994;22(4):695-6.
Frommer et al., A genomic sequencing protocol that yields a positive display of 5-methylcytosine residues in individual DNA strands. Proc Natl Acad Sci USA. Mar. 1, 1992;89(5):1827-31.
Gonzalgo et al., Identification and characterization of differentially methylated regions of genomic DNA by methylation-sensitive arbitrarily primed PCR. Cancer Res. Feb. 15, 1997;57(4):594-9.
Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.
Grafstrom et al., The characteristics of DNA methylation in an in vitro DNA synthesizing system from mouse fibroblasts. Nucleic Acids Res. Apr. 21, 1985;13(8):2827-42.
Gu et al., Genome-scale DNA methylation mapping of clinical samples at singlenucleotide resolution. Nat Methods. Feb. 2010;7(2):133-6.

(56) References Cited

OTHER PUBLICATIONS

Hayes et al., Circulating tumor cells at each follow-up time point during therapy of metastatic breast cancer patients predict progression-free and overall survival. Clin Cancer Res. Jul. 15, 2006;12(14 Pt 1):4218-24.
Heller et al., Lung cancer: from single-gene methylation to methylome profiling. Cancer Metastasis Rev. Mar. 2010;29(1):95-107.
Kneip et al., SHOX2 DNA methylation is a biomarker for the diagnosis of lung cancer in plasma. J Thorac Oncol. Oct. 2011;6(10):1632-8.
Kober et al., Methyl-CpG binding col. based identification of nine genes hypermethylated in colorectal cancer. Mol Carcinog. Nov. 2011;50(11):846-56.
Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.
Liu et al., Flap endonuclease 1: a central component of DNA metabolism. Annu Rev Biochem. 2004;73:589-615.
Lokk et al., Methylation markers of early-stage non-small cell lung cancer. PLoS One. 2012;7(6):e39813.
Martin et al., Genomic sequencing indicates a correlation between DNA hypomethylation in the 5' region of the pS2 gene and its expression in human breast cancer cell lines. Gene. May 19, 1995;157(1-2):261-4.
Maxwell® RSC ccfDNA Plasma Kit, Technical Manual, Instructions for Use of Product AS1480, Promega Corporation, Feb. 2016.
Meissner et al., Reduced representation bisulfite sequencing for comparative high-resolution DNA methylation analysis. Nucleic Acids Res. Oct. 13, 2005;33(18):5868-77.
Moreno et al., Circulating tumor cells predict survival in patients with metastatic prostate cancer. Urology. Apr. 2005;65(4):713-8.
Olek et al., A modified and improved method for bisulphite based cytosine methylation analysis. Nucleic Acids Res. Dec. 15, 1996;24(24):5064-6.
Olek et al., The pre-implantation ontogeny of the H19 methylation imprint. Nat Genet. Nov. 1997;17(3):275-6.
Pantel et al., Detection, clinical relevance and specific biological properties of disseminating tumour cells. Nat Rev Cancer. May 2008;8(5):329-40.
Ponomaryova et al., Potentialities of aberrantly methylated circulating DNA for diagnostics and post-treatment follow-up of lung cancer patients. Lung Cancer. Sep. 2013;81(3):397-403.
Rein et al., Identifying 5-methylcytosine and related modifications in DNA genomes. Nucleic Acids Res. May 15, 1998;26(10):2255-64.
Sadri et al., Rapid analysis of DNA methylation using new restriction enzyme sites created by bisulfite modification. Nucleic Acids Res. Dec. 15, 1996;24(24):5058-9.
Salomon et al., Methylation of mouse DNA in vivo: di- and tripyrimidine sequences containing 5-methylcytosine. Biochim Biophys Acta. Apr. 15, 1970;204(2):340-51.
Schmidt et al., SHOX2 DNA methylation is a biomarker for the diagnosis of lung cancer based on bronchial aspirates. BMC Cancer. Nov. 3, 2010;10:600.
Singer-Sam et al., A quantitative HpaII-PCR assay to measure methylation of DNA from a small number of cells. Nucleic Acids Res. Feb. 11, 1990;18(3):687.
Singer-Sam et al., A sensitive, quantitative assay for measurement of allele-specific transcripts differing by a single nucleotide. PCR Methods Appl. Feb. 1992;1(3):160-3.
Szabo et al., Allele-specific expression and total expression levels of imprinted genes during early mouse development: implications for imprinting mechanisms. Genes Dev. Dec. 15, 1995;9(24):3097-108.
Toyota et al., Identification of differentially methylated sequences in colorectal cancer by methylated CpG island amplification. Cancer Res. May 15, 1999;59(10):2307-12.
Wrangle et al., Functional identification of cancer-specific methylation of CDO1, HOXA9, and TAC1 for the diagnosis of lung cancer. Clin Cancer Res. Apr. 1, 2014;20(7):1856-64.
Xiong et al., COBRA: a sensitive and quantitative DNA methylation assay. Nucleic Acids Res. Jun. 15, 1997;25(12):2532-4.
Yamada et al., Fluorometric identification of 5-methylcytosine modification in DNA: combination of photosensitized oxidation and invasive cleavage. Bioconjug Chem. Jan. 2008;19(1):20-3.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zou et al., Sensitive quantification of methylated markers with a novel methylation specific technology. Abstract D-144, Clin Chem 2010;56(6)Suppl:A199.
European Supplemental Search Report for EP17792973.4, dated Jan. 3, 2020, 15 pages.
Chen et al., HOPX is methylated and exerts tumour-suppressive function through Ras-induced senescence in human lung cancer. J Pathol. Feb. 2015;235(3):397-407.
Ooki et al., Potential utility of HOP homeobox gene promoter methylation as a marker of tumor aggressiveness in gastric cancer. Oncogene. Jun. 3, 2010;29(22):3263-75.
International Search Report and Written Opinion for PCT/US2019/063401, dated Feb. 20, 2020, 12 pages.
U.S. Appl. No. 60/900,713, filed Feb. 12, 2007, in the name of Baylin et al., 188 pages.
Fackler et al., Quantitative multiplex methylation-specific PCR assay for the detection of promoter hypermethylation in multiple genes in breast cancer. Cancer Res. Jul. 1, 2004;64(13):4442-52.
Louwagie et al., Feasibility of a DNA methylation assay for noninvasive CRC screening. Clin Cancer Res. Oct. 2007;13(19 Suppl):B16.
Olkhov-Mitsel et al., Novel multiplex MethyLight protocol for detection of DNA methylation in patient tissues and bodily fluids. Sci Rep. Mar. 21, 2014;4:4432.
Schuebel et al., Comparing the DNA hypermethylome with gene mutations in human colorectal cancer. PLoS Genet. Sep. 2007;3(9):1709-23.
Straub et al., Base5, a versatile, highly integrated high-throughput methylation profiling for methylation specific PCR based marker identification applied to colorectal cancer. Clin Cancer Res. Oct. 2007; 13(19 Suppl):A61.
Swift-Scanlan et al., Two-color quantitative multiplex methylation-specific PCR. Biotechniques. Feb. 2006;40(2):210-9.
Yoo et al., Epigenetic therapy of cancer: past, present and future. Nat Rev Drug Discov. Jan. 2006;5(1):37-50.
Notice of Opposition and Statement filed in EP Pat 3434791, filed Mar. 5, 2021, 16 pages.

\* cited by examiner

FIG. 5A

SFMBT2 Target DNA    SEQ ID NO: 83
5' TGCCCTCGGCGTGGACCCAGGCCCCGGTCGCCGCCCGGAGGGCACCCGGCCTCGCTTGCTTGCT
CGCCCGCCCTTGCCCCGCGCTCCCCGGCGCTCCGCGCCCGGCCGCCCGGCCTCCGGTCCTCCG-3'

Bisulfite-converted target DNA with primer sites:

3.                                      4.
5' TGTTTTCGGCGTGGATTTAGG|TTTCG|GTCGTCGTTCGGGAGGGTA|TCGGTTTCGTTCGTTGTTCGTT
   CGTTCGTCGTTTTTGTTCG|TTCGTTTTTTCGTTCGTTGTTCG|GCGTTCGTTTTCGGTTTTTCG 3'
   SEQ ID NO: 84
        1.                                2.

PCR-Flap assay design:

Arm5-ATCGGTTTCGTT 3' SEQ ID NO: 85
                   |||||||||||||
5' GTCGTCGTTCGGGAGGGTATCGGTTTCGTTCGTTGTTCGTTTTTGTTCG 3'       SEQ ID NO: 86
   ||||||||||||||x||||||
   GTCGTCGTTCGAGAGGGTA>>           <<AAGCAAGCAAAAACAAGC
   SEQ ID NO: 8                      SEQ ID NO: 9
                                                          SEQ ID NO: 5
1. SFMBT2 Outer Forward Primer:      5' TGTTTTCGGCGTGGATTTAGG 3'
2. SFMBT2 Outer Reverse Primer:      5' CGAAAAACCGAAACGAACGC 3'
                                                          SEQ ID NO: 6
                                     SEQ ID NO: 8
3. SFMBT2 PCR/Flap assay Forward Primer:  5' GTCGTCGTTCGAGAGGGTA 3'
4. SFMBT2 PCR/Flap assay Reverse Primer:  5' CGAACAAAAACGAACGAACGAA 3'
                                     SEQ ID NO: 9
5. SFMBT2 Flap oligonucleotide:      5' CCACGGACGATCGGTTTCGTT/3C6/ 3'
                                     SEQ ID NO: 10

FIG. 5B

VAV3 Target DNA    SEQ ID NO: 87

5' GCGCGGGGACTGCGCTGCAGCCGGCTCGCGGTCGCGGCACCCGGGCGCCGGGACCCGGAGCCTAGCGC
   GGCGCCCGCGACCCGTCAGCCGCCGATCCCTGCTCCCTGCCGCGCGGGGAAAGGGCCGGCGCTGTTGGC 3'

Bisulfite-converted target DNA with primer sites:

SEQ ID NO: 88

5' GCG[CGGGGATTCGTTGTAGC]GGGCGTCGGGCGTATTCGGGCGTCGGGA[TCGGAGTCGAGTTTAGCGC
            1.                                          3.
   GGCGTTCGCGGATT[CGTTAGTCGAGTTTAGTGT]TTTTCGATTTCGCGGG[GAAAGGGTCGGCGGTTGT]TTGGC 3'
                        4.                                    2.

PCR-Flap assay design:

Arm5-CGGGCGTTCGCGGA 3' SEQ ID NO: 89
                     ||||||||||||||                              SEQ ID NO: 17
5' TCGGAGTCGAGTTTAGCGCGGCGTTCGCGGATTCGTTAGTCGAGTTTTGTT 3'
   ||||||||||||||||||| 
   TCGGAGTCGAGTTTAGCGC>>          <<AGCAATCAGCGCCAAAAACAA
   SEQ ID NO: 18                        SEQ ID NO: 19

1. VAV3 Outer Forward Primer:         5' CGGGGGATTCGTTGTAGC 3'
                                                               SEQ ID NO: 15
2. VAV3 Outer Reverse Primer:         5' CAACCGCCGACCCTTTC 3'
                                                               SEQ ID NO: 16
3. VAV3 PCR/Flap assay Forward Primer: 5' TCGGAGTCGAGTTTAGCGC 3'
   SEQ ID NO: 18
4. VAV3 PCR/Flap assay Reverse Primer: 5' AACAAAAACCGGACTAACGA 3'
   SEQ ID NO: 19
5. VAV3 Flap oligonucleotide:         5' CCACGGACGCGGTTCGCGGA/3C6/ 3'
                                                               SEQ ID NO: 20

FIG. 5C

BMP3 Target DNA  SEQ ID NO: 90

5′ CGGGCTCCGTGCCGCCCTCGCCCCAGCTGGTTTGGAGTTCAACCCCTCGGCTTCCGGCTCCTTGCG
CCTTCGGAGTGTCCCGCAGCGACGGGAGCCGCCGCGGGTACCTAGCCATGGCTGGGGCGA 3′

Bisulfite-converted target DNA with primer sites:

1.  SEQ ID NO: 91                                    3.

5′ CGGGTTTCGTGTCGTTTTCGTTTTGGAGTTTAATTTTCGGTTTCGTCGTCGGTTTTTTGCG
TTTTCGGAGTGTTTCGTAGCGACGTCGGGAGTCGACGCGTCGCGGGGTATTTAGTTATGGTTGGGGCGA 3′

4.                                          2.

PCR-Flap assay design:

Arm1-CGGTTTTTTGCG/3C6/  SEQ ID NO: 92
SEQ ID NO: 27    |||||||||||||||
5′ GTTTAATTTTCGGTTTCGTCGTCGGAGTGTTTCGTAGCG 3′
   ||||||||||||||||||||||||||||||||||||||
   GTTTAATTTTCGGTTTCGTCGTCGGAGTGTTTCGTAGCG
SEQ ID NO: 28               <<AGCCTCACAAAGCATCGC
                              SEQ ID NO: 29

1. BMP3 Outer Forward Primer:    5′ GGTTTCGTGCGTTTTCGTTTTAGT 3′
                                                         SEQ ID NO: 25
2. BMP3 Outer Reverse Primer:    5′ CCAACCATAACTAAATACCCGCG 3′
                                                         SEQ ID NO: 26
3. BMP3 PCR/Flap assay Forward Primer:                   SEQ ID NO: 28
   5′ GTTTAATTTTCGGTTTCGTCGTC 3′
4. BMP3 PCR/Flap assay Reverse Primer:
   5′ CGCTACGAAACACTCCGA 3′                              SEQ ID NO: 29
5. BMP3 Flap oligonucleotide:
   5′ CGCCGAGGCGGTTTTTGCG/3C6/3′                         SEQ ID NO: 30

FIG. 5D

NDRG4 Target DNA    SEQ ID NO: 93

5′ GACCGGGGTGTCCCCAGGCTCCCGGTCGCGGTCCCGCGGTCCCCGTCGCCCACCGGGCACCC
CAGCCGCGCGGAGAAGGCGGAAGCCACGCGCGAGGACCGCGGTC 3′

Bisulfite-converted target DNA with primer sites:

1.      SEQ ID NO: 94         3.

5′ GATCGGGGTGTTTTTAGGTTTCGCGTCGCGGTTTCGTTGTTTTTCGGTTCGTTTATCGGGTATTT
TAGTCGCGTAGAAGGCGGAAGTTACGCGGAGGGATCGCGGGTT 3′
      4.                                              2.

PCR-Flap assay design:

SEQ ID NO: 37      Arm5-GTTCGTTTATCG/3C6/ SEQ ID NO: 95

5′ CGGTTTTCGTTTCGTTTTTTCGTTCGTTTATCGGGTATTTTAGTCGCGTAGAAGGCGG    3′
   |||||||||||||||||||||||||||||||||||
   CGGTTTTCGTTTCGTTTTTTCG                           ::::::::::::
SEQ ID NO: 38                                         <<ATCAGGCGCATCTTCCGCC
                                                              SEQ ID NO: 39

1. NDRG4 Outer Forward Primer:     5′ GGTGTTTTTAGGTTTCGCGTC 3′
                                                               SEQ ID NO: 35
2. NDRG4 Outer Reverse Primer:     5′ GATCCCTCGCGCGTAAC 3′
                                                                SEQ ID NO: 36
3. NDRG4 PCR/Flap assay Forward Primer:  5′ CGGTTTTCGTTTCGTTTTTTCG 3′
                                                                 SEQ ID NO: 38
4. NDRG4 PCR/Flap assay Reverse Primer:  5′ CCGCCTTCTACGCGACTA 3′
                                                                 SEQ ID NO: 39
5. NDRG4 Flap oligonucleotide:     5′ CCACGGACGGTTCGTTTATCG/3C6/ 3′
                                                              SEQ ID NO: 40

FIG. 5E

β-actin Target DNA SEQ ID NO: 96

5' CTCTGCAGGTTCTATTTGCTTTTTCTGGTGTTTGTCTCTCTGACTAGTGTCTAA
GACAGTGTTGGGTGTAGGTACTAACACTGGCCTCGTGTGAGGCCATGAGGCTGGTGTAAGCGGCCTTGGAG
TGTGTATTAAGTAGGTG 3'

Bisulfite-converted target DNA with primer sites:

SEQ ID NO: 97

5' T[TTTGTAGGTTTTATTTGTTTTTTTTAGATGAGTT[TTTGTTTTTTTGATTAGGTGTTTAA
                    1.                              3.
GATAGTGTTGTGGGTGTAGGTATTAATATTGGTTTGTGTGATAAGGTTATGAGGTTGGTAA|AGTGGTTTTGGAG
                                                   4.                    2.
TGTGTATTAAGTAG|GTG 3'

PCR-Flap assay design:

SEQ ID NO: 47            Arm3-ATAGTGTTGTGTGG/3C6/ SEQ ID NO: 98
5' TTTGTTTTTTTGATTAGGTGTTTAAGATAGTGTTGTGGGTGTAGGTATTAATATTGGTTTGTGTGATAAGGTTATGAGGTTGGTG 3'
   |||||||||||||||||||||
   TTTGTTTTTTTGATTAGGTGTTTAAGA>>              SEQ ID NO: 49   <<CTATTCCAATACTCCAACCAC
   SEQ ID NO: 48                                                              SEQ ID NO: 45

1. β-actin Outer Forward Primer:        5' TTGTAGGTTTTATTTGTTTTTTTTAGATGAGTTT 3'
2. β-actin Outer Reverse Primer:        5' CTACTTAATACACACTCCAAAACCACT 3'         SEQ ID NO: 46
                                                                                  SEQ ID NO: 48
3. β-actin PCR/Flap assay Forward Primer:    5' TTTGTTTTTTTGATTAGGTGTTTAAGA 3'
4. β-actin PCR/Flap assay Reverse Primer:    5' CACCAACCTCATAACCTTATC3'
                                                                   SEQ ID NO: 49
5. β-actin Flap oligonucleotide:        5' GACGCGGAGATAGTGTTGTGG/3C6/ 3'
                                                                   SEQ ID NO: 79

FIG. 5F

ZDHHC1 Target DNA    SEQ ID NO: 99

5' GGGCAGGCGCCGCTCTGGCCGGGGGCCGGGACAGCCCACGCTGGCGGGCAGGCGGTGCGCC
CCCGGGGCCGCCCCCGGCGGGCCCAGGCGGCGCCGGGGCCGCCGGGGAGCCGGAGCCTGGGAGGCTGGTCTGGCTTAGCTGG 3'
GCCGTTTTCGTGAGTTCGATAGTTTACGTTGGGCGGTAGGCGGTGCGTTC

Bisulfite-converted target DNA with primer sites:

1.                SEQ ID NO: 100              3.

5' GGGTAGCGTCGTTTTGGTCGTTTCGCGGGGGTCGATAGTTTACGTTGGGCGGTAGGCGGTGCGTTC

GTCGTTTTCGTGAGTTCGATAGCGGGCGAGTTTAGGGCCGTCGGGCCGGTCGGGAGTTGGTTTGGTTTAGTTGG
  4.                                2.

PCR-Flap assay design:

GCACGCAAGCAG-Arm3   SEQ ID NO: 101
    SEQ ID NO: 57                                   : : : : : : : : :
5' GTCGGGGTCGATAGTTTACGTTGGGCGGTAGGCGGTGCGTTCGTTTTCGTGAGTTCGAGT 3'
   | | | | | | | | | | | | | | | | | | | |         : : : : : : : : : : :
   GTCGGGGTCGATAGTTTACG>>                           <<GCAAAAGCACTCAAGCTCA
   SEQ ID NO: 58                                    SEQ ID NO: 59

SEQ ID NO: 55
1. ZDHHC1 Outer Forward Primer:    5' AGCGTCGTTTTGGTCGTTTC 3'
2. ZDHHC1 Outer Reverse Primer:    5' GACGCCCTAAACTCGCC 3'
                                                SEQ ID NO: 56
                                   SEQ ID NO: 58
3. ZDHHC1 PCR/Flap assay Forward Primer: 5' GTCGGGGTCGATAGTTTACG 3'
4. ZDHHC1 PCR/Flap assay Reverse Primer: 5' ACTCGAACTCACGAAAACG 3'
                                         SEQ ID NO: 59
5. ZDHHC1 Flap oligonucleotide:    5' GACGCGGAGGACGAACGCACG/3C6/ 3'
                                   SEQ ID NO: 60

FIG. 6

| SampleID | Cycles | NDRG4 strands | BMP3 strands | BTACT strands | VAV3 strands | S897 strands | ZDDHC1 strands | %NDRG4 | %BMP3 | %VAV3 | %S897 | %ZDDHC1 |
|---|---|---|---|---|---|---|---|---|---|---|---|---|
| | | | | | | | | colspan="5" %Methylation (relative to ZDDHC1) | | | | |
| 1-3 | 5 | 1,409 | 595 | 1,462 | 1,234 | 1,014 | 1,805 | 78% | 33% | 68% | 56% | 100% |
| 4-6 | 7 | 10,033 | 4,490 | 9,369 | 6,672 | 5,938 | 15,364 | 65% | 29% | 43% | 39% | 100% |
| 7-9 | 10 | 47,177 | 19,750 | 38,780 | 42,786 | 36,079 | 124,873 | 38% | 16% | 34% | 29% | 100% |

FIG. 7

Flap assay with no pre-Amplification (4 replicate QuARTS)

| SampleID | NDRG4 strands | BMP3 strands | BTACT strands | VAV3 strands | S897 strands | ZDDHC1 strands | %NDRG4 | %BMP3 | %VAV3 | %S897 | %ZDDHC1 |
|---|---|---|---|---|---|---|---|---|---|---|---|
| Estimated strands without dilution or preamplification | 954 | 426 | 872 | 1441 | 659 | 2590 | 37% | 16% | 25% | 25% | 297% |
| Estimated strands diluted 1:10, without preamplification | 12 | 6 | 16 | 23 | 8 | 45 | 27% | 13% | 17% | 17% | 272% |
| Theoretical amplified strands | 24,536 | 12,069 | 33,753 | 46,344 | 15,698 | 91,722 | | | | | |

11 cycle pre-PCR/ 1:10 dilution/ (2 replicate PCR-flap assays)

| SampleID | 10X Rxn Bf+ in Pre-PCR | Primer Arrangement | [Primer Conc (ea)] | NDRG4 strands | BMP3 strands | BTACT strands | VAV3 strands | S897 strands | ZDDHC1 strands | %NDRG4 | %BMP3 | %VAV3 | %S897 | %ZDDHC1 |
|---|---|---|---|---|---|---|---|---|---|---|---|---|---|---|
| 1 | PCR | Nested | 20 nM | 20 | 14 | 29 | 52 | 31 | 39 | 50% | 34% | 133% | 78% | 100% |
| 2 | | | 100 nM | 39 | 42 | 29 | 190 | 80 | 116 | 33% | 36% | 163% | 69% | 100% |
| 3 | | | 500 nM | 190 | 673 | 55 | 1,387 | 1,847 | 455 | 42% | 148% | 305% | 406% | 100% |
| 4 | PCR | Non-nested | 20 nM | 30 | 43 | 78 | 56 | 33 | 58 | 52% | 75% | 97% | 58% | 100% |
| 5 | | | 100 nM | 65 | 44 | 64 | 455 | 66 | 164 | 40% | 27% | 278% | 40% | 100% |
| 6 | | | 500 nM | 113 | 115 | 103 | 7,852 | 163 | 876 | 13% | 13% | 896% | 19% | 100% |
| 7 | Flap assay | Nested | 20 nM | 4,304 | 2,355 | 3,265 | 18,474 | 9,826 | 11,085 | 39% | 21% | 167% | 89% | 100% |
| 8 | | | 100 nM | 26,950 | 8,016 | 22,159 | 51,204 | 32,635 | 55,438 | 49% | 14% | 92% | 59% | 100% |
| 9 | | | 500 nM | 46,338 | 14,350 | 34,855 | 71,679 | 85,947 | 152,463 | 30% | 9% | 47% | 56% | 100% |
| 10 | Flap assay | Non-nested | 20 nM | 17,084 | 4,791 | 23 | 26,294 | 9,081 | 27,148 | 63% | 18% | 97% | 33% | 100% |
| 11 | | | 100 nM | 111,863 | 41,706 | 2,369 | 116,338 | 58,688 | 236,314 | 47% | 18% | 49% | 25% | 100% |
| 12 | | | 500 nM | 22,582 | 78,335 | 16,796 | 191,221 | 52,142 | 420,780 | 5% | 19% | 45% | 12% | 100% |
| Control 1 | Flap assay | Nested | 500 nM | 0 | 0 | 0 | 0 | 0 | 0 | N/A | N/A | N/A | N/A | N/A |
| Control 2 | PCR | Non-nested | 500 nM | 0 | 0 | 0 | 0 | 0 | 0 | N/A | N/A | N/A | N/A | N/A |
| Control 3 | Flap assay | Nested | 500 nM | 0 | 0 | 0 | 0 | 0 | 0 | N/A | N/A | N/A | N/A | N/A |
| Control 4 | PCR | Non-nested | 500 nM | 0 | 0 | 0 | 0 | 0 | 0 | N/A | N/A | N/A | N/A | N/A |

% Methylation (relative to ZDDHC1)

FIG. 8A

| SampleID | Sample Type | Strands per Reaction | | | | | |
|---|---|---|---|---|---|---|---|
| | | NDRG4 | BMP3 | BTACT | VAV3 | S897 | ZDHHC1 |
| Normal Plasma | No Pre-Amp | 0 | 0 | 681 | 0 | 0 | 1 |
| Theoretical strands/rxn after multiplex Pre-Amp | 5 cycles | 0 | 0 | 218 | 0 | 0 | 0 |
| | 10cycles | 0 | 0 | 13,951 | 0 | 0 | 21 |
| | 20cycles | 0 | 25 | 14,286,060 | 0 | 0 | 21,711 |
| | 25cycles | 0 | 801 | 457,153,922 | 0 | 0 | 694,751 |
| Normal Plasma +21ul CCM | No Pre-Amp | 262 | 133 | 1,027 | 251 | 159 | 279 |
| Theoretical strands/rxn after multiplex Pre-Amp | 5 cycles | 168 | 85 | 657 | 161 | 102 | 178 |
| | 10cycles | 5,371 | 2,727 | 21,035 | 5,150 | 3,258 | 5,706 |
| | 20cycles | 5,499,930 | 2,792,066 | 21,539,883 | 5,273,387 | 3,336,078 | 5,843,227 |
| | 25cycles | 175,997,755 | 89,346,125 | 689,276,245 | 168,748,376 | 106,754,506 | 186,983,255 |

FIG. 8B

| SampleID | Sample Type | Cycles | Strands per Reaction ||||||
|---|---|---|---|---|---|---|---|---|
| | | | NDRG4 | BMP3 | BTACT | VAV3 | S897 | ZDHHC1 |
| 1-2 | Normal Plasma +21ul CCM | 5 | 189 | 191 | 733 | 163 | 91 | 257 |
| 3-4 | Normal Plasma | 5 | 0 | 0 | 345 | 0 | 0 | 2 |
| NTC-f5 | Fish DNA Diluent | 5 | 0 | 1 | 0 | 0 | 0 | 0 |
| NTC-t5 | Tris EDTA buffer | 5 | 0 | 0 | 0 | 0 | 0 | 0 |
| 5-6 | Normal Plasma +21ul CCM | 10 | 6,180 | 5,091 | 19,877 | 6,285 | 2,752 | 9,422 |
| 7-8 | Normal Plasma | 10 | 0 | 3 | 8,263 | 0 | 0 | 8 |
| NTC-f10 | Fish DNA Diluent | 10 | 0 | 0 | 0 | 0 | 0 | 0 |
| NTC-t10 | Tris EDTA buffer | 10 | 0 | 0 | 0 | 0 | 0 | 0 |
| 9-10 | Normal Plasma +21ul CCM | 20 | 3,668,073 | Out of Range | 1,690,537 | 1,227,373 | 436,520 | Out of Range |
| 11-12 | Normal Plasma | 20 | 0 | 2 | 1,079,721 | 0 | 1 | 4,273 |
| NTC-f20 | Fish DNA Diluent | 20 | 0 | 0 | 0 | 2 | 0 | 0 |
| NTC-t20 | Tris EDTA buffer | 20 | 0 | 0 | 0 | 0 | 0 | 0 |
| 13-14 | Normal Plasma +21ul CCM | 25 | Out of Range | 6,029,291 | 1,895,229 | 21,897,908 | 12,192,303 | 20,788,101 |
| 15-16 | Normal Plasma | 25 | 12 | 22 | 1,645,426 | 0 | 32 | 260,831 |
| NTC-f25 | Fish DNA Diluent | 25 | 0 | 0 | 0 | 0 | 0 | 0 |
| NTC-t25 | Tris EDTA buffer | 25 | 0 | 0 | 0 | 1 | 0 | 0 |
| Normal Plasma | Direct QuARTs (N.Plasma) | N/A | 0 | 0 | 681 | 0 | 0 | 1 |
| NP+21ul CCM | Direct QuARTs (N.Plasma+21ulCCM) | N/A | 262 | 133 | 1,027 | 251 | 159 | 279 |
| NTC, fDNA | QuARTs CTRL (fish DNA dil) | N/A | 0 | 0 | 0 | 0 | 0 | 0 |
| NTC, Te | QuARTs CTRL (Tris EDTA buffer) | N/A | 0 | 0 | 0 | 0 | 0 | 0 |

FIG. 8C

% Methylation (based on ZDHHC1)

| SampleID | Sample Type | Cycles | NDRG4 strands | BMP3 strands | BTACT strands | VAV3 strands | S897 strands | ZDHHC1 strands |
|---|---|---|---|---|---|---|---|---|
| 1-2 | N. Plasma + 21ul CCM | 5 | 73% | 75% | | 64% | 36% | 100% |
| 5-6 | N. Plasma + 21ul CCM | 10 | 66% | 54% | | 67% | 29% | 100% |
| 9-10 | N. Plasma + 21ul CCM | 20 | ND | ND | | ND | ND | ND |
| 13-14 | N. Plasma + 21ul CCM | 25 | ND | 29% | | 105% | 59% | 100% |
| NP+21ul CCM | Direct QuARTs (N.Plasma+21ulCCM) | N/A | 94% | 48% | | 90% | 57% | 100% |

% Recovery

| SampleID | Sample Type | Cycles | NDRG4 strands | BMP3 strands | BTACT strands | VAV3 strands | S897 strands | ZDHHC1 strands |
|---|---|---|---|---|---|---|---|---|
| 1-2 | N. Plasma + 21ul CCM | 5 | 112% | 225% | 112% | 101% | 90% | 144% |
| 3-4 | Normal Plasma | 5 | | | 158% | | | 474% |
| NTC-f5 | Fish DNA Diluent | 5 | | | | | | |
| NTC-t5 | Tris EDTA buffer | 5 | | | | | | |
| 5-6 | N. Plasma + 21ul CCM | 10 | 115% | 187% | 94% | 122% | 84% | 165% |
| 7-8 | Normal Plasma | 10 | | | 59% | | | 37% |
| NTC-f10 | Fish DNA Diluent | 10 | | | | | | |
| NTC-t10 | Tris EDTA buffer | 10 | | | | | | |
| 9-10 | N. Plasma + 21ul CCM | 20 | 67% | ND | 8% | 23% | 13% | ND |
| 11-12 | Normal Plasma | 20 | | 7% | 8% | | | 20% |
| NTC-f20 | Fish DNA Diluent | 20 | | | | | | |
| NTC-t20 | Tris EDTA buffer | 20 | | | | | | |
| 13-14 | N. Plasma + 21ul CCM | 25 | ND | 7% | 0% | 13% | 11% | 11% |
| 15-16 | Normal Plasma | 25 | #DIV/0! | 3% | 0% | #DIV/0! | #DIV/0! | 38% |
| NTC-f25 | Fish DNA Diluent | 25 | | | | | | |
| NTC-t25 | Tris EDTA buffer | 25 | | | | | | |
| Normal Plasma | Direct QuARTs (N.Plasma) | N/A | | | | | | |
| NP+21ul CCM | Direct QuARTs (N.Plasma+21ulCCM) | N/A | | | | | | |
| NTC, fDNA | QuARTs CTRL (fDNA dil) | N/A | | | | | | |
| NTC, Te | QuARTs CTRL (Tris EDTA buffer) | N/A | | | | | | |

FIG. 9

Measured QuARTS

| SampleID | Pathology | NDRG4 | BMP3 | BTACT | VAV3 | SFMB2 | ZDHHC1 | | % Methylation | | | |
| --- | --- | --- | --- | --- | --- | --- | --- | --- | --- | --- | --- | --- |
| | | | | | | | | % NDRG4 | % BMP3 | % VAV3 | % SFMB2 |
| 5802237 | AA | 73 | 53 | 7,723 | 1,239 | 159 | 3,217 | 2.3% | 1.7% | 38.5% | 4.9% |
| 5800621 | ACA | 779 | 54 | 10,793 | 276 | 361 | 1,876 | 41.5% | 2.9% | 14.7% | 19.3% |
| 7801116 | Normal | 0 | 0 | 703 | 1 | 3 | 380 | 0.1% | 0.0% | 0.2% | 0.7% |
| 7800687 | Normal | 1 | 0 | 1,754 | 4 | 1 | 564 | 0.2% | 0.0% | 0.7% | 0.1% |

Theoretical mpQuARTS

| SampleID | Pathology | NDRG4 | BMP3 | BTACT | VAV3 | SFMB2 | ZDHHC1 |
| --- | --- | --- | --- | --- | --- | --- | --- |
| 5802237 | | 1,496 | 1,090 | 158,172 | 25,368 | 3,251 | 65,880 |
| 5800621 | | 15,959 | 1,112 | 221,049 | 5,643 | 7,397 | 38,418 |
| 7801116 | | 8 | 0 | 14,407 | 14 | 54 | 7,776 |
| 7800687 | | 18 | 0 | 35,925 | 77 | 11 | 11,545 |

Measured mpQuARTS

| SampleID | Pathology | NDRG4 | BMP3 | BTACT | VAV3 | SFMB2 | ZDHHC1 | | % Methylation | | | |
| --- | --- | --- | --- | --- | --- | --- | --- | --- | --- | --- | --- | --- |
| | | | | | | | | % NDRG4 | % BMP3 | % VAV3 | % SFMB2 |
| 5802237 | AA | 235 | 572 | 47,821 | 23,748 | 1,575 | 59,396 | 0.4% | 1.0% | 40.0% | 2.7% |
| 5800621 | ACA | 5,320 | 869 | 66,220 | 5,735 | 4,582 | 38,352 | 13.9% | 2.3% | 15.0% | 11.9% |
| 7801116 | Normal | 0 | 0 | 7,956 | 26 | 3 | 7,705 | 0.0% | 0.0% | 0.3% | 0.0% |
| 7800687 | Normal | 0 | 0 | 6,418 | 37 | 13 | 10,298 | 0.0% | 0.0% | 0.4% | 0.1% |
| No Target Control | | 0 | 0 | 0 | 23 | 0 | 0 | | | | |

Back calculated QuARTS

| SampleID | Pathology | NDRG4 | BMP3 | BTACT | VAV3 | SFMB2 | ZDHHC1 |
| --- | --- | --- | --- | --- | --- | --- | --- |
| 5802237 | AA | 11 | 28 | 2,335 | 1,160 | 77 | 2,900 |
| 5800621 | ACA | 260 | 42 | 3,233 | 280 | 224 | 1,873 |
| 7801116 | Normal | 0 | 0 | 388 | 1 | 0 | 376 |
| 7800687 | Normal | 0 | 0 | 313 | 2 | 1 | 503 | multiplex PCR Efficiency

| SampleID | Pathology | NDRG4 | BMP3 | BTACT | VAV3 | SFMB2 | ZDHHC1 |
| --- | --- | --- | --- | --- | --- | --- | --- |
| 5802237 | AA | 16% | 52% | 30% | 94% | 48% | 90% |
| 5800621 | ACA | 33% | 78% | 30% | 102% | 62% | 100% |
| 7801116 | Normal | - | - | 55% | - | - | 99% |
| 7800687 | Normal | - | - | 18% | - | - | 89% |

FIG. 10A

| SampleID | final Site Category | Histology, Cancer | grade | Multiplex PreAmp + PCR-Flap Assay Strands/rxn | | | | | | Direct PCR-Flap Assay (NO PreAmp) | | | | | |
|---|---|---|---|---|---|---|---|---|---|---|---|---|---|---|---|
| | | | | NDRG4 | BMP3 | BTACT | VAV3 | SEPT9 | ZDHHC1 | NDRG4 | BMP3 | BTACT | VAV3 | SEPT9 | ZDHHC1 |
| 1503401149 | Colorectal/Normal | | | 0 | 863 | 119,214 | 0 | 0 | 400 | 0 | 41 | 15,388 | 0 | 0 | 10 |
| 1503401151 | Colorectal/Normal | Adenocarcinoma | grade 2/well | 20 | 77 | 1,343 | 18 | 11 | 131 | 11 | 4 | 148 | 9 | 0 | 8 |
| 1503401152 | Colorectal/Normal | Adenocarcinoma | grade 3/moderate | 0 | 99 | 382 | 47 | 7 | 471 | 0 | 4 | 47 | 5 | 3 | 20 |
| 1503401153 | Colorectal/Normal | | | 0 | 0 | 1,602 | 0 | 0 | 32 | 0 | 0 | 110 | 0 | 0 | 0 |
| 1503401154 | Colorectal/Normal | | | 0 | 0 | 897 | 0 | 0 | 0 | 0 | 0 | 46 | 0 | 0 | 0 |
| 1503401156 | Colorectal/Normal | | | 0 | 0 | 1,868 | 0 | 0 | 0 | 0 | 0 | 161 | 0 | 0 | 2 |
| 1503401157 | Colorectal/Normal | Adenocarcinoma | grade 4/poorly | 0 | 0 | 12,495 | 0 | 1 | 10,660 | 0 | 0 | 1,897 | 0 | 0 | 397 |
| 1503401158 | Colorectal/Normal | Adenocarcinoma | grade 4/poorly | 125,107 | 72,687 | 113,595 | 127,562 | 21,736 | 125,381 | 3,551 | 1,636 | 4,691 | 3,705 | 829 | 3,109 |
| 1503401160 | Stomach | Adenocarcinoma | grade 4/poorly | 25 | 5 | 4,155 | 123 | 4 | 151 | 15 | 5 | 721 | 8 | 2 | 9 |
| 1503401161 | Colorectal/Normal | Adenocarcinoma | grade 4/poorly | 17,400 | 12,985 | 21,292 | 9,750 | 5,226 | 28,690 | 932 | 334 | 1,525 | 389 | 307 | 924 |
| 1503401162 | Colorectal/Normal | Adenocarcinoma | grade 3/moderate | 0 | 14,817 | 46,702 | 66,058 | 7 | 135,554 | 0 | 310 | 3,367 | 2,036 | 0 | 3,624 |
| 1503401163 | Colorectal/Normal | Adenocarcinoma | grade 3/moderate | 0 | 0 | 1,375 | 0 | 0 | 484 | 0 | 0 | 80 | 0 | 0 | 25 |
| 1503401164 | Colorectal/Normal | | | 0 | 0 | 1,588 | 0 | 0 | 38 | 0 | 2 | 65 | 0 | 0 | 0 |
| 1503401165 | Stomach | Adenocarcinoma | U | 0 | 0 | 9,100 | 0 | 0 | 0 | 0 | 0 | 106 | 0 | 0 | 0 |
| 1503401166 | Stomach | Adenocarcinoma | grade 3/moderate | 0 | 0 | 5,876 | 0 | 0 | 133 | 0 | 0 | 178 | 0 | 0 | 8 |
| 1503401167 | Colorectal/Normal | Adenocarcinoma | grade 3/moderate | 60,317 | 1 | 102,684 | 70,060 | 16,476 | 86,062 | 1,732 | 0 | 3,661 | 1,277 | 408 | 1,980 |
| 1503401168 | Stomach | Adenocarcinoma | grade 3/moderate | 0 | 0 | 941 | 0 | 0 | 649 | 0 | 0 | 125 | 0 | 0 | 26 |
| 1503401169 | Colorectal/Normal | Adenocarcinoma | grade 3/moderate | 0 | 0 | 1,989 | 0 | 0 | 68 | 0 | 0 | 175 | 0 | 0 | 4 |
| 1503401170 | Colorectal/Normal | Adenocarcinoma | grade 4/poorly | 0 | 0 | 1,982 | 21 | 0 | 16 | 0 | 0 | 131 | 0 | 0 | 0 |
| 1503401171 | Stomach | Adenocarcinoma | grade 4/poorly | 0 | 0 | 1,423 | 0 | 0 | 0 | 0 | 0 | 125 | 0 | 0 | 2 |
| 1503401172 | Colorectal/Normal | Adenocarcinoma | grade 3/moderate | 581 | 2,214 | 5,814 | 2,368 | 108 | 4,724 | 65 | 66 | 413 | 102 | 6 | 176 |
| 1503401173 | Colorectal/Normal | Adenocarcinoma | grade 3/moderate | 0 | 0 | 3,096 | 0 | 35 | 864 | 0 | 0 | 357 | 0 | 1 | 30 |
| 1503401175 | Colorectal/Normal | | | 0 | 0 | 3,101 | 0 | 0 | 26 | 0 | 0 | 132 | 0 | 0 | 2 |
| 1503401176 | Colorectal/Normal | | | 0 | 0 | 866 | 0 | 0 | 11 | 0 | 0 | 100 | 0 | 0 | 2 |
| 1503401177 | Colorectal/Normal | Adenocarcinoma | grade 4/poorly | 0 | 32 | 1,316 | 0 | 0 | 0 | 0 | 0 | 119 | 0 | 0 | 6 |
| 1503401178 | Colorectal/Normal | | | 0 | 0 | 228,629 | 50 | 4 | 45 | 4 | 9 | 25,397 | 0 | 0 | 3 |
| 1503401179 | Colorectal/Normal | Adenocarcinoma | grade 3/moderate | 0 | 0 | 2,674 | 1 | 0 | 0 | 0 | 1 | 116 | 1 | 0 | 3 |
| 1503401180 | Stomach | Adenocarcinoma | grade 1 | 0 | 1 | 1,076 | 0 | 0 | 104 | 0 | 0 | 61 | 2 | 0 | 2 |

FIG. 10B

| SampleID | final Site Category | Histology, Cancer | grade | Multiplex Pre-Amp + PCR Flap Assay Strands/rxn |  |  |  |  | Direct PCR-Flap Assay (No PCR Pre-Amp) |  |  |  |  |
|---|---|---|---|---|---|---|---|---|---|---|---|---|---|
| | | | | NDRG4 | BMP3 | BTACT | VAV3 | SFMBT2 | ZDHHC1 | NDRG4 | BMP3 | BTACT | VAV3 | SFMBT2 | ZDHHC1 |
| 1503401181 | Stomach | Adenocarcinoma | grade 3/moderate | 0 | 0 | 16,130 | 0 | 0 | 0 | 0 | 0 | 213 | 0 | 0 | 0 |
| 1503401182 | Stomach | Adenocarcinoma | U | 80 | 42 | 2,801 | 375 | 0 | 689 | 19 | 1 | 155 | 10 | 1 | 19 |
| 1503401183 | Colorectal/Normal | Adenocarcinoma | grade 3/moderate | 0 | 0 | 1,369 | 10 | 0 | 52 | 0 | 0 | 105 | 0 | 0 | 1 |
| 1503401184 | Colorectal/Normal | | | 0 | 0 | 1,993 | 0 | 0 | 19 | 0 | 0 | 90 | 0 | 0 | 3 |
| 1503401185 | Colorectal/Normal | | | 0 | 0 | 2,214 | 0 | 0 | 38 | 0 | 0 | 86 | 0 | 0 | 4 |
| 1503401186 | Stomach | Adenocarcinoma | grade 4/poorly | 0 | 2 | 3,013 | 0 | 0 | 154 | 0 | 2 | 234 | 0 | 0 | 3 |
| 1503401187 | Colorectal/Normal | | | 0 | 0 | 8,627 | 0 | 0 | 0 | 0 | 0 | 368 | 0 | 0 | 1 |
| 1503401188 | Bile duct | | | 0 | 0 | 929 | 0 | 0 | 21 | 0 | 0 | 126 | 0 | 0 | 4 |
| 1503401189 | Colorectal/Normal | | | 0 | 0 | 606 | 0 | 0 | 0 | 0 | 0 | 57 | 0 | 0 | 0 |
| 1503401190 | Colorectal/Normal | | | 0 | 0 | 1,659 | 0 | 0 | 4 | 0 | 0 | 71 | 0 | 0 | 0 |
| 1503401191 | Colorectal/Normal | Adenocarcinoma | grade 3/moderate | 13,862 | 0 | 6,782 | 17,430 | 4,635 | 19,018 | 469 | 0 | 943 | 574 | 213 | 502 |
| 1503401192 | Colorectal/Normal | | | 0 | 0 | 695 | 0 | 0 | 21 | 0 | 0 | 64 | 0 | 0 | 0 |
| 1503401193 | Colorectal/Normal | Other | U | 46,219 | 17,329 | 26,613 | 57,917 | 7,921 | 58,169 | 1,829 | 480 | 2,239 | 2,271 | 421 | 1,939 |
| 1503401194 | Colorectal/Normal | Squamous Cell | grade 3/moderate | 33,593 | 16,483 | 13,425 | 240 | 3,444 | 51,199 | 1,180 | 324 | 1,909 | 13 | 183 | 1,922 |
| 1503401195 | Colorectal/Normal | Adenocarcinoma | U | 2,137 | 1,377 | 6,043 | 3,300 | 354 | 5,665 | 179 | 44 | 562 | 148 | 43 | 244 |
| 1503401196 | Stomach | Adenocarcinoma | grade 3/moderate | 27 | 119 | 561 | 218 | 62 | 347 | 9 | 3 | 46 | 2 | 0 | 8 |
| 1503401197 | Colorectal/Normal | Adenocarcinoma | grade 3/moderate | 474 | 0 | 1,556 | 1,093 | 33 | 2,233 | 23 | 0 | 96 | 21 | 2 | 37 |
| 1503401198 | Colorectal/Normal | Adenocarcinoma | grade 4/poorly | 28 | 451 | 4,264 | 110 | 0 | 857 | 16 | 9 | 125 | 5 | 0 | 17 |
| 1507705066 | Stomach | Adenocarcinoma | grade 4/poorly | 0 | 0 | 1,755 | 0 | 0 | 22 | 0 | 0 | 82 | 0 | 0 | 0 |
| 1507705067 | Stomach | Adenocarcinoma | grade 4/poorly | 0 | 0 | 1,965 | 0 | 0 | 42 | 0 | 0 | 118 | 0 | 0 | 2 |
| 1507705068 | Colorectal/Normal | | | 0 | 0 | 4,406 | 0 | 0 | 0 | 0 | 0 | 100 | 0 | 0 | 0 |
| 1507705070 | Colorectal/Normal | Adenocarcinoma | grade 4/poorly | 10,618 | 647 | 12,943 | 15,040 | 2,671 | 15,743 | 262 | 19 | 713 | 475 | 103 | 406 |

FIG. 10C

| SampleID | Final Site Category | Histology, Cancer | grade | Multiplex Pre-Amp + PCR-Flap Assay Strands/rxn | | | | | | Direct Flap Assay (NO Pre-Amp) | | | | | |
|---|---|---|---|---|---|---|---|---|---|---|---|---|---|---|---|
| | | | | NDRG4 | BMP3 | BTACT | VAV3 | S897 | ZDHHC1 | NDRG4 | BMP3 | BTACT | VAV3 | S897 | ZDHHC1 |
| 1507705071 | Colorectal/Normal | | | 0 | 0 | 1,622 | 0 | 0 | 19 | 0 | 0 | 97 | 0 | 0 | 5 |
| 1507705072 | Colorectal/Normal | | | 0 | 0 | 5,291 | 0 | 0 | 183 | 0 | 0 | 338 | 0 | 0 | 2 |
| 1507705073 | Colorectal/Normal | Adenocarcinoma | grade 3/moderate | 42 | 0 | 3,370 | 0 | 32 | 291 | 16 | 0 | 344 | 0 | 3 | 19 |
| 1507705074 | Stomach | Adenocarcinoma | grade 4/poorly | 0 | 6 | 1,076 | 101 | 0 | 198 | 2 | 0 | 147 | 0 | 0 | 11 |
| 1507705075 | Colorectal/Normal | Adenocarcinoma | grade 3/moderate | 49 | 0 | 2,257 | 0 | 15 | 443 | 10 | 0 | 122 | 0 | 0 | 9 |
| 1507705076 | Colorectal/Normal | | | 0 | 0 | 1,614 | 0 | 0 | 0 | 0 | 0 | 61 | 0 | 0 | 0 |
| 1507705077 | Stomach | Adenocarcinoma | grade 4/poorly | 0 | 0 | 2,391 | 0 | 0 | 0 | 3 | 0 | 125 | 0 | 0 | 3 |
| 1507705078 | Stomach | Adenocarcinoma | grade 4/poorly | 0 | 0 | 3,512 | 0 | 0 | 6 | 0 | 0 | 111 | 0 | 0 | 2 |
| 1507705079 | Stomach | Adenocarcinoma | grade 4/poorly | 0 | 0 | 6,760 | 0 | 0 | 0 | 0 | 0 | 249 | 0 | 0 | 5 |
| 1507705080 | Stomach | Adenocarcinoma | grade 4/poorly | 0 | 21 | 996 | 0 | 0 | 22 | 0 | 0 | 138 | 0 | 0 | 4 |
| 1507705081 | Stomach | | | 0 | 0 | 2,582 | 0 | 0 | 0 | 0 | 0 | 157 | 0 | 0 | 4 |
| 1507705082 | Stomach | Adenocarcinoma | grade 4/poorly | 0 | 0 | 1,494 | 0 | 0 | 29 | 0 | 0 | 77 | 0 | 0 | 0 |
| 1507705083 | Stomach | Adenocarcinoma | grade 3/moderate | 2 | 25 | 3,752 | 26 | 0 | 69 | 0 | 0 | 230 | 1 | 0 | 4 |
| 1507705084 | Colorectal/Normal | | | 0 | 0 | 2,562 | 0 | 0 | 67 | 0 | 0 | 42 | 0 | 0 | 0 |
| 1507705085 | Stomach | Adenocarcinoma | grade 4/poorly | 0 | 7 | 3,533 | 0 | 0 | 0 | 0 | 0 | 101 | 0 | 0 | 0 |
| 1507705086 | Colorectal/Normal | | | 0 | 0 | 2,289 | 0 | 15 | 15 | 0 | 0 | 56 | 0 | 0 | 2 |
| 1507705087 | Stomach | Adenocarcinoma | grade 4/poorly | 0 | 0 | 2,005 | 0 | 0 | 71 | 0 | 0 | 197 | 0 | 0 | 2 |
| 1507705088 | Colorectal/Normal | | | 0 | 0 | 345 | 0 | 0 | 3 | 0 | 0 | 31 | 0 | 0 | 0 |
| 1508204660 | Other | | | 0 | 0 | 1,285 | 0 | 0 | 294 | 0 | 0 | 108 | 0 | 0 | 11 |
| 1508204661 | Colorectal/Normal | Adenocarcinoma | grade 2/well | 0 | 5 | 35,774 | 0 | 0 | 664 | 0 | 5 | 1,587 | 0 | 0 | 12 |
| 1508204662 | Colorectal/Normal | Adenocarcinoma | | 0 | 9 | 1,086 | 0 | 0 | 56 | 0 | 0 | 62 | 0 | 0 | 9 |
| 1508204663 | Stomach | Adenocarcinoma | U | 0 | 0 | 2,169 | 0 | 0 | 0 | 0 | 0 | 109 | 0 | 0 | 0 |
| 1508204664 | Stomach | Adenocarcinoma | grade 3/moderate | 0 | 0 | 1,918 | 0 | 0 | 72 | 0 | 0 | 255 | 0 | 0 | 10 |
| 1508204665 | Stomach | Adenocarcinoma | grade 4/poorly | 0 | 0 | 3,412 | 0 | 0 | 95 | 0 | 0 | 216 | 0 | 0 | 2 |
| 1508204666 | Colorectal/Normal | Adenocarcinoma | grade 3/moderate | 5,015 | 7,235 | 20,993 | 16,773 | 3,667 | 34,878 | 207 | 105 | 663 | 419 | 108 | 816 |

FIG. 10D

| SampleID | final Site Category | Histology, Cancer | grade | Multiplex PreAmp + PCR Flap Assay Strands/rxn | | | | | | | %Methylation | | | | | | |
|---|---|---|---|---|---|---|---|---|---|---|---|---|---|---|---|---|---|
| | | | | NDRG4 | BMP3 | BTACT | VAV3 | SEPT9 | ZDHHC1 | | NDRG4 | BMP3 | BTACT | VAV3 | SEPT9 | ZDHHC1 | |
| 1503401149 | Colorectal/Normal | | | 0 | 863 | 119,214 | 0 | 0 | 400 | | 0.0% | 0.7% | 100.0% | 0.0% | 0.0% | 0.3% | |
| 1503401151 | Colorectal/Normal | Adenocarcinoma | grade 2/well | 20 | 77 | 1,343 | 18 | 11 | 131 | | 1.5% | 5.7% | 100.0% | 1.3% | 0.8% | 9.8% | |
| 1503401152 | Colorectal/Normal | Adenocarcinoma | grade 3/moderate | 0 | 99 | 382 | 47 | 7 | 471 | | 0.0% | 25.9% | 100.0% | 12.2% | 1.8% | 123.5% | |
| 1503401153 | Colorectal/Normal | | | 0 | 0 | 1,602 | 0 | 0 | 32 | | 0.0% | 0.0% | 100.0% | 0.0% | 0.0% | 2.0% | |
| 1503401154 | Colorectal/Normal | | | 0 | 0 | 897 | 0 | 0 | 0 | | 0.0% | 0.0% | 100.0% | 0.0% | 0.0% | 0.0% | |
| 1503401156 | Colorectal/Normal | | | 0 | 0 | 1,868 | 0 | 0 | 0 | | 0.0% | 0.0% | 100.0% | 0.0% | 0.0% | 0.0% | |
| 1503401157 | Colorectal/Normal | Adenocarcinoma | grade 4/poorly | 0 | 0 | 12,495 | 0 | 1 | 10,660 | | 0.0% | 0.0% | 100.0% | 0.0% | 0.0% | 85.3% | |
| 1503401158 | Colorectal/Normal | Adenocarcinoma | grade 4/poorly | 125,107 | 72,687 | 113,595 | 127,562 | 21,736 | 125,381 | | 110.1% | 64.0% | 100.0% | 112.3% | 19.1% | 110.4% | |
| 1503401160 | Stomach | Adenocarcinoma | grade 4/poorly | 25 | 5 | 4,155 | 123 | 4 | 151 | | 0.6% | 0.1% | 100.0% | 3.0% | 0.1% | 3.6% | |
| 1503401161 | Colorectal/Normal | Adenocarcinoma | grade 4/poorly | 17,400 | 12,985 | 21,292 | 9,750 | 5,226 | 28,690 | | 81.7% | 61.0% | 100.0% | 45.8% | 24.5% | 134.7% | |
| 1503401162 | Colorectal/Normal | Adenocarcinoma | grade 3/moderate | 0 | 14,817 | 46,702 | 66,058 | 7 | 135,554 | | 0.0% | 31.7% | 100.0% | 141.4% | 0.0% | 290.3% | |
| 1503401163 | Colorectal/Normal | Adenocarcinoma | grade 3/moderate | 0 | 0 | 1,375 | 0 | 0 | 484 | | 0.0% | 0.0% | 100.0% | 0.0% | 0.0% | 35.2% | |
| 1503401164 | Colorectal/Normal | | | 0 | 0 | 1,588 | 0 | 0 | 38 | | 0.0% | 0.0% | 100.0% | 0.0% | 0.0% | 2.4% | |
| 1503401165 | Stomach | Adenocarcinoma | U | 0 | 0 | 9,100 | 0 | 0 | 0 | | 0.0% | 0.0% | 100.0% | 0.0% | 0.0% | 0.0% | |
| 1503401166 | Stomach | Adenocarcinoma | grade 3/moderate | 0 | 0 | 5,876 | 0 | 0 | 133 | | 0.0% | 0.0% | 100.0% | 0.0% | 0.0% | 2.3% | |
| 1503401167 | Colorectal/Normal | Adenocarcinoma | grade 3/moderate | 60,317 | 1 | 102,684 | 70,060 | 16,476 | 86,062 | | 58.7% | 0.0% | 100.0% | 68.2% | 16.0% | 83.8% | |
| 1503401168 | Stomach | Adenocarcinoma | grade 3/moderate | 0 | 0 | 941 | 0 | 0 | 649 | | 0.0% | 0.0% | 100.0% | 0.0% | 0.0% | 69.0% | |
| 1503401169 | Colorectal/Normal | Adenocarcinoma | grade 3/moderate | 0 | 0 | 1,989 | 0 | 0 | 68 | | 0.0% | 0.0% | 100.0% | 0.0% | 0.0% | 3.4% | |
| 1503401170 | Colorectal/Normal | Adenocarcinoma | grade 3/moderate | 0 | 0 | 1,982 | 21 | 0 | 16 | | 0.0% | 0.0% | 100.0% | 1.0% | 0.0% | 0.8% | |
| 1503401171 | Stomach | Adenocarcinoma | grade 4/poorly | 0 | 0 | 1,423 | 0 | 0 | 0 | | 0.0% | 0.0% | 100.0% | 0.0% | 0.0% | 0.0% | |
| 1503401172 | Colorectal/Normal | Adenocarcinoma | grade 3/moderate | 581 | 2,214 | 5,814 | 2,368 | 108 | 4,724 | | 10.0% | 38.1% | 100.0% | 40.7% | 1.9% | 81.3% | |
| 1503401173 | Colorectal/Normal | Adenocarcinoma | grade 3/moderate | 0 | 0 | 3,096 | 0 | 35 | 864 | | 0.0% | 0.0% | 100.0% | 0.0% | 1.1% | 27.9% | |
| 1503401175 | Colorectal/Normal | | | 0 | 0 | 3,101 | 0 | 0 | 26 | | 0.0% | 0.0% | 100.0% | 0.0% | 0.0% | 0.8% | |
| 1503401176 | Colorectal/Normal | | | 0 | 0 | 866 | 0 | 0 | 11 | | 0.0% | 0.0% | 100.0% | 0.0% | 0.0% | 1.3% | |
| 1503401177 | Colorectal/Normal | Adenocarcinoma | grade 4/poorly | 0 | 0 | 1,316 | 0 | 0 | 0 | | 0.0% | 0.0% | 100.0% | 0.0% | 0.0% | 0.0% | |
| 1503401178 | Colorectal/Normal | | | 0 | 0 | 228,629 | 0 | 0 | 45 | | 0.0% | 0.0% | 100.0% | 0.0% | 0.0% | 0.0% | |
| 1503401179 | Colorectal/Normal | Adenocarcinoma | grade 3/moderate | 0 | 32 | 2,674 | 50 | 4 | 0 | | 0.0% | 0.1% | 100.0% | 1.9% | 0.2% | 0.0% | |
| 1503401180 | Stomach | Adenocarcinoma | grade 1 | 0 | 1 | 1,076 | 1 | 0 | 104 | | 0.0% | 0.0% | 100.0% | 0.1% | 0.0% | 9.7% | |

FIG. 10E

| SampleID | final Site Category | Histology, Cancer | grade | Multiplex PreAmp + PCR Flap Assay Strands/rxn |  |  |  |  |  | %Methylation |  |  |  |  |  |
|---|---|---|---|---|---|---|---|---|---|---|---|---|---|---|---|
| | | | | NDRG4 | BMP3 | BTACT | VAV3 | S897 | ZDHHC1 | NDRG4 | BMP3 | BTACT | VAV3 | S897 | ZDHHC1 |
| 1503401181 | Stomach | Adenocarcinoma | grade 3/moderate | 0 | 0 | 16,130 | 0 | 0 | 0 | 0.0% | 0.0% | 100.0% | 0.0% | 0.0% | 0.0% |
| 1503401182 | Stomach | Adenocarcinoma | U | 80 | 42 | 2,801 | 375 | 0 | 689 | 2.9% | 1.5% | 100.0% | 13.4% | 0.0% | 24.6% |
| 1503401183 | Colorectal/Normal | Adenocarcinoma | grade 3/moderate | 0 | 0 | 1,369 | 10 | 0 | 52 | 0.0% | 0.0% | 100.0% | 0.7% | 0.0% | 3.8% |
| 1503401184 | Colorectal/Normal | | | 0 | 0 | 1,993 | 0 | 0 | 19 | 0.0% | 0.0% | 100.0% | 0.0% | 0.0% | 0.9% |
| 1503401185 | Colorectal/Normal | | | 0 | 0 | 2,214 | 0 | 0 | 38 | 0.0% | 0.0% | 100.0% | 0.0% | 0.0% | 1.7% |
| 1503401186 | Stomach | Adenocarcinoma | grade 4/poorly | 0 | 0 | 3,013 | 0 | 0 | 154 | 0.0% | 0.0% | 100.0% | 0.0% | 0.0% | 5.1% |
| 1503401187 | Colorectal/Normal | | | 0 | 0 | 8,627 | 0 | 0 | 0 | 0.0% | 0.0% | 100.0% | 0.0% | 0.0% | 0.0% |
| 1503401188 | Bile duct | | | 0 | 0 | 929 | 0 | 0 | 21 | 0.0% | 0.0% | 100.0% | 0.0% | 0.0% | 2.2% |
| 1503401189 | Colorectal/Normal | | | 0 | 0 | 606 | 0 | 0 | 0 | 0.0% | 0.0% | 100.0% | 0.0% | 0.0% | 0.0% |
| 1503401190 | Colorectal/Normal | | | 0 | 0 | 1,659 | 0 | 0 | 4 | 0.0% | 0.0% | 100.0% | 0.0% | 0.0% | 0.3% |
| 1503401191 | Colorectal/Normal | Adenocarcinoma | grade 3/moderate | 13,862 | 0 | 6,782 | 17,430 | 4,635 | 19,018 | 204.4% | 0.0% | 100.0% | 257.0% | 68.3% | 280.4% |
| 1503401192 | Colorectal/Normal | | | 0 | 0 | 695 | 0 | 0 | 21 | 0.0% | 0.0% | 100.0% | 0.0% | 0.0% | 3.0% |
| 1503401193 | Colorectal/Normal | Other | U | 46,219 | 17,329 | 26,613 | 57,917 | 7,921 | 58,169 | 173.7% | 65.1% | 100.0% | 217.6% | 29.8% | 218.6% |
| 1503401194 | Colorectal/Normal | Squamous Cell | grade 3/moderate | 33,593 | 16,483 | 13,425 | 240 | 3,444 | 51,199 | 250.2% | 122.8% | 100.0% | 1.8% | 25.7% | 381.4% |
| 1503401195 | Colorectal/Normal | Adenocarcinoma | U | 2,137 | 1,377 | 6,043 | 3,300 | 354 | 5,665 | 35.4% | 22.8% | 100.0% | 54.6% | 5.9% | 93.7% |
| 1503401196 | Stomach | Adenocarcinoma | grade 3/moderate | 27 | 119 | 561 | 218 | 62 | 347 | 4.9% | 21.2% | 100.0% | 38.9% | 11.1% | 61.9% |
| 1503401197 | Colorectal/Normal | Adenocarcinoma | grade 3/moderate | 474 | 0 | 1,556 | 1,093 | 33 | 2,233 | 30.5% | 0.0% | 100.0% | 70.2% | 2.1% | 143.5% |
| 1503401198 | Colorectal/Normal | Adenocarcinoma | grade 4/poorly | 28 | 451 | 4,264 | 110 | 0 | 857 | 0.7% | 10.6% | 100.0% | 2.6% | 0.0% | 20.1% |
| 1507705066 | Stomach | Adenocarcinoma | grade 4/poorly | 0 | 0 | 1,755 | 0 | 0 | 22 | 0.0% | 0.0% | 100.0% | 0.0% | 0.0% | 1.3% |
| 1507705067 | Stomach | Adenocarcinoma | grade 4/poorly | 0 | 0 | 1,965 | 0 | 0 | 42 | 0.0% | 0.0% | 100.0% | 0.0% | 0.0% | 2.1% |
| 1507705068 | Colorectal/Normal | | | 0 | 0 | 4,406 | 0 | 0 | 0 | 0.0% | 0.0% | 100.0% | 0.0% | 0.0% | 0.0% |
| 1507705070 | Colorectal/Normal | Adenocarcinoma | grade 4/poorly | 10,618 | 647 | 12,943 | 15,040 | 2,671 | 15,743 | 82.0% | 5.0% | 100.0% | 116.2% | 20.6% | 121.6% |

FIG. 10F

| SampleID | final Site Category | Histology, Cancer | grade | Multiplex PreAmp + PCR Flap Assay Strands/rxn | | | | | | %Methylation | | | | | |
|---|---|---|---|---|---|---|---|---|---|---|---|---|---|---|---|
| | | | | NDRG4 | BMP3 | BTACT | VAV3 | S897 | ZDHHC1 | NDRG4 | BMP3 | BTACT | VAV3 | S897 | ZDHHC1 |
| 1507705071 | Colorectal/Normal | | | 0 | 0 | 1,622 | 0 | 0 | 19 | 0.0% | 0.0% | 100.0% | 0.0% | 0.0% | 1.1% |
| 1507705072 | Colorectal/Normal | | | 0 | 0 | 5,291 | 0 | 0 | 183 | 0.0% | 0.0% | 100.0% | 0.0% | 0.0% | 3.5% |
| 1507705073 | Colorectal/Normal | Adenocarcinoma | grade 3/moderate | 42 | 0 | 3,370 | 0 | 32 | 291 | 1.2% | 0.0% | 100.0% | 0.0% | 1.0% | 8.6% |
| 1507705074 | Stomach | Adenocarcinoma | grade 4/poorly | 0 | 6 | 1,076 | 101 | 0 | 198 | 0.0% | 0.5% | 100.0% | 9.4% | 0.0% | 18.4% |
| 1507705075 | Colorectal/Normal | Adenocarcinoma | grade 3/moderate | 49 | 0 | 2,257 | 0 | 15 | 443 | 2.2% | 0.0% | 100.0% | 0.0% | 0.7% | 19.6% |
| 1507705076 | Colorectal/Normal | | | 0 | 0 | 1,614 | 0 | 0 | 0 | 0.0% | 0.0% | 100.0% | 0.0% | 0.0% | 0.0% |
| 1507705077 | Stomach | Adenocarcinoma | grade 4/poorly | 0 | 0 | 2,391 | 0 | 0 | 0 | 0.0% | 0.0% | 100.0% | 0.0% | 0.0% | 0.0% |
| 1507705078 | Stomach | Adenocarcinoma | grade 4/poorly | 0 | 0 | 3,512 | 0 | 0 | 6 | 0.0% | 0.0% | 100.0% | 0.0% | 0.0% | 0.2% |
| 1507705079 | Stomach | Adenocarcinoma | grade 4/poorly | 0 | 0 | 6,760 | 0 | 0 | 0 | 0.0% | 0.0% | 100.0% | 0.0% | 0.0% | 0.0% |
| 1507705080 | Stomach | Adenocarcinoma | grade 4/poorly | 0 | 21 | 996 | 0 | 0 | 22 | 0.0% | 2.1% | 100.0% | 0.0% | 0.0% | 2.2% |
| 1507705081 | Stomach | | | 0 | 0 | 2,582 | 0 | 0 | 0 | 0.0% | 0.0% | 100.0% | 0.0% | 0.0% | 0.0% |
| 1507705082 | Stomach | Adenocarcinoma | grade 4/poorly | 0 | 0 | 1,494 | 0 | 0 | 29 | 0.0% | 0.0% | 100.0% | 0.0% | 0.0% | 1.9% |
| 1507705083 | Stomach | Adenocarcinoma | grade 3/moderate | 2 | 25 | 3,752 | 26 | 0 | 69 | 0.1% | 0.7% | 100.0% | 0.7% | 0.0% | 1.8% |
| 1507705084 | Colorectal/Normal | | | 0 | 0 | 2,562 | 0 | 0 | 67 | 0.0% | 0.0% | 100.0% | 0.0% | 0.0% | 2.6% |
| 1507705085 | Stomach | Adenocarcinoma | grade 4/poorly | 0 | 7 | 3,533 | 0 | 0 | 0 | 0.0% | 0.2% | 100.0% | 0.0% | 0.0% | 0.0% |
| 1507705086 | Colorectal/Normal | | | 0 | 0 | 2,289 | 0 | 0 | 15 | 0.0% | 0.0% | 100.0% | 0.0% | 0.0% | 0.7% |
| 1507705087 | Stomach | Adenocarcinoma | grade 4/poorly | 0 | 0 | 2,005 | 0 | 0 | 71 | 0.0% | 0.0% | 100.0% | 0.0% | 0.0% | 3.5% |
| 1507705088 | Colorectal/Normal | | | 0 | 0 | 345 | 0 | 0 | 3 | 0.0% | 0.0% | 100.0% | 0.0% | 0.0% | 0.9% |
| 1508204660 | Other | | | 0 | 0 | 1,285 | 0 | 0 | 294 | 0.0% | 0.0% | 100.0% | 0.0% | 0.0% | 22.9% |
| 1508204661 | Colorectal/Normal | Adenocarcinoma | | 0 | 5 | 35,774 | 0 | 0 | 664 | 0.0% | 0.0% | 100.0% | 0.0% | 0.0% | 1.9% |
| 1508204662 | Colorectal/Normal | Adenocarcinoma | grade 2/well | 0 | 9 | 1,086 | 0 | 0 | 56 | 0.0% | 0.8% | 100.0% | 0.0% | 0.0% | 5.2% |
| 1508204663 | Stomach | Adenocarcinoma | U | 0 | 0 | 2,169 | 0 | 0 | 0 | 0.0% | 0.0% | 100.0% | 0.0% | 0.0% | 0.0% |
| 1508204664 | Stomach | Adenocarcinoma | grade 3/moderate | 0 | 0 | 1,918 | 0 | 0 | 72 | 0.0% | 0.0% | 100.0% | 0.0% | 0.0% | 3.8% |
| 1508204665 | Stomach | Adenocarcinoma | grade 4/poorly | 0 | 0 | 3,412 | 0 | 0 | 95 | 0.0% | 0.0% | 100.0% | 0.0% | 0.0% | 2.8% |
| 1508204666 | Colorectal/Normal | Adenocarcinoma | grade 3/moderate | 5,015 | 7,235 | 20,993 | 16,773 | 3,667 | 34,878 | 23.9% | 34.5% | 100.0% | 79.9% | 17.5% | 166.1% |

FIG. 10G

Direct Flap Assay (NO Pre-Amp)

| SampleID | NDRG4 | BMP3 | BTACT | VAV3 | S897 | ZDHHC1 |
|---|---|---|---|---|---|---|
| 1503401149 | 0 | 41 | 15,388 | 0 | 0 | 10 |
| 1503401151 | 11 | 4 | 148 | 9 | 3 | 8 |
| 1503401152 | 0 | 4 | 47 | 5 | 1 | 20 |
| 1503401153 | 0 | 0 | 110 | 0 | 0 | 0 |
| 1503401154 | 0 | 0 | 46 | 0 | 0 | 0 |
| 1503401156 | 0 | 0 | 161 | 0 | 0 | 2 |
| 1503401157 | 0 | 0 | 1,897 | 0 | 0 | 397 |
| 1503401158 | 3,551 | 1,636 | 4,691 | 3,705 | 829 | 3,109 |
| 1503401160 | 15 | 5 | 721 | 8 | 2 | 9 |
| 1503401161 | 932 | 334 | 1,525 | 389 | 307 | 924 |
| 1503401162 | 0 | 310 | 3,367 | 2,036 | 0 | 3,624 |
| 1503401163 | 0 | 0 | 80 | 0 | 0 | 25 |
| 1503401164 | 0 | 2 | 65 | 0 | 0 | 0 |
| 1503401165 | 0 | 0 | 106 | 0 | 0 | 0 |
| 1503401166 | 0 | 0 | 178 | 0 | 0 | 8 |
| 1503401167 | 1,732 | 0 | 3,661 | 1,277 | 408 | 1,980 |
| 1503401168 | 0 | 0 | 125 | 0 | 0 | 26 |
| 1503401169 | 0 | 0 | 175 | 0 | 0 | 4 |
| 1503401170 | 0 | 0 | 131 | 0 | 0 | 0 |
| 1503401171 | 0 | 0 | 125 | 0 | 0 | 2 |
| 1503401172 | 65 | 66 | 413 | 102 | 6 | 176 |
| 1503401173 | 0 | 0 | 357 | 0 | 1 | 30 |
| 1503401175 | 0 | 0 | 132 | 0 | 0 | 2 |
| 1503401176 | 0 | 0 | 100 | 0 | 0 | 2 |
| 1503401177 | 0 | 0 | 119 | 0 | 0 | 0 |
| 1503401178 | 4 | 9 | 25,397 | 0 | 0 | 6 |
| 1503401179 | 0 | 1 | 116 | 1 | 0 | 3 |
| 1503401180 | 0 | 0 | 61 | 2 | 0 | 2 |

%Recovery (compared to Direct Flap Assay)

| SampleID | NDRG4 | BMP3 | BTACT | VAV3 | S897 | ZDHHC1 |
|---|---|---|---|---|---|---|
| 1503401149 | 9% | 103% | 38% | - | - | 204% |
| 1503401151 | - | 97% | 44% | 10% | 17% | 80% |
| 1503401152 | - | 121% | 39% | 43% | 55% | 112% |
| 1503401153 | - | - | 71% | - | - | - |
| 1503401154 | - | - | 94% | - | - | - |
| 1503401156 | - | - | 57% | - | - | 0% |
| 1503401157 | - | - | 32% | - | - | 131% |
| 1503401158 | 172% | 217% | 118% | 168% | 128% | 197% |
| 1503401160 | 8% | 5% | 28% | 79% | 9% | 81% |
| 1503401161 | 91% | 190% | 68% | 122% | 83% | 152% |
| 1503401162 | - | 233% | 68% | 158% | 84% | 183% |
| 1503401163 | - | - | 83% | - | - | 94% |
| 1503401164 | - | - | 120% | - | - | - |
| 1503401165 | - | - | 419% | - | - | - |
| 1503401166 | - | - | 161% | - | - | 80% |
| 1503401167 | 170% | - | 137% | 268% | 197% | 212% |
| 1503401168 | - | - | 37% | - | 132% | 122% |
| 1503401169 | - | - | 55% | - | - | 87% |
| 1503401170 | - | - | 74% | - | - | - |
| 1503401171 | - | - | 56% | - | - | - |
| 1503401172 | 44% | 165% | 69% | 113% | 93% | 131% |
| 1503401173 | - | - | 42% | - | 121% | 140% |
| 1503401175 | - | - | 115% | - | - | 66% |
| 1503401176 | - | - | 42% | - | - | 26% |
| 1503401177 | - | - | 54% | - | - | - |
| 1503401178 | - | 18% | 44% | 304% | - | 40% |
| 1503401179 | - | - | 113% | 2% | - | 0% |
| 1503401180 | - | - | 86% | - | 0% | 254% |

Input strands calculated from Multiplex + PCR Flap assay

| SampleID | NDRG4 | BMP3 | BTACT | VAV3 | S897 | ZDHHC1 |
|---|---|---|---|---|---|---|
| 1503401149 | 0 | 42 | 5821 | 0 | 0 | 20 |
| 1503401151 | 1 | 4 | 66 | 1 | 1 | 6 |
| 1503401152 | 0 | 5 | 19 | 2 | 0 | 23 |
| 1503401153 | 0 | 0 | 78 | 0 | 0 | 2 |
| 1503401154 | 0 | 0 | 44 | 0 | 0 | 0 |
| 1503401156 | 0 | 0 | 91 | 0 | 0 | 0 |
| 1503401157 | 0 | 0 | 610 | 0 | 0 | 521 |
| 1503401158 | 6109 | 3549 | 5547 | 6229 | 1061 | 6122 |
| 1503401160 | 1 | 0 | 203 | 6 | 0 | 7 |
| 1503401161 | 850 | 634 | 1040 | 476 | 255 | 1401 |
| 1503401162 | 0 | 723 | 2280 | 3226 | 0 | 6619 |
| 1503401163 | 0 | 0 | 67 | 0 | 0 | 24 |
| 1503401164 | 0 | 0 | 78 | 0 | 0 | 2 |
| 1503401165 | 0 | 0 | 444 | 0 | 0 | 0 |
| 1503401166 | 0 | 0 | 287 | 0 | 0 | 6 |
| 1503401167 | 2945 | 0 | 5014 | 3421 | 804 | 4202 |
| 1503401168 | 0 | 0 | 46 | 0 | 0 | 32 |
| 1503401169 | 0 | 0 | 97 | 0 | 0 | 3 |
| 1503401170 | 0 | 0 | 97 | 1 | 0 | 1 |
| 1503401171 | 0 | 0 | 69 | 0 | 0 | 0 |
| 1503401172 | 28 | 108 | 284 | 116 | 5 | 231 |
| 1503401173 | 0 | 0 | 151 | 0 | 2 | 42 |
| 1503401175 | 0 | 0 | 151 | 0 | 0 | 1 |
| 1503401176 | 0 | 0 | 42 | 0 | 0 | 1 |
| 1503401177 | 0 | 0 | 64 | 0 | 0 | 0 |
| 1503401178 | 0 | 2 | 11164 | 2 | 0 | 2 |
| 1503401179 | 0 | 0 | 131 | 2 | 0 | 0 |
| 1503401180 | 0 | 0 | 53 | 0 | 0 | 5 |

FIG. 10H

Direct Flap Assay (NO Pre-Amp)

| SampleID | NDRG4 | BMP3 | BTACT | VAV3 | S897 | ZDHHC1 |
|---|---|---|---|---|---|---|
| 1503401181 | 0 | 0 | 213 | 0 | 0 | 0 |
| 1503401182 | 19 | 1 | 155 | 10 | 1 | 19 |
| 1503401183 | 0 | 0 | 105 | 0 | 0 | 1 |
| 1503401184 | 0 | 0 | 90 | 0 | 0 | 3 |
| 1503401185 | 0 | 0 | 86 | 0 | 0 | 4 |
| 1503401186 | 0 | 2 | 234 | 0 | 0 | 3 |
| 1503401187 | 0 | 0 | 368 | 0 | 0 | 1 |
| 1503401188 | 0 | 0 | 126 | 0 | 0 | 4 |
| 1503401189 | 0 | 0 | 57 | 0 | 0 | 0 |
| 1503401190 | 0 | 0 | 71 | 0 | 0 | 0 |
| 1503401191 | 469 | 0 | 943 | 574 | 213 | 502 |
| 1503401192 | 0 | 0 | 64 | 0 | 0 | 0 |
| 1503401193 | 1,829 | 480 | 2,239 | 2,271 | 421 | 1,939 |
| 1503401194 | 1,180 | 324 | 1,909 | 13 | 183 | 1,922 |
| 1503401195 | 179 | 44 | 562 | 148 | 43 | 244 |
| 1503401196 | 9 | 3 | 46 | 2 | 0 | 8 |
| 1503401197 | 23 | 0 | 96 | 21 | 2 | 37 |
| 1503401198 | 16 | 9 | 125 | 5 | 0 | 17 |
| 1507705066 | 0 | 0 | 82 | 0 | 0 | 0 |
| 1507705067 | 0 | 0 | 118 | 0 | 0 | 2 |
| 1507705068 | 0 | 19 | 100 | 0 | 0 | 0 |
| 1507705070 | 262 | 19 | 713 | 475 | 103 | 406 |

%Recovery (compared to Direct Flap Assay)

| SampleID | NDRG4 | BMP3 | BTACT | VAV3 | S897 | ZDHHC1 |
|---|---|---|---|---|---|---|
| 1503401181 | - | - | 370% | - | - | - |
| 1503401182 | 20% | 157% | 88% | 180% | 0% | 181% |
| 1503401183 | - | - | 64% | - | - | 171% |
| 1503401184 | - | - | 108% | - | - | 30% |
| 1503401185 | - | - | 125% | - | - | 49% |
| 1503401186 | - | - | 63% | - | - | 287% |
| 1503401187 | - | - | 115% | - | - | 0% |
| 1503401188 | - | - | 36% | - | - | 25% |
| 1503401189 | - | - | 52% | - | - | - |
| 1503401190 | - | - | 113% | - | - | - |
| 1503401191 | 144% | - | 35% | 148% | 106% | 185% |
| 1503401192 | - | - | 53% | - | - | 228% |
| 1503401193 | 123% | 176% | 58% | 125% | 92% | 146% |
| 1503401194 | 139% | 249% | 34% | 87% | 92% | 130% |
| 1503401195 | 58% | 153% | 53% | 109% | 40% | 114% |
| 1503401196 | 15% | 224% | 60% | 641% | 31005% | 209% |
| 1503401197 | 103% | - | 79% | 259% | 86% | 296% |
| 1503401198 | 8% | 254% | 166% | 106% | 158% | 246% |
| 1507705066 | - | - | 104% | - | - | - |
| 1507705067 | - | - | 81% | - | - | 106% |
| 1507705068 | - | - | 215% | - | - | - |
| 1507705070 | 198% | 163% | 89% | 155% | 126% | 189% |

Input strands calculated from Multiplex + PCR Flap assay

| SampleID | NDRG4 | BMP3 | BTACT | VAV3 | S897 | ZDHHC1 |
|---|---|---|---|---|---|---|
| 1503401181 | 0 | 0 | 788 | 0 | 0 | 0 |
| 1503401182 | 4 | 2 | 137 | 18 | 0 | 34 |
| 1503401183 | 0 | 0 | 67 | 0 | 0 | 3 |
| 1503401184 | 0 | 0 | 97 | 0 | 0 | 1 |
| 1503401185 | 0 | 0 | 108 | 0 | 0 | 2 |
| 1503401186 | 0 | 0 | 147 | 0 | 0 | 8 |
| 1503401187 | 0 | 0 | 421 | 0 | 0 | 0 |
| 1503401188 | 0 | 0 | 45 | 0 | 0 | 1 |
| 1503401189 | 0 | 0 | 30 | 0 | 0 | 0 |
| 1503401190 | 0 | 0 | 81 | 0 | 0 | 0 |
| 1503401191 | 677 | 0 | 331 | 851 | 226 | 929 |
| 1503401192 | 0 | 0 | 34 | 0 | 0 | 1 |
| 1503401193 | 2257 | 846 | 1299 | 2828 | 387 | 2840 |
| 1503401194 | 1640 | 805 | 655 | 12 | 168 | 2500 |
| 1503401195 | 104 | 67 | 295 | 161 | 17 | 277 |
| 1503401196 | 1 | 6 | 27 | 11 | 3 | 17 |
| 1503401197 | 23 | 0 | 76 | 53 | 2 | 109 |
| 1503401198 | 1 | 22 | 208 | 5 | 0 | 42 |
| 1507705066 | 0 | 0 | 86 | 0 | 0 | 1 |
| 1507705067 | 0 | 0 | 96 | 0 | 0 | 2 |
| 1507705068 | 0 | 0 | 215 | 0 | 0 | 0 |
| 1507705070 | 518 | 32 | 632 | 734 | 130 | 769 |

FIG. 10I

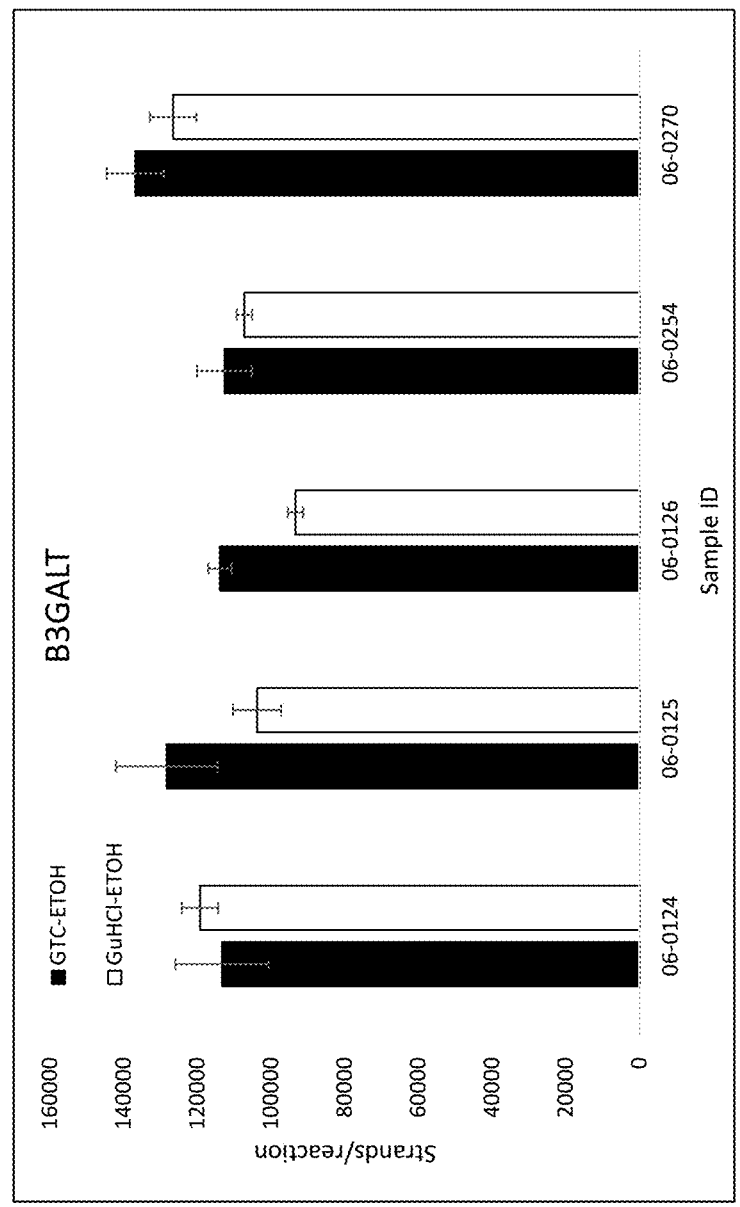

| | Description | Sequence (all are shown 5' to 3') |
|---|---|---|
| SEQ ID NO:1 | SFMBT2 Target DNA | AAGGGCTGCTCTCCGGCCAGCTGCTGGGCGCCGGGGACAGCAGCCGGCGCGGGCGTCCTCCTACCTGGTGAAGTTGTCCTGCCCTCG GCGTGGACCCAGCCCCGGTCGCCGCCCGCCCCGCTCGCCGCTCGCTCCGGCCACCGCACCCTTGCCCGCTCGCTC CCGCCCGCCGCTCCCCCTGGAACCCAGCCCGCTCCCGCTCCGGTCGCCGGGAGGGCACCGGCTCTCCGGCTCTCCCACTACAGCTCAT |
| SEQ ID NO:2 | SFMBT2 Target region FIG. 5 | TGCCCTCGGGCGTGGACCCAGCCCCGGTCGCCGCCCGCCCCGCTCGCCGCTCGCTCCGGCCACCGCACCCTTGCCCGCTCGCTCCTCG GCTCGCTCCCCCGCCCGCCGCTCCCCCTGGAACCCAGCCCGCTCCCGCTCCGGTCCTCCG |
| SEQ ID NO:3 | SFMBT2 Bisulfite converted DNA | AAGGGTTGTTTTCGGTTAGTTTGGGCGTCGGGGATAGTAGTCGGCGCGGGCGTTTATTGTGAAGTTCGTTGTTTTCGGC GTGGATTTAGTTTCGTTCGTCGTTCGCGCGGGCGTTCGTTTTATTATAGTTTAT TCGTCGTTTTCGCGCGTTCGTTCGGGATTTAGGTTCGTTCGGGAGGGTATCGGTTCGTTCGTTTTGTTTATTATAGTTTAT |
| SEQ ID NO:4 | SFMBT2 Bisulfite converted region FIG. 5 | TGTTTTCGGCGTGGATTTAGTTTCGTTCGTCGTTCGCGCGGGCGTTCGTTTTATTATAGTTTAT TCGTTTTTCGTTCGTCGTTGGATTTAGG |
| SEQ ID NO:5 | SFMBT2 Outer Forward Primer | TGTTTTCGGCGTGGATTTAGG |
| SEQ ID NO:6 | SFMBT2 Outer Reverse Primer | CGAAAACCGAAACGAACGC |
| SEQ ID NO:7 | SFMBT2 PCR/Flap assay target region | GTCGTCGTTCGGGAGGGTATCGGTTTCGTTCGTTCGTTTTGTTCG |
| SEQ ID NO:8 | SFMBT2 PCR/Flap assay Forward Primer | GTCGTCGTTCGAGAGGGTA |
| SEQ ID NO:9 | SFMBT2 PCR/Flap assay Reverse Primer | CGAACAAAACGAACGAACGAA |
| SEQ ID NO:10 | SFMBT2 Flap oligonucleotide | CCACGACGATCGGTTTCGTT |
| SEQ ID NO:11 | VAV3 Target DNA | CGGCCGGGGCGCACGGGAGAGCGCGCTGCAGCGGGACTCGCTGCAGCGGCCCGTCGCTGCAGCCGCACCCGGGCGCGGCCACCCGGAGCC GAGCCTAGCTGGGCGCGCGGAGGAACC GCGTCGGGGACTCGCTGCAGCGGCCGGCCGGGGACTCGCAGCCGCACCCGGGCGCGGCCACCCGGGAAAGGCCGGCGGCTGTTGGC |
| SEQ ID NO:12 | VAV3 Target region FIG. 5 | CGACCCGTCGGGGACTCGCTGCAGCGGCCGGCCGGATTCGTTGTAGCGGGATCGTTGTGATCCGGGGAAAGGCCGGCGGATCGGAGTCC |
| SEQ ID NO:13 | VAV3 Bisulfite converted DNA | CGGTTCGGGGCGTACGGGAGAGCGCGGGATTCGTTGTAGCGGGATCGTTGTGATCCGGGGCGGGGTATTCGGTCGGATCGGAGTCG AGTTTAGCGCGGCGGTTCGTTCGCGATTCGTTCGGGATTCGTTGTTTTTGTTTTTCGATTTCGCCGCGGTCGGGGATCGAGTTTAGCGGGTTGTTGGC GTCGGGGCGGGGCGCGGAGGAATT |
| SEQ ID NO:14 | VAV3 Bisulfite converted region FIG. 5 | GCGCGCGGGGATTCGTTGTAGCGGGCGGTTTTTTTGTTTTTTCGATTCGCCGCGGTCGGGGATCGAGTTTAGCGGCGTTCGC |
| SEQ ID NO:15 | VAV3 Outer Forward Primer | CGCGGGATTCGTTGTAGC |

FIG. 13A

| | Description | Sequence (all are shown 5' to 3') |
|---|---|---|
| SEQ ID NO:16 | VAV3 Outer Reverse Primer | CAACCGCCGACCCTTC |
| SEQ ID NO:17 | VAV3 PCR/Flap assay target region | TCGGAGTCGAGTTTAGCGCGGCGTTCGCGATTCGTTAGTCGCGGGTTTTGTT |
| SEQ ID NO:18 | VAV3 PCR/Flap assay Forward Primer | TCGGAGTCGAGTTTAGCGC |
| SEQ ID NO:19 | VAV3 PCR/Flap assay Reverse Primer | AACAAAAACCGCGACTAACGA |
| SEQ ID NO:20 | VAV3 Flap oligonucleotide | CCACGGACGCGGCGTTCGCGA/3C6/ |
| SEQ ID NO:21 | BMP3 Target DNA | CTGGGTCAGCGACGCAGCAAGTGGGGCTGGCGCTATCTCGCTGCACCGGCTCCGTGCCGCCCTGCCCCAGC<br>TGGTTTGGAGTTCAACCCTCGGCTCCGCCGCGCCCTTGCGCCTTCGGAGTGTCCGCAGGACGCCGGGAGCCGACGCGC<br>CGCGCGGGGTACCTAGCCATGGCCATGGGGCGAGCAGGCTGCTCTT |
| SEQ ID NO:22 | BMP3 Target region FIG. 5 | GGGCTCCGTGCGCCCTCGCCCCAGCTGGTTTGGAGTTCAACCCTCGGCTCCGCCGCGCCCTTGCGCCTTCGGAGTGTCCC<br>GCAGGACGACGCCGGGAGCCGACGCGCCGCGCGGGGTACCTAGCCATGGCCATGGGGCGA |
| SEQ ID NO:23 | BMP3 Bisulfite converted DNA | TTGGGTTAGCGTAGTAAGTGGGTTCGTCGTCGTCGTTTGGAGTTAATTTCGTGTATTCGTTGGGTTCGTCGGTTTCGTTTAGTTC<br>GTTTGGAGTATTTAGTTATGGTTGGGGCGAGTAGGTTGTTTT<br>GCGGGTATTTAGTTATGGTTGGGGCGAGTAGGTTGTTTT |
| SEQ ID NO:24 | BMP3 Bisulfite converted region FIG. 5 | CGGGTTTCGTGCGTTTCGTCGTTTTAGTTGTTCGGAGTTAATTTCGGTTCGTCGTCGGTTTTTTGCGTTTTTCGGAGTGTTTCGT<br>AGCGACGTCGGGAGTCGACGCGTCGACGCGTCGACGTCGACGTCGGGGGGA |
| SEQ ID NO:25 | BMP3 Outer Forward Primer | GGTTTCGTGCGTTTTCGTTTAGT |
| SEQ ID NO:26 | BMP3 Outer Reverse Primer | CCAACCATAACTAAATACCGCG |
| SEQ ID NO:27 | BMP3 PCR/Flap assay target region | GTTTAATTTTCGGTTCGTCGTCGGTTTTTTGCGTTTTTCGGAGTGTTTCGTAGCG |
| SEQ ID NO:28 | BMP3 PCR/Flap assay Forward Primer | GTTTAATTTTCGGTTCGTCGTC |
| SEQ ID NO:29 | BMP3 PCR/Flap assay Reverse Primer | CGCTACGAAACACTCCGA |
| SEQ ID NO:30 | BMP3 Flap oligonucleotide | CGCCGAGGGCGGTTTTTGCG/3C6/ |

FIG. 13B

| | Description | Sequence (all are shown 5' to 3') |
|---|---|---|
| SEQ ID NO:31 | NDRG4 Target DNA | CGCAGCGCACCAGCAGACAGTCCGCGGCGGGAGCGGGTGAGAAGTCGGCGGGGGCGGATCGACCGGGTGTCCCCAG GCTCCGCGTCGCGGTCCGTCCCCGCTCGCCCCTCCCGCAGCCGCACCCCAGCCGCAGAAGGCGGAAGCCACGCGCGAG GGACCGCGGTTCGTCGGGACTAGCCCAGGCCCGGCCCCGGAGCGCCAC |
| SEQ ID NO:32 | NDRG4 Target region FIG. 5 | GACCGGGGGTGTCCCCCAGGCTCCGCGGCCGAGGGACCGCGGTC GCGGAAGCCACGCGCGAGGGACCGCGGTC CGTAGCGTATTTAGTATAGTCGCGCGGCGAGAGTCGGCGGGATCGATCGGGGTGTTTTTAGGT TTCGCGTCGCGGTTTTCGTTCGTTTTAGGTTCGGTATCGTTTCGCGGGTCGAGCGTTAT |
| SEQ ID NO:33 | NDRG4 Bisulfite converted DNA | CGCGGTTCGTTCGGGATTAGTTTAGGTTCGGTATCGTTTCGCGGGTCGAGCGTTAT |
| SEQ ID NO:34 | NDRG4 Bisulfite converted region FIG. 5 | GATCGGGGTGTTTTTAGGTTCGCGTCGCGTCGGTTTTCGTTATCGGGTATTTTAGTCGCGTAGAAGCCG GAAGTTACGCGCGAGGGATCGCGGTT |
| SEQ ID NO:35 | NDRG4 Outer Forward Primer | GGTGTTTTTAGGTTTCGCGTC |
| SEQ ID NO:36 | NDRG4 Outer Reverse Primer | GATCCCTCGCGCGTAAC |
| SEQ ID NO:37 | NDRG4 PCR/Flap assay target region | CGGTTTTCGTTCGTTTTTCGTTCGTTTATCGGGTATTTTAGTCGCGTAGAAGGCGG |
| SEQ ID NO:38 | NDRG4 PCR/Flap assay Forward Primer | CGGTTTTCGTTCGTTTTTCG |
| SEQ ID NO:39 | NDRG4 PCR/Flap assay Reverse Primer | CCGCCTTCTACGCGACTA |
| SEQ ID NO:40 | NDRG4 Flap oligonucleotide | CCACGGACG GTTCGTTTATCG/3C6/ |
| SEQ ID NO:41 | Beta Actin Target DNA | CTCTGACCTGAGTCTCCTTGGAACTCTGCAGGTTCTATTGCTTTTCCCAGATGAGCTCTTTTCTGGTGTTGTCTCTGAC TAGGTGTCTAAGACAGTGTTGTGGGTGTAAGAGTACTAACACTGGCTCGTGTGACAAGGCCATGAGGCTGGTGTAAAGCGGCCT TGGAGTGTGTATTAAGAGGTGCACAGTAGGTCTGAACAGACTCCCATCCCAAGA3' |
| SEQ ID NO:42 | Beta Actin Target region FIG. 5 | CTCTGCAGGTTCTATTGCTTTTCCCAGATGAGCTCTTTTCTGGTGTTGTCTCTGACTAGGTGTCTAAGACAGTGTTGTGG GTGTAGGTACTAACACTGGCTCGTGTGACAAGGCCATGAGGCTGGTGTAAAGCGGCCTTGGAGTGTGTATTAAGAGGTG |
| SEQ ID NO:43 | Beta Actin Bisulfite converted DNA | TTTTGATTTGAAGTTTTTATTTGTTTTTTTGGAATTTGTTATTGTTTTTAGAGTGAGTTTTTTTGTTGTTTTTTGATTA GGTGTTTAAGATAGTGTTGTGGGTGTAGGTATTAATATTGGTTTGTGTGATAAGGTTATGAGGTTGGTGTTTTGG AGTGTGTATTAAGAGTGTATAGTAGGTGTATAGTAGGTTGAATAGATTTTTATTTAAGA |
| SEQ ID NO:44 | Beta Actin Bisulfite converted region FIG. 5 | TTTTGTAGGTTTTATTTGTTTTTTTAGATGAGTTTTTTTGTTGTTTGTTTTTGATTAGGTGTTAAGATAGTGTTGTGGG TGTAGGTATTAATATTGGTTTGTGTGATAAGGTTATGAGGTTGGTGTAAAGTGGTGTATTAAGTAGGTG |
| SEQ ID NO:45 | Beta Actin Outer Forward Primer | TTGTAGGTTTTATTTGTTTTTTTAGATGAGTTT |

FIG. 13C

| | Description | Sequence (all are shown 5' to 3') |
|---|---|---|
| SEQ ID NO:46 | Beta Actin Outer Reverse Primer | CTACTTAATACACACTCCAAAACCACT |
| SEQ ID NO:47 | Beta Actin PCR/Flap assay target region | TTTGTTTTTTGATTAGGTGTTTAAGATAGTGTTGTGGGTGTAGGTATTAATATTGGTTGTGTGATAAGGTTATGAGGTTGGTG |
| SEQ ID NO:48 | Beta Actin PCR/Flap assay Forward Primer | TTTGTTTTTTGATTAGGTGTTTAAGA |
| SEQ ID NO:49 | Beta Actin PCR/Flap assay Reverse Primer | CACCAACCTCATAACCTTATC |
| SEQ ID NO:50 | Beta Actin Flap oligonucleotide | GACGCGGAG ATAGTGTTGTGG/3C6/ |
| SEQ ID NO:51 | ZDHHC1 Target DNA | CCGTGGACGAGAGATTCCAGTGGGCGAGACGCGCCTGGGCAGCGCCGCCGCCCCCGCGGGGCCAGGGCCGACAGCCCA<br>CGCTGGCGCGGCAGGCGCGTGCGCCCCGCCGTTTTCGTGAGCGCAGCAGCCCGAGCGAGGCGCCAGGGCGCCGGGCCGGGAG<br>GCTGGTCTGGCTTAGCTGG |
| SEQ ID NO:52 | ZDHHC1 Target region FIG. 5 | GGGCAGCGCCGCTCTGGCCGCCCCCGCGGGGCCGACAGCCCACGCTGGCGCGGCAGGCGCGTGCGCCCCGCCGTTTT<br>CGTGAGCCCGAGCAGCGGCGGCGCCAGGGCGCCGGGAGGCTGGTCTGGCTTAGCTGG |
| SEQ ID NO:53 | ZDHHC1 Bisulfite converted DNA | TCGTGGACGAGAGATTTTAGTGGCGTAGAGCGCGTTGGGTAGCGTCGTTTGGTCGTTCGCGGGGTCGATAGTTTACG<br>TTGGCGCGGTAGGCGCGTCGTTCGTTTTCGTGAGTAGCGGCGAGTTTAGGGCGTCGGTCGGAGGTTGGTTAGTTGG<br>GTTTGGTTAGTTGG |
| SEQ ID NO:54 | ZDHHC1 Bisulfite converted region FIG. 5 | GGGTAGCGTCGTTTGGTCGTTCGCGGGGTCGATAGTTTACGTTGGCGCGGTAGGCGCGTCGTTCGTTTTCG<br>TGAGTTCGAGTAGCGGCGAGTTTAGGGCGTCGGGCGTCGGGAGGTTGGTTGTTAGTTGG |
| SEQ ID NO:55 | ZDHHC1 Outer Forward Primer | AGCGTCGTTTGGTCGTTTC |
| SEQ ID NO:56 | ZDHHC1 Outer Reverse Primer | GACGCCCTAAACTCGCC |
| SEQ ID NO:57 | ZDHHC1 PCR/Flap assay target region | GTCGGGGTCGATAGTTTACGTTGGCGCGGTAGGCGCGTCGTCGTTTTCGTGAGTTCGAGT |
| SEQ ID NO:58 | ZDHHC1 PCR/Flap assay Forward Primer | GTCGGGGTCGATAGTTTACG |
| SEQ ID NO:59 | ZDHHC1 PCR/Flap assay Reverse Primer | ACTCGAAACTCACGAAAACG |
| SEQ ID NO:60 | ZDHHC1 Flap oligonucleotide | GACGCGGAGGACGAACGCACG/3C6/ |

FIG. 13D

| | Description | Sequence (all are shown 5' to 3') |
|---|---|---|
| SEQ ID NO:61 | Danio rerio Ras association (RalGDS/AF-6) domain family 1 (rassf1) | tcagcaaatgaagtctgctctcgttcgtctcctcaaagtaggacagatgccgattaagcgttaatctgagtcttctgcgcatgcgcatgaacgcgcgctacaag cggacaaggtgcgcgttcgaagaagaaacgaaccgagccgagccggttcgaagacaacgcggttcgagacaacgcgaatgaagcccacggaggacccgaaacctgaggaattcatcttct gccaggcggaggactgttttcagttttagtttgagctgataaggaagatgtttgggcacttttgccaatccctcatgttatcgcctcacagacacgcgtcgcgcgcag attacgcttaattgacggattgagcggattggaagaaacagacgcgttactgtcagtcgaggctcactcgtcagtgaggctcgtcagtggctcgtcagtcgtgttgggtttaagattgaccagatgct actgaaaactgtcaatcaagaagaaggaaacttgaagcaataaaacatcattctgtatatgaagactgtcagatcacacagtgatccatgtttggatatgcaa acaatcagaaacgagacgctaaatttatcagcttgcttttggagtaaacagcgttgcttaaaacactccacagtcataatcatctccagcctaacatggtccactg agccatgccgttcatcctccacgatcccaaaatgcaaatgcaaaatgtgagctcatgagttgcaggactggaggactgcaggactgactccgaatgagtttgactccgaatgagtcacccctagtgtcc ctccaccaccctggtgtccactgtggacactgtggacagcctgctgcgccgccatgcaccagatccgcgcatcatggcagcgcctgcctggaggaccccgattggctgacgtgaa accaggacgaggaggacatgactgtcagcctgcgcagcagacacagagtcgacactgtctgtggagagtttcatctggcctgtgacagacgagagcctccgctgca cacactgtaactacactgtgtcactaccgctgtcaaccctttcatttcagctgacttgactgcagtccacaatctgccacactacagcgcacactgtcactgtctgcactgaacaatcaaactacagcgaggacacca tcgacagacaccaatgtgatgagcagtcgaaggtgctgaggaaacaggatctgtctcactgaaatcagcagaagtgaaggaatacaatcagcagg tcaacagtaacctcttcatggttctgaatgtgacggcctcataaaacatctgctcatcatcaagtgcaaagctcagtttaagctgagcgcaccctcgtgctcttcctccctcccgcagcgtct cctcctccacctctccctcgttttaggatggatggcggctgccgtcaggagcgaacttccttctacctgccccagagacacagtcaagcacctgcaccctgcaccaatcaagtccgccaag cacgtgccagagaggtcatcaggccctgctcaacaagtcactgttggacaatccggctaaatattcctgtatgagcgcagccagggacaatcaagtgt acttaaggaagttagctgcttgtgatgatgatgtcacttttcctgaactcacttttcctgaactcagaactccagcagcactgactgcggaccaatgaggaagaagtccgagttttagtgtgttagtccgcaaatcatacgccgatacactctggctc tgaattggatgcgtcagttttcgaactcagaactcgaactcgaactctgtaagaactcagcagcctgctgaatgaatgtgttatacctcacaaacagagagatcgaggaggaaaacaaggcttatta gtgataagatgaaagaggctatgaagaacttcagcaagcgcctttgctcttacctgtgactgtgacataatgaggttgaagtgaaatgcagtgagcgagagaagaaatgcgtgtttgaa cgtctgagctaaagagtgtgtggtgacttcacactggagtcgtgtgacttgcgctcgtagccgttgagaggcagaagaaaagaaatgcgtgatcaaatgaataaatcaggcacatctagatgaaatgtcttctgtggagaatctatatatcagtcagattac gcatggctgttgagtgtgacttcacactggatgttttgttgtgctcaattattcgaattattcgaattaacgaggattatttaacgaggattatttataatcgtatcaaatgccacctgttagtgcaccacagtaacttgtcatatttga agctcccatgtatatatttggatgttttgttgtcaattattcgaattattcgaattcctttaaaatga |
| SEQ ID NO:62 | Untreated Danio RASSF1 target (Fig. 1) | ATCAGAACGAGACGCTAAATTTATCAGCTTGCTTTGGAGTAAACACTCCACAGTCATAAATCATCTCC AGCCCTAACCATGGTCCACTGAGCCATGCCGTTCATCCTCCACGATCCACACCAAAATGGCAAAATGTGAGCTCATCGAGTTGCAG GACTTGACTCCGAATGACCGTATTGAGCTGCACATCCTGCCATTGAGCTGCACGCTGATCCCTCCACCACCTGGTGCCCACTCTGACAGGTGGAG CAGAGGGAAGGTTGGTGCGCATGGTGGGCGAGCGCCTGCGCCCTGGAGGACCCCGATTGGCTGACGTGTAAACCAGGACGAG GACATGACTTTCAGCCCTGCAGCCAGACACAGTCGAGCTGGTGTGACCTGGTGACCTGTGACCTGTGTGGAGAGTTCATCTGGGCCTGTACAGACAG AGCCTCC |

FIG. 13E

| | Description | Sequence (all are shown 5' to 3') |
|---|---|---|
| SEQ ID NO:63 | Bisulfite-treated Danio RASSF1 target (Fig. 1) | ATTAGAACGAGACGTTAAATTATTAGTTTGTTTGGAGTAAATAGCGTTGTTTAAAATATTTTATAGTTATAAATTATTTTAG TTTTAATTATGGTTATTGAGTTATGTCGTTTATTTTTACGATTTTAAAATGTAAAATGTGAGTTTATCGAGTTGTAGGATTT GATTTCGAATGATCGTATTGAGTTGAGTTTGGTATTTTAGTGTTTTTTATCGTGTTTATTTGGATAGGTGGAGTAGAGGG AAGGTGGTGCGTATGGTGGGCGAGCGCGT:GCGTTGGAGATTCGATTGGTGACGTGAAATTAGGACGAGGATATGATT TTAGTTTTGTAGTTAGATATAGTTGAGTTGTGTGATTTGTGGAGAGTTTATTGGGGTTTGTATAGAGTTTC |
| SEQ ID NO:64 | ZF_RASSF1 UT forward primer | CGCATGGTGGGCGAG |
| SEQ ID NO:65 | Zebrafish RASSF1 UT reverse primer | ACACGTCAGCCAATCGGG |
| SEQ ID NO:66 | Zebrafish RASSF1 UT Probe (Arm 3) | GACGCGAGGCGCGTGCGCC/3C6/ |
| SEQ ID NO:67 | Zebrafish RASSF1 BT forward primer | TGCGTATGGTGGGCGAG |
| SEQ ID NO:68 | Zebrafish RASSF1 BT reverse primer | CCTAATTTACACGTCAACCAATCGAA |
| SEQ ID NO:69 | Zebrafish RASSF1 BT probe (Arm 3) | GACGCGAGGCGCGTGCGTTT/3C6/ |
| SEQ ID NO:70 | Zebrafish RASSF1 BT probe (Arm 5) | CCACGGACGCGCGCGTGCGTTT/3C6/ |
| SEQ ID NO:71 | Synthetic Zebrafish RASSF1 sense strand | TCCAC/iMe-dC/GTGGTGCCCACTCTGGACAGGTGGAGCAGAGGGAAGGTGGTG/iMe-dC/GCATGGTGGG/iMe-dC/GAG/iMe-dC/G/iMe-dC/GTG/iMe-dC/GCCTGGAGGACCC/iMe-dC/GATTGGCTGA/iMe-dC/GTGTAAACCAGGA/iMe-dC/GAGGACATGACTTTCAGCCCTGCAGCCAGACAGCTGAGCTGGTGTGTGACCTGTGTGGAGAGTTCATCTGG |
| SEQ ID NO:72 | Synthetic Zebrafish RASSF1 antisense strand | CCAGATGAACTCTCCACACAGGTCACACCAGCTCAGCTGTCGTCTGGCTGGGCTGAAAGTCATGTCCT/iMe-dC/GTCCTGGTTTACA/iMe-dC/GTCAGCCAAT/iMe-dC/GGGGTCCTCCAGG/iMe-dC/GCA/iMe-dC/G/iMe-dC/GCT/iMe-dC/GCCCACCATG/iMe-dC/GCACCACCTTCCCTCGTCCACCTGTCCAGAGTGGGCACCA/iMe-dC/GGTGGA |
| SEQ ID NO:73 | B3GALT6 BT Forward primer | GGTTTATTTTGGTTTTTTGAGTTTTCGG |
| SEQ ID NO:74 | B3GALT6 BT Reverse primer | TCCAACCTACTACTATTTACGCGAA |
| SEQ ID NO:75 | B3GALT6 BT probe-Arm 1 | CGCCGAGGGGCGGATTTAGGG/3C6/ |
| SEQ ID NO:76 | Beta Actin BT PCR/Flap assay Forward Primer | GTGTTTGTTTTTGATTAGGTGTTTAAGA |
| SEQ ID NO:77 | Beta Actin BT PCR/Flap assay Reverse Primer | CTTTACACCAACCTCATAACCTTATC |
| SEQ ID NO:78 | Beta Actin probe-Arm 3 | GACGCGGAGATAGTGTTGTGG /3C6/ |
| SEQ ID NO:79 | Arm 1 HEX FRET Cassette | /HEX/TCT/BHQ-1/AGCCGGTTTTCCGGCTGAGACCTGGCG/3C6/ |
| SEQ ID NO:80 | Arm 5 FAM FRET Cassette | /FAM/TCT/BHQ-1/AGCCGGTTTTCCGGCTGAGACGTCCGTGG/3C6/ |
| SEQ ID NO:81 | Arm 3 QUASAR-670 FRET Cassette | /Q670/TCT/BHQ-2/AGCCGGTTTTCCGGCTGAGACTCCGCGTC/3C6/ |

FIG. 13F

SEQUENCE LISTING

<160> NUMBER OF SEQ ID NOS: 103

<210> SEQ ID NO 1
<211> LENGTH: 224
<212> TYPE: DNA
<213> ORGANISM: Artificial sequence
<220> FEATURE:
<223> OTHER INFORMATION: Synthetic DNA

<400> SEQUENCE: 1

```
aagggctgct ctccggccag cctgggcgcc ggggacagca gccggcgcgg cgtcctacct    60
ggtgaagttc gtcctgccct cggcgtggac ccaggccccg gtcgccgccc gggagggcac   120
cggcctcgct cgcttgctcg ctcgcccgcc cttgcccgct cgctccccgc ccgccgcctc   180
cctcgcgcgc ccgctccggt cctccggctc ccactacagc tcat                    224
```

<210> SEQ ID NO 2
<211> LENGTH: 132
<212> TYPE: DNA
<213> ORGANISM: Artificial sequence
<220> FEATURE:
<223> OTHER INFORMATION: Synthetic DNA

<400> SEQUENCE: 2

```
tgccctcggc gtggacccag gccccggtcg ccgcccggga gggcaccggc ctcgctcgct    60
tgctcgctcg cccgcccttg cccgctcgct ccccgcccgc cgcctccctc gcgcgcccgc   120
tccggtcctc cg                                                       132
```

<210> SEQ ID NO 3
<211> LENGTH: 224
<212> TYPE: DNA
<213> ORGANISM: Artificial sequence
<220> FEATURE:
<223> OTHER INFORMATION: Synthetic DNA

<400> SEQUENCE: 3

```
aagggttgtt tttcggttag tttgggcgtc ggggatagta gtcggcgcgg cgttttattt    60
ggtgaagttc gttttgtttt cggcgtggat ttaggtttcg gtcgtcgttc gggagggtat   120
cggtttcgtt cgtttgttcg ttcgttcgtt tttgttcgtt cgttttcgt tcgtcgtttt    180
tttcgcgcgt tcgtttcggt ttttcggttt ttattatagt ttat                    224
```

<210> SEQ ID NO 4
<211> LENGTH: 132
<212> TYPE: DNA
<213> ORGANISM: Artificial sequence
<220> FEATURE:
<223> OTHER INFORMATION: Synthetic DNA

<400> SEQUENCE: 4

```
tgttttcggc gtggatttag gtttcggtcg tcgttcggga gggtatcggt ttcgttcgtt    60
tgttcgttcg ttcgtttttg ttcgttcgtt tttcgttcgt cgttttttc gcgcgttcgt   120
ttcggttttt cg                                                       132
```

<210> SEQ ID NO 5
<211> LENGTH: 21
<212> TYPE: DNA
<213> ORGANISM: Artificial sequence
<220> FEATURE:
<223> OTHER INFORMATION: Synthetic DNA

<400> SEQUENCE: 5

```
tgttttcggc gtggatttag g                                              21

<210> SEQ ID NO 6
<211> LENGTH: 20
<212> TYPE: DNA
<213> ORGANISM: Artificial sequence
<220> FEATURE:
<223> OTHER INFORMATION: Synthetic DNA

<400> SEQUENCE: 6
cgaaaaaccg aaacgaacgc                                                20

<210> SEQ ID NO 7
<211> LENGTH: 58
<212> TYPE: DNA
<213> ORGANISM: Artificial sequence
<220> FEATURE:
<223> OTHER INFORMATION: Synthetic DNA

<400> SEQUENCE: 7
gtcgtcgttc gggagggtat cggtttcgtt cgtttgttcg ttcgttcgtt tttgttcg      58

<210> SEQ ID NO 8
<211> LENGTH: 19
<212> TYPE: DNA
<213> ORGANISM: Artificial sequence
<220> FEATURE:
<223> OTHER INFORMATION: Synthetic DNA

<400> SEQUENCE: 8
gtcgtcgttc gagagggta                                                 19

<210> SEQ ID NO 9
<211> LENGTH: 22
<212> TYPE: DNA
<213> ORGANISM: Artificial sequence
<220> FEATURE:
<223> OTHER INFORMATION: Synthetic DNA

<400> SEQUENCE: 9
cgaacaaaaa cgaacgaacg aa                                             22

<210> SEQ ID NO 10
<211> LENGTH: 21
<212> TYPE: DNA
<213> ORGANISM: Artificial sequence
<220> FEATURE:
<223> OTHER INFORMATION: Synthetic DNA

<400> SEQUENCE: 10
ccacggacga tcggtttcgt t                                              21

<210> SEQ ID NO 11
<211> LENGTH: 186
<212> TYPE: DNA
<213> ORGANISM: Artificial sequence
<220> FEATURE:
<223> OTHER INFORMATION: Synthetic DNA

<400> SEQUENCE: 11
cggccggggc gcacggagag cgcgcgggac tcgctgcagc ggcggccggg tcgcggcgca    60
cccgggccgg gaccggagcc gagcctagcg cggcgcccgc gacccgtcag ccgcggctcc   120
tgctccctcg atcccgcgcg gggaaagggc cggcggctgt tggcgtcggc ggggcgcgga   180
``` ggaacc                                                                186

<210> SEQ ID NO 12
<211> LENGTH: 145
<212> TYPE: DNA
<213> ORGANISM: Artificial sequence
<220> FEATURE:
<223> OTHER INFORMATION: Synthetic DNA

<400> SEQUENCE: 12
gcgcgcggga ctcgctgcag cggcggccgg gtcgcggcgc acccgggccg ggaccggagc      60
cgagcctagc gcggcgcccg cgacccgtca gccgcggctc ctgctccctc gatcccgcgc     120
ggggaaaggg ccggcggctg ttggc                                          145

<210> SEQ ID NO 13
<211> LENGTH: 186
<212> TYPE: DNA
<213> ORGANISM: Artificial sequence
<220> FEATURE:
<223> OTHER INFORMATION: Synthetic DNA

<400> SEQUENCE: 13
cggtcggggc gtacggagag cgcgcgggat tcgttgtagc ggcggtcggg tcgcggcgta      60
ttcgggtcgg gatcggagtc gagtttagcg cggcgttcgc gattcgttag tcgcggtttt     120
tgttttttcg atttcgcgcg gggaaagggt cggcggttgt tggcgtcggc ggggcgcgga    180
ggaatt                                                               186

<210> SEQ ID NO 14
<211> LENGTH: 145
<212> TYPE: DNA
<213> ORGANISM: Artificial sequence
<220> FEATURE:
<223> OTHER INFORMATION: Synthetic DNA

<400> SEQUENCE: 14
gcgcgcggga ttcgttgtag cggcggtcgg gtcgcggcgt attcgggtcg ggatcggagt      60
cgagtttagc gcggcgttcg cgattcgtta gtcgcggttt tgttttttc gatttcgcgc     120 ggggaaaggg tcggcggttg ttggc                                          145

<210> SEQ ID NO 15
<211> LENGTH: 18
<212> TYPE: DNA
<213> ORGANISM: Artificial sequence
<220> FEATURE:
<223> OTHER INFORMATION: Synthetic DNA

<400> SEQUENCE: 15
cgcgggattc gttgtagc                                                   18

<210> SEQ ID NO 16
<211> LENGTH: 17
<212> TYPE: DNA
<213> ORGANISM: Artificial sequence
<220> FEATURE:
<223> OTHER INFORMATION: Synthetic DNA

<400> SEQUENCE: 16
caaccgccga ccctttc                                                    17

<210> SEQ ID NO 17
<211> LENGTH: 52

```
<212> TYPE: DNA
<213> ORGANISM: Artificial sequence
<220> FEATURE:
<223> OTHER INFORMATION: Synthetic DNA

<400> SEQUENCE: 17
tcggagtcga gtttagcgcg gcgttcgcga ttcgttagtc gcggttttg tt         52

<210> SEQ ID NO 18
<211> LENGTH: 19
<212> TYPE: DNA
<213> ORGANISM: Artificial sequence
<220> FEATURE:
<223> OTHER INFORMATION: Synthetic DNA

<400> SEQUENCE: 18
tcggagtcga gtttagcgc                                              19

<210> SEQ ID NO 19
<211> LENGTH: 21
<212> TYPE: DNA
<213> ORGANISM: Artificial sequence
<220> FEATURE:
<223> OTHER INFORMATION: Synthetic DNA

<400> SEQUENCE: 19
aacaaaaacc gcgactaacg a                                           21

<210> SEQ ID NO 20
<211> LENGTH: 21
<212> TYPE: DNA
<213> ORGANISM: Artificial sequence
<220> FEATURE:
<223> OTHER INFORMATION: Synthetic DNA

<400> SEQUENCE: 20
ccacggacgc ggcgttcgcg a                                           21

<210> SEQ ID NO 21
<211> LENGTH: 208
<212> TYPE: DNA
<213> ORGANISM: Artificial sequence
<220> FEATURE:
<223> OTHER INFORMATION: Synthetic DNA

<400> SEQUENCE: 21
ctgggtcagc gcagcaagtg gggctggccg ctatctcgct gcaccggcc gcgtcccggg   60 ctccgtgcgc cctcgcccca gctggtttgg agttcaaccc tcggctccgc cgccggctcc  120
ttgcgccttc ggagtgtccc gcagcgacgc cgggagccga cgcgccgcgc gggtacctag  180
ccatggctgg ggcgagcagg ctgctctt                                    208

<210> SEQ ID NO 22
<211> LENGTH: 138
<212> TYPE: DNA
<213> ORGANISM: Artificial sequence
<220> FEATURE:
<223> OTHER INFORMATION: Synthetic DNA

<400> SEQUENCE: 22
gggctccgtg cgccctcgcc ccagctggtt tggagttcaa ccctcggctc cgccgccggc   60
tccttgcgcc ttcggagtgt cccgcagcga cgccgggagc cgacgcgccg cgcgggtacc  120
tagccatggc tggggcga                                               138
```

<210> SEQ ID NO 23
<211> LENGTH: 208
<212> TYPE: DNA
<213> ORGANISM: Artificial sequence
<220> FEATURE:
<223> OTHER INFORMATION: Synthetic DNA

<400> SEQUENCE: 23
ttgggttagc gtagtaagtg gggttggtcg ttatttcgtt gtattcggtc gcgtttcggg    60
tttcgtgcgt tttcgtttta gttggtttgg agtttaatttt tcggtttcgt cgtcggtttt   120
ttgcgttttc ggagtgtttc gtagcgacgt cgggagtcga cgcgtcgcgc gggtatttag   180
ttatggttgg ggcgagtagg ttgtttttt                                      208

<210> SEQ ID NO 24
<211> LENGTH: 139
<212> TYPE: DNA
<213> ORGANISM: Artificial sequence
<220> FEATURE:
<223> OTHER INFORMATION: Synthetic DNA

<400> SEQUENCE: 24
cgggtttcgt gcgttttcgt tttagttggt ttggagttta attttcggtt tcgtcgtcgg    60 tttttttgcgt tttcggagtg tttcgtagcg acgtcgggag tcgacgcgtc gcgcgggtat  120
ttagttatgg ttggggcga                                                 139

<210> SEQ ID NO 25
<211> LENGTH: 24
<212> TYPE: DNA
<213> ORGANISM: Artificial sequence
<220> FEATURE:
<223> OTHER INFORMATION: Synthetic DNA

<400> SEQUENCE: 25
ggtttcgtgc gttttcgttt tagt                                            24

<210> SEQ ID NO 26
<211> LENGTH: 23
<212> TYPE: DNA
<213> ORGANISM: Artificial sequence
<220> FEATURE:
<223> OTHER INFORMATION: Synthetic DNA

<400> SEQUENCE: 26
ccaaccataa ctaaataccc gcg                                             23

<210> SEQ ID NO 27
<211> LENGTH: 55
<212> TYPE: DNA
<213> ORGANISM: Artificial sequence
<220> FEATURE:
<223> OTHER INFORMATION: Synthetic DNA

<400> SEQUENCE: 27
gtttaatttt cggtttcgtc gtcggttttt tgcgttttcg gagtgtttcg tagcg          55

<210> SEQ ID NO 28
<211> LENGTH: 23
<212> TYPE: DNA
<213> ORGANISM: Artificial sequence
<220> FEATURE:
<223> OTHER INFORMATION: Synthetic DNA

<400> SEQUENCE: 28
gtttaatttt cggtttcgtc gtc                                               23

<210> SEQ ID NO 29
<211> LENGTH: 18
<212> TYPE: DNA
<213> ORGANISM: Artificial sequence
<220> FEATURE:
<223> OTHER INFORMATION: Synthetic DNA

<400> SEQUENCE: 29
cgctacgaaa cactccga                                                     18

<210> SEQ ID NO 30
<211> LENGTH: 20
<212> TYPE: DNA
<213> ORGANISM: Artificial sequence
<220> FEATURE:
<223> OTHER INFORMATION: Synthetic DNA

<400> SEQUENCE: 30
cgccgaggcg gtttttgcg                                                    20

<210> SEQ ID NO 31
<211> LENGTH: 224
<212> TYPE: DNA
<213> ORGANISM: Artificial sequence
<220> FEATURE:
<223> OTHER INFORMATION: Synthetic DNA

<400> SEQUENCE: 31
cgcagcgcac ccagcacagt ccgcgcggcg gagcgggtga gaagtcggcg ggggcgcgga        60
tcgaccgggg tgtccccag gctccgcgtc gcggtccccg ctcgccctcc cgcccgccca       120
ccgggcaccc cagccgcgca gaaggcggaa gccacgcgcg agggaccgcg gtccgtccgg       180
gactagcccc aggcccggca ccgccccgcg ggccgagcgc ccac                       224

<210> SEQ ID NO 32
<211> LENGTH: 111
<212> TYPE: DNA
<213> ORGANISM: Artificial sequence
<220> FEATURE:
<223> OTHER INFORMATION: Synthetic DNA

<400> SEQUENCE: 32
gaccggggtg tcccccaggc tccgcgtcgc ggtccccgct cgccctccg cccgcccacc         60 gggcacccca gccgcgcaga aggcggaagc cacgcgcgag ggaccgcggt c                111

<210> SEQ ID NO 33
<211> LENGTH: 224
<212> TYPE: DNA
<213> ORGANISM: Artificial sequence
<220> FEATURE:
<223> OTHER INFORMATION: Synthetic DNA

<400> SEQUENCE: 33
cgtagcgtat ttagtatagt tcgcgcggcg gagcgggtga gaagtcggcg ggggcgcgga        60
tcgatcgggg tgttttttag gtttcgcgtc gcggttttcg ttcgtttttt cgttcgttta      120
tcgggtattt tagtcgcgta gaaggcggaa gttacgcgcg agggatcgcg gttcgttcgg      180
gattagtttt aggttcggta tcgtttcgcg ggtcgagcgt ttat                       224

<210> SEQ ID NO 34

```
<211> LENGTH: 111
<212> TYPE: DNA
<213> ORGANISM: Artificial sequence
<220> FEATURE:
<223> OTHER INFORMATION: Synthetic DNA

<400> SEQUENCE: 34
gatcggggtg ttttttaggt ttcgcgtcgc ggttttcgtt cgttttttcg ttcgtttatc      60
gggtatttta gtcgcgtaga aggcggaagt tacgcgcgag ggatcgcggt t              111

<210> SEQ ID NO 35
<211> LENGTH: 22
<212> TYPE: DNA
<213> ORGANISM: Artificial sequence
<220> FEATURE:
<223> OTHER INFORMATION: Synthetic DNA

<400> SEQUENCE: 35 ggtgttttt aggtttcgcg tc                                                22

<210> SEQ ID NO 36
<211> LENGTH: 17
<212> TYPE: DNA
<213> ORGANISM: Artificial sequence
<220> FEATURE:
<223> OTHER INFORMATION: Synthetic DNA

<400> SEQUENCE: 36
gatccctcgc gcgtaac                                                     17

<210> SEQ ID NO 37
<211> LENGTH: 57
<212> TYPE: DNA
<213> ORGANISM: Artificial sequence
<220> FEATURE:
<223> OTHER INFORMATION: Synthetic DNA

<400> SEQUENCE: 37
cggttttcgt tcgttttttc gttcgtttat cgggtatttt agtcgcgtag aaggcgg        57

<210> SEQ ID NO 38
<211> LENGTH: 21
<212> TYPE: DNA
<213> ORGANISM: Artificial sequence
<220> FEATURE:
<223> OTHER INFORMATION: Synthetic DNA

<400> SEQUENCE: 38
cggttttcgt tcgttttttc g                                                21

<210> SEQ ID NO 39
<211> LENGTH: 18
<212> TYPE: DNA
<213> ORGANISM: Artificial sequence
<220> FEATURE:
<223> OTHER INFORMATION: Synthetic DNA

<400> SEQUENCE: 39
ccgccttcta cgcgacta                                                    18

<210> SEQ ID NO 40
<211> LENGTH: 21
<212> TYPE: DNA
<213> ORGANISM: Artificial sequence
<220> FEATURE:
<223> OTHER INFORMATION: Synthetic DNA
```

<400> SEQUENCE: 40
ccacggacgg ttcgtttatc g                                       21

<210> SEQ ID NO 41
<211> LENGTH: 224
<212> TYPE: DNA
<213> ORGANISM: Artificial sequence
<220> FEATURE:
<223> OTHER INFORMATION: Synthetic DNA

<400> SEQUENCE: 41
ctctgacctg agtctccttt ggaactctgc aggttctatt tgcttttttcc cagatgagct    60 cttttttctgg tgtttgtctc tctgactagg tgtctaagac agtgttgtgg gtgtaggtac   120
taacactggc tcgtgtgaca aggccatgag gctggtgtaa agcggccttg gagtgtgtat   180
taagtaggtg cacagtaggt ctgaacagac tccccatccc aaga                    224

<210> SEQ ID NO 42
<211> LENGTH: 166
<212> TYPE: DNA
<213> ORGANISM: Artificial sequence
<220> FEATURE:
<223> OTHER INFORMATION: Synthetic DNA

<400> SEQUENCE: 42
ctctgcaggt tctatttgct ttttcccaga tgagctcttt ttctggtgtt tgtctctctg    60
actaggtgtc taagacagtg ttgtgggtgt aggtactaac actggctcgt gtgacaaggc   120
catgaggctg gtgtaaagcg gccttggagt gtgtattaag taggtg                  166

<210> SEQ ID NO 43
<211> LENGTH: 224
<212> TYPE: DNA
<213> ORGANISM: Artificial sequence
<220> FEATURE:
<223> OTHER INFORMATION: Synthetic DNA

<400> SEQUENCE: 43
ttttgatttg agttttttttt ggaattttgt aggttttatt tgttttttttt tagatgagtt   60 ttttttttgg tgtttgtttt tttgattagg tgtttaagat agtgttgtgg gtgtaggtat   120
taatattggt ttgtgtgata aggttatgag gttggtgtaa agtggttttg gagtgtgtat   180
taagtaggtg tatagtaggt ttgaatagat ttttatttt aaga                     224

<210> SEQ ID NO 44
<211> LENGTH: 166
<212> TYPE: DNA
<213> ORGANISM: Artificial sequence
<220> FEATURE:
<223> OTHER INFORMATION: Synthetic DNA

<400> SEQUENCE: 44
ttttgtaggt tttatttgtt ttttttttaga tgagtttttt ttttggtgtt tgttttttttg    60 attaggtgtt taagatagtg ttgtgggtgt aggtattaat attggtttgt gtgataaggt   120
tatgaggttg gtgtaaagtg gttttggagt gtgtattaag taggtg                  166

<210> SEQ ID NO 45
<211> LENGTH: 35
<212> TYPE: DNA
<213> ORGANISM: Artificial sequence
<220> FEATURE:

<223> OTHER INFORMATION: Synthetic DNA

<400> SEQUENCE: 45
ttgtaggttt tatttgtttt tttttagatg agttt                35

<210> SEQ ID NO 46
<211> LENGTH: 27
<212> TYPE: DNA
<213> ORGANISM: Artificial sequence
<220> FEATURE:
<223> OTHER INFORMATION: Synthetic DNA

<400> SEQUENCE: 46
ctacttaata cacactccaa aaccact                27

<210> SEQ ID NO 47
<211> LENGTH: 85
<212> TYPE: DNA
<213> ORGANISM: Artificial sequence
<220> FEATURE:
<223> OTHER INFORMATION: Synthetic DNA

<400> SEQUENCE: 47
tttgtttttt tgattaggtg tttaagatag tgttgtgggt gtaggtatta atattggttt                60
gtgtgataag gttatgaggt tggtg                85

<210> SEQ ID NO 48
<211> LENGTH: 27
<212> TYPE: DNA
<213> ORGANISM: Artificial sequence
<220> FEATURE:
<223> OTHER INFORMATION: Synthetic DNA

<400> SEQUENCE: 48
tttgtttttt tgattaggtg tttaaga                27

<210> SEQ ID NO 49
<211> LENGTH: 21
<212> TYPE: DNA
<213> ORGANISM: Artificial sequence
<220> FEATURE:
<223> OTHER INFORMATION: Synthetic DNA

<400> SEQUENCE: 49
caccaacctc ataaccttat c                21

<210> SEQ ID NO 50
<211> LENGTH: 21
<212> TYPE: DNA
<213> ORGANISM: Artificial sequence
<220> FEATURE:
<223> OTHER INFORMATION: Synthetic DNA

<400> SEQUENCE: 50
gacgcggaga tagtgttgtg g                21

<210> SEQ ID NO 51
<211> LENGTH: 180
<212> TYPE: DNA
<213> ORGANISM: Artificial sequence
<220> FEATURE:
<223> OTHER INFORMATION: Synthetic DNA

<400> SEQUENCE: 51
ccgtggacga gattccagtg gcgcagacgc gcctgggcag cgccgctctg gccgccccgc                60

```
ggggccgggg ccgacagccc acgctggcgc ggcaggcgcg tgcgcccgcc gttttcgtga    120
gcccgagcag cggcgagccc agggcgccgg gcggccggga ggctggtctg gcttagctgg    180
```

<210> SEQ ID NO 52
<211> LENGTH: 146
<212> TYPE: DNA
<213> ORGANISM: Artificial sequence
<220> FEATURE:
<223> OTHER INFORMATION: Synthetic DNA

<400> SEQUENCE: 52

```
gggcagcgcc gctctggccg ccccgcgggg ccggggccga cagcccacgc tggcgcggca     60
ggcgcgtgcg cccgccgttt cgtgagccc gagcagcggc gagcccaggg cgccgggcgg    120
ccgggaggct ggtctggctt agctgg                                         146
```

<210> SEQ ID NO 53
<211> LENGTH: 180
<212> TYPE: DNA
<213> ORGANISM: Artificial sequence
<220> FEATURE:
<223> OTHER INFORMATION: Synthetic DNA

<400> SEQUENCE: 53

```
tcgtggacga gattttagtg gcgtagacgc gtttgggtag cgtcgttttg gtcgtttcgc     60
ggggtcgggg tcgatagttt acgttggcgc ggtaggcgcg tgcgttcgtc gttttcgtga    120
gttcgagtag cggcgagttt agggcgtcgg gcggtcggga ggttggtttg gtttagttgg    180
```

<210> SEQ ID NO 54
<211> LENGTH: 146
<212> TYPE: DNA
<213> ORGANISM: Artificial sequence
<220> FEATURE:
<223> OTHER INFORMATION: Synthetic DNA

<400> SEQUENCE: 54

```
gggtagcgtc gttttggtcg tttcgcgggg tcggggtcga tagtttacgt tggcgcggta     60
ggcgcgtgcg ttcgtcgttt cgtgagttc gagtagcggc gagtttaggg cgtcgggcgg    120
tcgggaggtt ggtttggttt agttgg                                         146
```

<210> SEQ ID NO 55
<211> LENGTH: 20
<212> TYPE: DNA
<213> ORGANISM: Artificial sequence
<220> FEATURE:
<223> OTHER INFORMATION: Synthetic DNA

<400> SEQUENCE: 55

```
agcgtcgttt tggtcgtttc                                                 20
```

<210> SEQ ID NO 56
<211> LENGTH: 17
<212> TYPE: DNA
<213> ORGANISM: Artificial sequence
<220> FEATURE:
<223> OTHER INFORMATION: Synthetic DNA

<400> SEQUENCE: 56

```
gacgccctaa actcgcc                                                    17
```

<210> SEQ ID NO 57

```
<211> LENGTH: 65
<212> TYPE: DNA
<213> ORGANISM: Artificial sequence
<220> FEATURE:
<223> OTHER INFORMATION: Synthetic DNA

<400> SEQUENCE: 57
gtcggggtcg atagtttacg ttggcgcggt aggcgcgtgc gttcgtcgtt ttcgtgagtt     60
cgagt                                                                65

<210> SEQ ID NO 58
<211> LENGTH: 20
<212> TYPE: DNA
<213> ORGANISM: Artificial sequence
<220> FEATURE:
<223> OTHER INFORMATION: Synthetic DNA

<400> SEQUENCE: 58
gtcggggtcg atagtttacg                                                20

<210> SEQ ID NO 59
<211> LENGTH: 19
<212> TYPE: DNA
<213> ORGANISM: Artificial sequence
<220> FEATURE:
<223> OTHER INFORMATION: Synthetic DNA

<400> SEQUENCE: 59
actcgaactc acgaaaacg                                                 19

<210> SEQ ID NO 60
<211> LENGTH: 21
<212> TYPE: DNA
<213> ORGANISM: Artificial sequence
<220> FEATURE:
<223> OTHER INFORMATION: Synthetic DNA

<400> SEQUENCE: 60
gacgcggagg acgaacgcac g                                              21

<210> SEQ ID NO 61
<211> LENGTH: 2241
<212> TYPE: DNA
<213> ORGANISM: Danio rerio

<400> SEQUENCE: 61
tcagcaaatg aagtctgctc tccgttcgct cctcaaagta ggacagatcg cgccggatta     60
agcgttaatc tgagtcttct gcgcatgcgc atgaacgcgc gctacaagcg gacaaggtgc    120
gcgttcgaag aagaaacgaa ccgagccggt ttcgagcagc gacaacgcga atgaagccca    180
cggagtaccg aaaccttgag gaattcatct ttctgccagc ggaggactgt tttcagttta    240
gttttgagcg taatggaaga tgtttgggca cttttgcgca atccctcatg ttatcgcctc    300
acagacacgc gtcgcgcgcg cagattacgc ttaatttgag cggatttgag gaaacagacg    360
cgtttactgt cagtcgaggc tctactgaag actgaaagtg gcttgtttgg gtttaagatt    420
gacccagatg ctactgaaaa ctgtcaatca agaaggaaac tcttgaagca ataaaaacat    480
catctctgtt atatgaagac tgtcagatcc acacagtgat ccatgtttgt ggatatgcaa    540
acacatcaga acgagacgct aaatttatca gcttgctttg gagtaaacag cgttgcttta    600
aaacactcca cagtcataaa tcatctccag ccctaaccat ggtccactga gccatgccgt    660
tcatcctccc acgatcccaa aatggcaaaa tgtgagctca tcgagttgca ggacttgact    720
```

```
ccgaatgacc gtattgagct ggcaccccct agtgtccctc cacccaccgt ggtgcccact      780
ctggacaggt ggagcagagg gaaggtggtg cgcatggtgg gcgagcgcgt gcgcctggag      840
gaccccgatt ggctgacgtg taaaccagga cgaggacatg actttcagcc ctgcagccag      900
acacagctga gctggtgtga cctgtgtgga gagttcatct ggggcctgta cagacagagc      960
ctccgctgca cacactgtaa ctacacttgt cactaccgct gtcaacccct cattcagctg     1020
gactgcagct ccaacaccga cactatctgc gaacaatcaa actacagcga ggacaccatc     1080
gagacagaca ccaatgtgga tgagcagtct gaagtggact ggaggaaaca ggatctgtct     1140
gtcactgaaa tacagcagaa agtgaaggaa tacaatgctc aggtcaacag taacctcttc     1200
atggttctga atcgtgacgg ctcatacact ggcttcatca aggtccagtt taagctggcg     1260
cgacccgtgt ctcttcctcc tccccgcagc gtctcctcct cctccatctc ctcctcttgt     1320
ttaggatggg atggcggctg tcaggagcga acttccttct acctgcccag agacacagtc     1380
aagcacctgc acatcagctc cagcacccgt gccagagagg tcatccaggc cctgctcaac     1440
aagttcactg tggtggacaa tccggctaaa tattccctgt atgagcgcag ccagcgggac     1500
aatcaagtgt acttaaggaa gttagctgat gatgaatgtc cacttttcct gcgtctgtgt     1560
gctggaccca atgagaaagt cctgagttta gtgcttaaag agaatgaaac cggggaagtg     1620
aattgggatg cgttcagttt tcctgaactc cagaacttcc tgcggattct ccagcgggag     1680
gaagaagatc acgtccggca aatcatacgc cgatacactc tggctcgtga taagatgaaa     1740
gaggctatga agaacttcag caagcctggc tgaatgaatc tgtgtttata cctcacaaac     1800
aagagagatc gaggaggaaa caaggcttat tactgtctga gtccaaagag tgtgtgaaag     1860
agcccttcgt cctactgtgg acataatgag ggttgaaagt gaaatgcagt gagcgagaga     1920
agagatgcgt gtgtttgaag catgactgtt gagtgtgact tcacactgga ggaaatgctg     1980
cgctcgtagc cgtagatcca gtggagagat gtcttcctgt ggagaatcta tatatcagtg     2040
cagattacag agtatttttca gcaccattta aacttgtcat aggaaattaa acgaggatta     2100
ttttaatatc tgtatcaaaa tgccacctgt tagtgacaca gtaacttgtc atattttgaa     2160
gctcccatgt atatatttgg atgtttgttg tcaattattc tgaaaataga tacaaataaa     2220
ctatttttcc ctttaaaatg a                                               2241
```

<210> SEQ ID NO 62
<211> LENGTH: 420
<212> TYPE: DNA
<213> ORGANISM: Artificial sequence
<220> FEATURE:
<223> OTHER INFORMATION: Synthetic DNA

<400> SEQUENCE: 62

```
atcagaacga gacgctaaat ttatcagctt gctttggagt aaacagcgtt gctttaaaac       60
actccacagt cataaatcat ctccagccct aaccatggtc cactgagcca tgccgttcat      120
cctcccacga tcccaaaatg gcaaaatgtg agctcatcga gttgcaggac ttgactccga      180
atgaccgtat tgagctggca ccccctagtg tccctccacc caccgtggtg cccactctgg      240
acaggtggag cagagggaag gtggtgcgca tggtgggcga gcgcgtgcgc ctggaggacc      300
ccgattggct gacgtgtaaa ccaggacgag gacatgactt tcagccctgc agccagacac      360
agctgagctg gtgtgacctg tgtggagagt tcatctgggg cctgtacaga cagagcctcc      420
```

<210> SEQ ID NO 63

<211> LENGTH: 420
<212> TYPE: DNA
<213> ORGANISM: Artificial sequence
<220> FEATURE:
<223> OTHER INFORMATION: Synthetic DNA

<400> SEQUENCE: 63

```
attagaacga gacgttaaat ttattagttt gttttggagt aaatagcgtt gttttaaaat      60
attttatagt tataaattat ttttagtttt aattatggtt tattgagtta tgtcgtttat     120
tttttacga ttttaaaatg gtaaaatgtg agtttatcga gttgtaggat ttgatttcga      180
atgatcgtat tgagttggta ttttttagtg ttttttttatt tatcgtggtg tttatttttgg    240
ataggtggag tagagggaag gtggtgcgta tggtgggcga gcgcgtgcgt ttggaggatt     300
tcgattggtt gacgtgtaaa ttaggacgag gatatgattt ttagttttgt agttagatat    360
agttgagttg gtgtgatttg tgtggagagt ttatttgggg tttgtataga tagagttttc    420
```

<210> SEQ ID NO 64
<211> LENGTH: 15
<212> TYPE: DNA
<213> ORGANISM: Artificial sequence
<220> FEATURE:
<223> OTHER INFORMATION: Synthetic DNA

<400> SEQUENCE: 64
cgcatggtgg gcgag      15

<210> SEQ ID NO 65
<211> LENGTH: 18
<212> TYPE: DNA
<213> ORGANISM: Artificial sequence
<220> FEATURE:
<223> OTHER INFORMATION: Synthetic DNA

<400> SEQUENCE: 65
acacgtcagc caatcggg      18

<210> SEQ ID NO 66
<211> LENGTH: 20
<212> TYPE: DNA
<213> ORGANISM: Artificial sequence
<220> FEATURE:
<223> OTHER INFORMATION: Synthetic DNA

<400> SEQUENCE: 66
gacgcggagg cgcgtgcgcc      20

<210> SEQ ID NO 67
<211> LENGTH: 17
<212> TYPE: DNA
<213> ORGANISM: Artificial sequence
<220> FEATURE:
<223> OTHER INFORMATION: Synthetic DNA

<400> SEQUENCE: 67
tgcgtatggt gggcgag      17

<210> SEQ ID NO 68
<211> LENGTH: 26
<212> TYPE: DNA
<213> ORGANISM: Artificial sequence
<220> FEATURE:
<223> OTHER INFORMATION: Synthetic DNA

<400> SEQUENCE: 68

```
cctaatttac acgtcaacca atcgaa                                              26
```

<210> SEQ ID NO 69
<211> LENGTH: 21
<212> TYPE: DNA
<213> ORGANISM: Artificial sequence
<220> FEATURE:
<223> OTHER INFORMATION: Synthetic DNA

<400> SEQUENCE: 69

```
gacgcggagg cgcgtgcgtt t                                                   21
```

<210> SEQ ID NO 70
<211> LENGTH: 21
<212> TYPE: DNA
<213> ORGANISM: Artificial sequence
<220> FEATURE:
<223> OTHER INFORMATION: Synthetic DNA

<400> SEQUENCE: 70

```
ccacggacgg cgcgtgcgtt t                                                   21
```

<210> SEQ ID NO 71
<211> LENGTH: 171
<212> TYPE: DNA
<213> ORGANISM: Artificial sequence
<220> FEATURE:
<223> OTHER INFORMATION: Synthetic DNA

<400> SEQUENCE: 71

```
tccacgtggt gcccactctg dacaggtgga gcagagggaa ggtggtggca tggtggggag         60
ggtggcctgg aggacccgat tggctgagtg taaaccagga gaggacatga ctttcagccc        120
tgcagccaga cacagctgag ctggtgtgac ctgtgtggag agttcatctg g                 171
```

<210> SEQ ID NO 72
<211> LENGTH: 171
<212> TYPE: DNA
<213> ORGANISM: Artificial sequence
<220> FEATURE:
<223> OTHER INFORMATION: Synthetic DNA

<400> SEQUENCE: 72

```
ccagatgaac tctccacaca ggtcacacca gctcagctgt gtctggctgc agggctgaaa         60
gtcatgtcct gtcctggttt acagtcagcc aatggggtcc tcagggcag gctgcccacc        120 atggcaccac cttccctctg ctccacctgt ccagagtggg caccaggtgg a                 171
```

<210> SEQ ID NO 73
<211> LENGTH: 28
<212> TYPE: DNA
<213> ORGANISM: Artificial sequence
<220> FEATURE:
<223> OTHER INFORMATION: Synthetic DNA

<400> SEQUENCE: 73

```
ggtttatttt ggttttttga gttttcgg                                            28
```

<210> SEQ ID NO 74
<211> LENGTH: 24
<212> TYPE: DNA
<213> ORGANISM: Artificial sequence
<220> FEATURE:
<223> OTHER INFORMATION: Synthetic DNA

<400> SEQUENCE: 74
tccaacctac tatatttacg cgaa                                     24

<210> SEQ ID NO 75

<400> SEQUENCE: 75

000

<210> SEQ ID NO 76
<211> LENGTH: 20
<212> TYPE: DNA
<213> ORGANISM: Artificial sequence
<220> FEATURE:
<223> OTHER INFORMATION: Synthetic DNA

<400> SEQUENCE: 76
cgccgagggc ggatttaggg                                          20

<210> SEQ ID NO 77
<211> LENGTH: 30
<212> TYPE: DNA
<213> ORGANISM: Artificial sequence
<220> FEATURE:
<223> OTHER INFORMATION: Synthetic DNA

<400> SEQUENCE: 77
gtgtttgttt ttttgattag gtgtttaaga                               30

<210> SEQ ID NO 78
<211> LENGTH: 26
<212> TYPE: DNA
<213> ORGANISM: Artificial sequence
<220> FEATURE:
<223> OTHER INFORMATION: Synthetic DNA

<400> SEQUENCE: 78
ctttacacca acctcataac cttatc                                   26

<210> SEQ ID NO 79
<211> LENGTH: 21
<212> TYPE: DNA
<213> ORGANISM: Artificial sequence
<220> FEATURE:
<223> OTHER INFORMATION: Synthetic DNA

<400> SEQUENCE: 79
gacgcggaga tagtgttgtg g                                        21

<210> SEQ ID NO 80
<211> LENGTH: 28
<212> TYPE: DNA
<213> ORGANISM: Artificial sequence
<220> FEATURE:
<223> OTHER INFORMATION: Synthetic DNA

<400> SEQUENCE: 80
agccggtttt ccggctgaga cctcggcg                                 28

<210> SEQ ID NO 81
<211> LENGTH: 29
<212> TYPE: DNA
<213> ORGANISM: Artificial sequence
<220> FEATURE:
<223> OTHER INFORMATION: Synthetic DNA

<400> SEQUENCE: 81
agccggtttt ccggctgaga cgtccgtgg                               29

<210> SEQ ID NO 82
<211> LENGTH: 29
<212> TYPE: DNA
<213> ORGANISM: Artificial sequence
<220> FEATURE:
<223> OTHER INFORMATION: Synthetic DNA

<400> SEQUENCE: 82
agccggtttt ccggctgaga ctccgcgtc                               29

<210> SEQ ID NO 83
<211> LENGTH: 132
<212> TYPE: DNA
<213> ORGANISM: Artificial sequence
<220> FEATURE:
<223> OTHER INFORMATION: Synthetic DNA

<400> SEQUENCE: 83
tgccctcggc gtggacccag gccccggtcg ccgcccggga gggcaccggc ctcgctcgct    60
tgctcgctcg cccgcccttg cccgctcgct ccccgcccgc cgcctccctc gcgcgcccgc   120
tccggtcctc cg                                                       132

<210> SEQ ID NO 84
<211> LENGTH: 132
<212> TYPE: DNA
<213> ORGANISM: Artificial sequence
<220> FEATURE:
<223> OTHER INFORMATION: Synthetic DNA

<400> SEQUENCE: 84
tgttttcggc gtggatttag gtttcggtcg tcgttcggga gggtatcggt ttcgttcgtt    60
tgttcgttcg ttcgtttttg ttcgttcgtt tttcgttcgt cgttttttc gcgcgttcgt   120 ttcggttttt cg                                                       132

<210> SEQ ID NO 85
<211> LENGTH: 12
<212> TYPE: DNA
<213> ORGANISM: Artificial sequence
<220> FEATURE:
<223> OTHER INFORMATION: Synthetic DNA

<400> SEQUENCE: 85
atcggtttcg tt                                                 12

<210> SEQ ID NO 86
<211> LENGTH: 58
<212> TYPE: DNA
<213> ORGANISM: Artificial sequence
<220> FEATURE:
<223> OTHER INFORMATION: Synthetic DNA

<400> SEQUENCE: 86
gtcgtcgttc gggagggtat cggtttcgtt cgtttgttcg ttcgttcgtt tttgttcg      58

<210> SEQ ID NO 87
<211> LENGTH: 145
<212> TYPE: DNA
<213> ORGANISM: Artificial sequence
<220> FEATURE:
<223> OTHER INFORMATION: Synthetic DNA

<400> SEQUENCE: 87
gcgcgcggga ctcgctgcag cggcggccgg gtcgcggcgc acccgggccg ggaccggagc      60
cgagcctagc gcggcgcccg cgacccgtca gccgcggctc ctgctccctc gatcccgcgc     120
ggggaaaggg ccggcggctg ttggc                                          145

<210> SEQ ID NO 88
<211> LENGTH: 145
<212> TYPE: DNA
<213> ORGANISM: Artificial sequence
<220> FEATURE:
<223> OTHER INFORMATION: Synthetic DNA

<400> SEQUENCE: 88
gcgcgcggga ttcgttgtag cggcggtcgg gtcgcggcgt attcgggtcg ggatcggagt      60
cgagtttagc gcggcgttcg cgattcgtta gtcgcggttt ttgttttttc gatttcgcgc     120
ggggaaaggg tcggcggttg ttggc                                          145

<210> SEQ ID NO 89
<211> LENGTH: 12
<212> TYPE: DNA
<213> ORGANISM: Artificial sequence
<220> FEATURE:
<223> OTHER INFORMATION: Synthetic DNA

<400> SEQUENCE: 89
cggcgttcgc ga                                                         12

<210> SEQ ID NO 90
<211> LENGTH: 139
<212> TYPE: DNA
<213> ORGANISM: Artificial sequence
<220> FEATURE:
<223> OTHER INFORMATION: Synthetic DNA

<400> SEQUENCE: 90
cgggctccgt gcgccctcgc cccagctggt tggagttca accctcggct ccgccgccgg       60
ctccttgcgc cttcggagtg tcccgcagcg acgccgggag ccgacgcgcc gcgcgggtac    120
ctagccatgg ctggggcga                                                 139

<210> SEQ ID NO 91
<211> LENGTH: 139
<212> TYPE: DNA
<213> ORGANISM: Artificial sequence
<220> FEATURE:
<223> OTHER INFORMATION: Synthetic DNA

<400> SEQUENCE: 91
cgggtttcgt gcgttttcgt tttagttggt ttggagttta attttcggtt tcgtcgtcgg      60 tttttttgcgt tttcggagtg tttcgtagcg acgtcgggag tcgacgcgtc gcgcgggtat   120
ttagttatgg ttggggcga                                                 139

<210> SEQ ID NO 92
<211> LENGTH: 12
<212> TYPE: DNA
<213> ORGANISM: Artificial sequence
<220> FEATURE:
<223> OTHER INFORMATION: Synthetic DNA

<400> SEQUENCE: 92
cggttttttg cg                                                           12

<210> SEQ ID NO 93
<211> LENGTH: 111
<212> TYPE: DNA
<213> ORGANISM: Artificial sequence
<220> FEATURE:
<223> OTHER INFORMATION: Synthetic DNA

<400> SEQUENCE: 93
gaccggggtg tcccccaggc tccgcgtcgc ggtccccgct cgccctcccg cccgcccacc      60
gggcacccca gccgcgcaga aggcggaagc cacgcgcgag ggaccgcggt c              111

<210> SEQ ID NO 94
<211> LENGTH: 111
<212> TYPE: DNA
<213> ORGANISM: Artificial sequence
<220> FEATURE:
<223> OTHER INFORMATION: Synthetic DNA

<400> SEQUENCE: 94
gatcggggtg tttttaggt ttcgcgtcgc ggttttcgtt cgttttttcg ttcgtttatc      60 gggtattta gtcgcgtaga aggcggaagt tacgcgcgag ggatcgcggt t              111

<210> SEQ ID NO 95
<211> LENGTH: 12
<212> TYPE: DNA
<213> ORGANISM: Artificial sequence
<220> FEATURE:
<223> OTHER INFORMATION: Synthetic DNA

<400> SEQUENCE: 95
gttcgtttat cg                                                           12

<210> SEQ ID NO 96
<211> LENGTH: 166
<212> TYPE: DNA
<213> ORGANISM: Artificial sequence
<220> FEATURE:
<223> OTHER INFORMATION: Synthetic DNA

<400> SEQUENCE: 96
ctctgcaggt tctatttgct ttttcccaga tgagctcttt ttctggtgtt tgtctctctg      60
actaggtgtc taagacagtg ttgtgggtgt aggtactaac actggctcgt gtgacaaggc     120
catgaggctg gtgtaaagcg gccttggagt gtgtattaag taggtg                   166

<210> SEQ ID NO 97
<211> LENGTH: 166
<212> TYPE: DNA
<213> ORGANISM: Artificial sequence
<220> FEATURE:
<223> OTHER INFORMATION: Synthetic DNA

<400> SEQUENCE: 97
ttttgtaggt tttatttgtt ttttttaga tgagtttttt ttttggtgtt tgttttttg      60 attaggtgtt taagatagtg ttgtgggtgt aggtattaat attggtttgt gtgataaggt     120
tatgaggttg gtgtaaagtg gttttggagt gtgtattaag taggtg                   166

<210> SEQ ID NO 98
<211> LENGTH: 12
<212> TYPE: DNA
<213> ORGANISM: Artificial sequence
<220> FEATURE:
<223> OTHER INFORMATION: Synthetic DNA

<400> SEQUENCE: 98
atagtgttgt gg                                                                                      12

<210> SEQ ID NO 99
<211> LENGTH: 146
<212> TYPE: DNA
<213> ORGANISM: Artificial sequence
<220> FEATURE:
<223> OTHER INFORMATION: Synthetic DNA

<400> SEQUENCE: 99
gggcagcgcc gctctggccg ccccgcgggg ccggggccga cagcccacgc tggcgcggca      60
ggcgcgtgcg cccgccgttt tcgtgagccc gagcagcggc gagcccaggg cgccgggcgg     120
ccgggaggct ggtctggctt agctgg                                         146

<210> SEQ ID NO 100
<211> LENGTH: 145
<212> TYPE: DNA
<213> ORGANISM: Artificial sequence
<220> FEATURE:
<223> OTHER INFORMATION: Synthetic DNA

<400> SEQUENCE: 100
gggtagcgtc gttttggtcg tttcgcgggg tcggggtcga tagtttacgt tggcgcggta      60
ggcgcgtgcg ttcgtcgttt tcgtgagttc gagtagcggc gagtttaggg cgtcgggcgg     120
tcgggaggtt ggtttggttt agttg                                          145

<210> SEQ ID NO 101
<211> LENGTH: 12
<212> TYPE: DNA
<213> ORGANISM: Artificial sequence
<220> FEATURE:
<223> OTHER INFORMATION: Synthetic DNA

<400> SEQUENCE: 101
gacgaacgca cg                                                                                       12

<210> SEQ ID NO 102
<211> LENGTH: 24
<212> TYPE: DNA
<213> ORGANISM: Artificial sequence
<220> FEATURE:
<223> OTHER INFORMATION: Synthetic

<400> SEQUENCE: 102
ctactgtgca cctacttaat acac                                                                          24

<210> SEQ ID NO 103
<211> LENGTH: 20
<212> TYPE: DNA
<213> ORGANISM: Artificial sequence
<220> FEATURE:
<223> OTHER INFORMATION: Synthetic

<400> SEQUENCE: 103
cgccgagggc ggccttggag                                                                               20

MULTIPLEX AMPLIFICATION DETECTION ASSAY

CROSS-REFERENCE TO RELATED APPLICATIONS

The present application is a continuation of U.S. patent application Ser. No. 15/335,096, filed Oct. 26, 2016, now allowed, which claims priority to U.S. Provisional Application Ser. No. 62/249,097, filed Oct. 30, 2015, each of which is incorporated herein by reference.

FIELD OF THE INVENTION

Provided herein is technology relating to the amplification-based detection of nucleic acids and particularly, but not exclusively, to methods and compositions for multiplex amplification of low-level sample DNA prior to further characterization of the sample DNA. The technology further provides methods for isolating DNA from blood or blood product samples, e.g., plasma samples.

BACKGROUND

Methods for the quantification of nucleic acids are important in many areas of molecular biology and in particular for molecular diagnostics. At the DNA level, such methods are used, for example, to determine the presence or absence of variant alleles, the copy numbers of gene sequences amplified in a genome, and the amount, presence, or absence of methylation across genes or at specific loci within genes. Further, methods for the quantification of nucleic acids are used to determine mRNA quantities as a measure of gene expression.

Among the number of different analytical methods that detect and quantify nucleic acids or nucleic acid sequences, variants of the polymerase chain reaction (PCR) have become the most powerful and widespread technology, the principles of which are disclosed in U.S. Pat. Nos. 4,683,195; 4,683,202; and 4,965,188.

Detection of nucleic acids that are present at low levels in samples (e.g., such as DNA from a disease locus, e.g., a tumor, that is collected from a sample that is remote from the disease locus, e.g., DNA that finds its way into stool, sputum, urine, plasma, etc., "remote DNA samples") can be difficult, in part because many DNAs found in such samples are not only present in low amounts, they are also generally fragmented. See, e.g., WO 2006/113770 to Ballhause, and US Patent Publication US 201110009277 A1, to Davos, each of which is incorporated herein by reference in its entirety. For example, cell-free DNA (cfDNA) found in plasma can be highly fragmented, and much of the DNA that might be of interest, e.g., tumor-derived DNA can be very small, e.g., 200 or fewer nucleotides in length. Nucleic acids of this size can be lost during routine purification, due to, e.g., poor binding to purification columns or inefficient alcohol precipitation.

Analysis of such nucleic acids from such samples is especially difficult if multiple targets or loci in the nucleic acid(s) need to be detected. For example, a collected specimen having small numbers of copies of the targets of interest often cannot be divided into a sufficient number of aliquots to permit testing for all targets without risking the accuracy of the tests for the individual targets, e.g., by false negative results.

Pre-amplification of target nucleic acids (e.g., genomic DNA, cDNA, etc.) in a low-target sample may be used to enrich the DNA in the sample prior to dividing the sample for further specific target analysis. For example, whole genome amplification using simple primers (e.g., random hexamers) has been used to increase the amounts of essentially all DNA in a sample, in a manner that is not specific to any particular target of interest. (Sigma-Aldrich's GenomePlex systems, Arneson, et al., Cold Spring Harb. Protoc.; 2008; doi: 10.1101/pdb.prot4920).

Another approach is to amplify one or more regions of particular interest in a semi-targeted manner, to produce a mixture of amplified fragments (amplicons) that contains the different mutations or loci that will be further analyzed. Successive rounds of amplification using the same primers are prone to high background of non-specific amplification, and the production of artifacts, e.g., artificially recombined molecules, high non-specific background, and biased amplification of different intended targets. Thus, such pre-amplification PCR is typically carried out under special conditions e.g., a limited number of cycles, and/or using a low concentration of primers (e.g., 10 to 20-fold lower than in standard PCR) to avoid increases in non-specific background amplification, as use of concentrations over about 160 nM of each primer in multiplex pre-amplification has been shown to increase amplification background in negative control reactions (see, e.g., Andersson, et al., Expert Rev. Mol. Diagn. Early online, 1-16 (2015)).

After a first round of amplification in a multiplex PCR, pre-amplified DNA is typically diluted and aliquoted into new amplification reactions for quantitative or qualitative PCR analysis using conditions typical of standard PCR, e.g., higher concentrations of reagents and larger numbers of cycles, and the second amplification is generally carried out using different primer pairs, e.g., "nested" primers that anneal to sites within the pre-amplified fragments, rather than annealing to the original primer sites at the ends of the amplicons.

When DNA is to be examined for methylation, the analysis is further complicated by the fact that commonly used processes for preparing samples for methylation detection typically result in substantial losses of sample DNA. For example, bisulfite treatment is typically used to convert unmethylated cytosine residues to uracil residues, but the process typically results in only about 30% recovery of the input DNA. In addition, amplification of DNA after treatment with bisulfite is especially challenging. For example, the conversion of unmethylated cytosines reduces the complexity of the DNA sequences and the treatment itself is known to cause significant damage to the DNA, e.g., strand breakage, both of which can contribute to increased background in amplification reactions, especially in multiplexed amplifications.

SUMMARY

In the course of development of methods described herein, it has been determined that bisulfite-treated DNA from low-target samples can be pre-amplified and amplified for real-time detection without the need for whole-genome pre-amplification and without the use of nested or semi-nested primers. Surprisingly, the targeted pre-amplification can be multiplexed using a combination of the same primer pairs that will be used in a second round of amplification of individual target loci, e.g., in a quantitative allele-specific real-time target and signal amplification (QuARTS) assay (see, e.g., U.S. Pat. Nos. 8,361,720, 8,715,937 and 8,916,344), which combines PCR target amplification and FEN-1-mediated flap cleavage for signal amplification.

In some embodiments, the technology provides a method of analyzing samples such that a plurality of different targets that are present in low copy number may be individually detected with reduced risk of false negative results due to sample splitting. For example, in some embodiments, the technology provides a method of analyzing a sample for multiple target nucleic acids, comprising:
a) providing a sample having volume x, the sample comprising bisulfite-treated DNA suspected of containing one or more of a plurality of n different target regions, wherein at least one of said target regions is a low-copy target that, if present in said sample, is present in said sample at a copy number such that:
  i) among n fractions of said sample each having a volume of x/n, said low copy target is absent from one or more of said n fractions, or
  ii) among n fractions of said sample each having a volume of x/n, said low copy target in one or more of said n fractions is below a level of sensitivity of a detection assay for said low copy target;
b) treating said volume x of said sample to an amplification reaction under conditions wherein said n different target regions, if present in said sample, are amplified to form a pre-amplified mixture having volume y;
c) partitioning said pre-amplified mixture into a plurality of different detection assay reaction mixtures, wherein each detection assay reaction mixture comprises a portion of said pre-amplified mixture that has a volume of y/n or less, and wherein said low-copy target, if present in said sample at step a), is present in each of said detection assay reaction mixtures; and
d) conducting a plurality of detection assays with said detection assay reaction mixtures, wherein said different target regions, if present in said sample at step a), are detected in said detection assay reaction mixtures.

In some embodiments, the bisulfite treated DNA is from a human subject. In certain preferred embodiments, the sample is prepared from a body fluid of a subject, preferably a body fluid comprising plasma. In some embodiments, the bisulfite treated DNA is circulating cell-free DNA (cfDNA) isolated from plasma, e.g., cell-free DNA of less than 200 base pairs in length. In particularly preferred embodiments, cell-free DNA is isolated from plasma by a method comprising combining the plasma sample with a protease (e.g., Pronase, proteinase K) and a first lysis reagent that comprises guanidine thiocyanate and non-ionic detergent to form a mixture in which proteins are digested by the protease, then adding silica particles and a second lysis reagent, with the second lysis reagent comprising a mixture of guanidine thiocyanate, non-ionic detergent, and isopropyl alcohol, under conditions in which DNA is bound to the silica particles. In certain embodiments, the non-ionic detergents in the first lysis reagent and the second lysis reagent are the same or different, and are selected from, e.g., polyethylene glycol sorbitan monolaurate (Tween-20), octylphenoxypolyethoxyethanol (Nonidet P-40), and octylphenoxy poly(ethyleneoxy) ethanol, branched (IGEPAL CA-630).

The method further comprises separating the silica particle with bound DNA from the mixture, washing the separated silica particles with bound DNA with a first wash solution comprising guanidine hydrochloride or guanidine thiocyanate and ethyl alcohol, separating the silica particles with bound DNA from the first wash solution and washing the silica particles with bound DNA with a second wash solution comprising a buffer, e.g., Tris pH 8.0 and ethyl alcohol. In preferred embodiments, the silica particles with bound DNA are washed multiple times, e.g., 2 to 6 times, with the second wash buffer. In particularly preferred embodiments, each wash uses a smaller volume of the second wash buffer than the prior wash with that buffer. In some embodiments the washed silica particles are separated from the last wash buffer treatment and the DNA is eluted from the silica particles, e.g., with an elution buffer, such as 10 mM Tris-HCl pH 8.0, 0.1 mM EDTA. In preferred embodiments, the silica particles with bound DNA are dried, e.g., by heating to about 70° C., prior to elution of the DNA.

The technology is not limited to any particular sample size, but it finds particular application in samples in which low-copy targets are present in large samples. For example, in some embodiments, the bisulfite treated DNA is prepared from a body fluid, e.g., a plasma sample, having a starting volume of at least one mL, preferably at least 5 mL, more preferably at least 10 mL, and/or wherein said volume x of the sample of bisulfite treated DNA is at least 10 µl, preferably at least 25 µl, more preferably at least 50 µl, more preferably at least 100 µl. In preferred embodiments, the volume of treated DNA sample that is present in the pre-amplification reaction is at least 5%, preferably at least 10%-60%, preferably 15%-55%, more preferably about 20%-50% of the total volume of the amplification reaction.

The invention is not limited to a particular number of fractions into which the sample is divided. In some embodiments, n (the number of fractions) is at least 3, preferably at least 5, more preferably at least 10, more preferably at least 20, more preferably at least 100.

In some embodiments, the technology provides a method for analyzing multiple target nucleic acids in a sample using a PCR pre-amplification and a PCR-flap assay, the method comprising:
a) providing bisulfite-treated DNA (in preferred embodiments, comprising human DNA) comprising a plurality of different target regions in a first reaction mixture comprising PCR amplification reagents, wherein said PCR amplification reagents comprise:
  i) a plurality of different primer pairs for amplifying said plurality of different target regions, if present in said sample, from said bisulfite-treated DNA;
  ii) thermostable DNA polymerase;
  iii) dNTPs; and
  iv) a buffer comprising $Mg^{++}$
b) exposing said first reaction mixture to thermal cycling conditions wherein a plurality of different target regions, if present in the sample, are amplified to produce a pre-amplified mixture, and wherein said thermal cycling conditions are limited to a number of thermal cycles that maintain amplification in an exponential range, preferably fewer than 20, more preferably fewer than 15, more preferably 10 or fewer thermal cycles;
c) partitioning said pre-amplified mixture into a plurality of PCR-flap assay reaction mixtures, wherein each PCR-flap assay reaction mixture comprises:
  i) an additional amount of a primer pair selected from said plurality of different primer pairs of step a) i);
  ii) thermostable DNA polymerase;
  iii) dNTPs;
  iv) said buffer comprising $Mg^{++}$
  v) a flap endonuclease, preferably a FEN-1 endonuclease;
  vi) a flap oligonucleotide, and
  vi) a hairpin oligonucleotide comprising a region that is complimentary to a portion of said flap oligonucleotide, preferably a FRET cassette oligonucleotide;

and
d) detecting amplification of one or more different target regions from said bisulfite-treated DNA during PCR-flap assay reactions by detecting cleavage of said hairpin oligonucleotide by said flap endonuclease.

In preferred embodiments, the FEN-1 endonuclease is a thermostable FEN-1, preferably from an archaeal organism, e.g., Afu FEN-1.

In some embodiments, the pre-amplified mixtures described above are diluted with a diluent prior to partitioning into PCR-flap assay reaction mixtures, while in some embodiments, the pre-amplified mixture is added directly to a PCR-flap assay reaction mixture without prior dilution.

In some embodiments, essentially the primers used in the PCR-flap assay reaction are used at the same concentrations at which those particular primers were used in the first reaction mixture, excluding any primers carried over from the first reaction. For example, in some embodiments, the primers in the additional amount of a primer pair added to the PCR-flap assay reaction mixture are added to a concentration such that the concentration of the added primers in the PCR-flap assay (i.e., not counting primers coming from the pre-amplified mixture) is essentially the same as the concentration of the primers of that primer pair in said PCR amplification reagents. In other embodiments, the primers in the additional amount of a primer pair added to the PCR-flap assay reaction mixture are added to a concentration such that the concentration of the added primers in the PCR-flap assay are at a lower or a higher concentration than the concentration of the primers of that primer pair in the first reaction mixture.

While the method is not limited to a particular concentration of $Mg^{++}$ in the buffer used in said first reaction mixture and in the PCR-flap assay reaction mixture, in preferred embodiments, the buffer comprises at least 3 mM $Mg^{++}$, preferably greater than 4 mM $Mg^{++}$, more preferably greater than 5 mM $Mg^{++}$, more preferably greater than 6 mM $Mg^{++}$, more preferably between approximately 7 mM and 7.5 mM $Mg^{++}$. In certain embodiments, the buffer contains less than about 1 mM KCl. In preferred embodiments, the buffer comprises 10 mM 3-(n-morpholino) propanesulfonic acid (MOPS) buffer and 7.5 mM $MgCl_2$.

In some embodiments, the first reaction mixture and/or said plurality of PCR-flap assay reaction mixtures comprise exogenous non-target DNA, preferably bulk fish DNA.

In some embodiments, the thermostable DNA polymerase is a eubacterial DNA polymerase, preferably from genus *Thermus*, more preferably from *Thermus aquaticus*. In some embodiments, the DNA polymerase is modified for hot start PCR, e.g., though the use of a reagent, e.g., an antibody, chemical adduct, etc., such that the DNA polymerase is activated upon heating.

In certain embodiments, the bisulfite-treated DNA comprises human DNA, and the plurality of different target regions comprises target regions selected from the group consisting of SFMBT2, VAV3, BMP3, and NDRG4. In some embodiments, a plurality of different primer pairs are directed to at least two, preferably at least three, more preferably all four of these target regions.

In some embodiments, the plurality of different target regions comprise a reference target region, and in certain preferred embodiments, the reference target region comprises β-actin and and/or ZDHHC1, and/or B3GALT6.

In some embodiments, at least one of the plurality of different primer pairs is selected to produce an amplicon from a target region that is less than about 100 base pairs long, preferably less than about 85 base pairs long. In certain preferred embodiments, all of the different primer pairs are selected to produce an amplicon from a target region that is less than about 100 base pairs long.

In some embodiments, methods provided herein are directed to amplifying substantially all of the bisulfite-treated DNA produced during the process of a sample, e.g., a sample of bodily fluid. In some embodiments, the preparation of bisulfite treated DNA constitutes a substantial fraction of the first reaction mixtures, e.g., in some embodiments, the volume of the sample comprising bisulfite-treated DNA in the first reaction mixture constitutes at least 20-50% of the total volume of the first reaction mixture. For example, in some embodiments, the volume of bisulfite-treated DNA in the first reaction mixture is at least 5%, preferably at least 10%-60%, preferably 15%-55%, more preferably between about 20%-50% of the total volume of the first reaction mixture.

In some embodiments, methods of the technology provide a method for analyzing multiple target nucleic acids in a sample of human plasma using a PCR pre-amplification and a PCR-flap assay, the method comprising:
a) providing bisulfite-treated DNA prepared from at least 1 mL of plasma, the bisulfite treated DNA comprising a plurality of different target regions in a first reaction mixture comprising PCR amplification reagents, wherein said PCR amplification reagents comprise:
i) a plurality of different primer pairs for amplifying said plurality of different target regions, said target regions selected from SFMBT2, VAV3, BMP3, and NDRG4, if present in said sample, from said bisulfite-treated DNA, wherein each of said plurality of different primer pairs is selected to produce an amplicon from a target region that is less than about 100 base pairs long;
ii) DNA polymerase from *Thermus aquaticus*;
iii) dNTPs; and
iv) a buffer comprising 7.5 mM $Mg^{++}$
b) exposing said first reaction mixture to thermal cycling conditions wherein a plurality of different target regions, if present in the sample, are amplified to produce a pre-amplified mixture, and wherein said thermal cycling conditions are limited to a number of thermal cycles that maintain amplification in an exponential range, preferably fewer than 20, more preferably fewer than 15, more preferably 10 or fewer thermal cycles;
c) partitioning said pre-amplified mixture into a plurality of PCR-flap assay reaction mixtures, wherein each PCR-flap assay reaction mixture comprises:
i) an additional amount of a primer pair selected from said plurality of different primer pairs of step a) i);
ii) DNA polymerase from *Thermus aquaticus*;
iii) dNTPs;
iv) said buffer comprising 7.5 mM $Mg^{++}$
v) a thermostable FEN-1 flap endonuclease;
vi) a flap oligonucleotide, and
vi) a FRET cassette oligonucleotide comprising a region that is complimentary to a portion of said flap oligonucleotide;

and
d) detecting amplification of one or more the different target regions selected from SFMBT2, VAV3, BMP3, and NDRG4 during PCR-flap assay reactions.

In preferred embodiments, the plurality of different target regions comprise a reference target region, preferably comprising comprises β-actin and/or ZDHHC1. In certain embodiments, one or more of the target regions and/or primers pairs is selected from the target regions and primer pairs depicted in FIGS. 5A-5F.

Also provided herein are improved methods for isolating DNA, e.g., cell-free DNA from blood or blood fractions, e.g., plasma or serum. For example, embodiments provide methods of processing a plasma sample, the method comprising combining the plasma sample with a protease and a first lysis reagent that comprises guanidine thiocyanate and non-ionic detergent to form a mixture in which proteins are digested by the protease, then adding mixable silica particles and a second lysis reagent, with the second lysis reagent comprising a mixture of guanidine thiocyanate, non-ionic detergent, and isopropyl alcohol, under conditions in which DNA is bound to the silica particles. In certain embodiments, the non-ionic detergents in the first lysis reagent and the second lysis reagent are the same or different, and are selected from, e.g., polyethylene glycol sorbitan monolaurate (Tween-20), octylphenoxypolyethoxyethanol (Nonidet P-40), and octylphenoxy poly(ethyleneoxy) ethanol, branched (IGEPAL CA-630). In certain preferred embodiments, the silica particles are magnetic particles.

The method further comprises separating the silica particles with bound DNA from the mixture, washing the separated silica particles with bound DNA with a first wash solution comprising guanidine hydrochloride or guanidine thiocyanate and ethyl alcohol, separating the silica particles with bound DNA from the first wash solution and washing the silica particles with bound DNA with a second wash solution comprising a buffer, e.g., Tris pH 8.0, and ethyl alcohol. In preferred embodiments, the silica particles with bound DNA are washed multiple times, e.g., 2 to 6 times, with the second wash buffer. In particularly preferred embodiments, each wash uses a smaller volume of the second wash buffer than the prior wash with that buffer. In some embodiments the washed silica particles are separated from the last wash buffer treatment and the DNA is eluted from the silica particles, e.g., with water or with an elution buffer, such as 10 mM Tris-HCl pH 8.0, 0.1 mM EDTA. In preferred embodiments, the silica particles with bound DNA are dried after the last wash step, e.g., by heating (to, for example, 37° C. to 75° C., preferably about 45° C. to 70° C., more preferably about 70° C.), prior to elution of the DNA.

During development of the technology it was discovered that use two different lysis reagents, added at different times in the procedure, improves yield of DNA from plasma. In preferred embodiments, an aliquot of the second lysis reagent is added after the mixture comprising the first lysis reagent and protease have incubated, e.g., for about 5 to 60 minutes, preferably 30 to 60 minutes, at room temperature to 55° C. In preferred embodiments, the mixture is incubated at room temperature. In certain embodiments, the first lysis reagent comprises guanidine thiocyanate and a non-ionic detergent, and the second lysis reagent comprises guanidine thiocyanate, a non-ionic detergent, and an alcohol. In preferred embodiments, the first lysis reagent comprises about 4.3 M guanidine thiocyanate and 10% w:v IGEPAL CA-630, and in some embodiments, the second lysis reagent comprises 4.3 M guanidine thiocyanate and 10% w:v IGEPAL CA-630 combined with isopropyl alcohol.

During development of the technology it was discovered that use two different wash solutions at different steps in the procedure improved yield of DNA from plasma. In some embodiments, a first wash solution, used as described above, comprises guanidine hydrochloride or guanidine thiocyanate and ethyl alcohol, and the second wash solution comprises a buffer and ethyl alcohol. In particularly preferred embodiments, the first wash solution comprises about 3 M guanidine hydrochloride or guanidine thiocyanate and about 57% ethyl alcohol and the second wash solution, used as described above, comprises about 80% ethyl alcohol and about 20% 10 mM Tris pH 8.0 buffer.

In particularly preferred embodiments, all lysis steps and wash steps are conducted at room temperature.

In some embodiments, the plasma sample is mixed with a DNA process control, e.g., a DNA that does not cross-react with assays configured to detect DNA found in the plasma sample. For example, in some embodiments the plasma is human plasma and the DNA process control comprises a zebrafish RASSF1 sequence. In preferred embodiments, the DNA process control is synthetic DNA, e.g., a synthetic DNA fragment comprising a zebrafish RASSF1 sequence. In particularly preferred embodiments, the DNA process control is double stranded. In preferred embodiments, the process control is added to the plasma sample prior to extraction of DNA from the sample, e.g., along with the first or second lysis reagent additions.

In some embodiments, bulk exogenous DNA, e.g., DNA that does not cross-react with assays configured to detect DNA found in the plasma sample, is added to the plasma sample. For example, in preferred embodiments, the plasma is human plasma and bulk fish DNA, e.g., genomic DNA from salmon, is added to the sample.

Embodiments of the methods provided herein find particular use in the processing of relatively large plasma samples, e.g., greater than 1 mL. In preferred embodiments, the plasma sample has a volume of at least 2 mL, 3 mL, 4 mL, 5 mL, 6 mL, 7 mL, 8 mL, 9 mL, or at least 10 mL, or any fractional volume therebetween. In some embodiments the plasma sample is greater than 10 mL in volume.

In some embodiments, the method further comprises analyzing the isolated DNA sample for particular target nucleic acids. In preferred embodiments, the method comprises analyzing the isolated DNA for a plurality of methylated target nucleic acids, the method comprising treating the isolated DNA sample with bisulfite to produce a bisulfite-treated DNA sample, treating the bisulfite-treated DNA sample to an amplification reaction under conditions wherein a plurality of different target regions (e.g., 2, 3, 4, 5, etc. target regions), if present in the sample, are amplified to form an amplified mixture.

In certain preferred embodiments the method further comprises partitioning the amplified mixture into a plurality of different detection assay reaction mixtures and conducting a plurality of different detection assays with the detection assay reaction mixtures, wherein the plurality of different target regions, if present in the sample, are detected in one or more of the plurality of different detection assay reaction mixtures. In preferred embodiments, the plurality of different target regions comprises at least 5 different target regions.

Provided herein are kits and systems for performing methods described herein. In some embodiments the technology provides a kit for isolating DNA from plasma, the kit comprising, e.g.:
  a) a first lysis reagent comprising guanidine thiocyanate and a non-ionic detergent or components for preparing the first lysis reagent;
  b) a second lysis reagent comprising guanidine thiocyanate, a non-ionic detergent, and isopropanol, or components for preparing the second lysis reagent;
  c) a first wash solution comprising guanidine hydrochloride or guanidine thiocyanate and ethyl alcohol, or components for preparing the first wash solution;

d) a second wash solution comprising Tris buffer and ethyl alcohol, or components for preparing the second wash solution; and e) silica particles.

In preferred embodiments, the non-ionic detergent comprises IGEPAL CA-630. In some embodiments, the silica particles are magnetic particles, and in particularly preferred embodiments, the kit comprises a magnet, e.g., for separating the particles during steps of the procedure. In some embodiments, the kit further comprises an elution buffer or components for preparing the elution buffer.

In some embodiments the kit further comprises a DNA process control, e.g., a DNA process control comprising a zebrafish RASSF1 sequence. In some embodiments the kit further comprises a preparation of bulk fish DNA, and in particularly preferred embodiments, the DNA process control is in a preparation of bulk fish DNA.

In some embodiments the technology provides a system for processing a plasma sample, the system comprising:
a) a first lysis reagent comprising guanidine thiocyanate and a non-ionic detergent or components for preparing the first lysis reagent;
b) a second lysis reagent comprising guanidine thiocyanate, a non-ionic detergent, and isopropanol, or components for preparing the second lysis reagent;
c) a first wash solution comprising guanidine hydrochloride or guanidine thiocyanate and ethyl alcohol, or components for preparing the first wash solution;
d) a second wash solution comprising Tris buffer and ethyl alcohol, or components for preparing the second wash solution; and
e) silica particles.

In preferred embodiments, the non-ionic detergent comprises IGEPAL CA-630.

In some embodiments the system further comprises an elution buffer or components for preparing said elution buffer.

In some embodiments the system further comprises a DNA process control, e.g., a DNA process control comprising a zebrafish RASSF1 sequence. In some embodiments the system further comprises a preparation of bulk fish DNA, and in particularly preferred embodiments, the DNA process control is in a preparation of bulk fish DNA.

In some embodiments, the system further comprises one or more of: a magnet, a vessel for processing plasma, and/or a vessel or plate for receiving purified DNA. In some embodiments, the system comprises a device for performing all or part of the steps, e.g., a device such as a STARlet automated platform.

In some embodiments, the system further comprises reagents for analysis of DNA isolated from plasma. For example, in certain embodiments, the system comprises reagents for treating DNA with bisulfite to produce bisulfite-treated DNA, e.g., a bisulfite reagent, a desulfonation reagent, and materials for purifying bisulfite-treated DNA (e.g., silica beads, a binding buffer, a solution comprising bovine serum albumin and/or casein, e.g., as described in U.S. Pat. No. 9,315,853, incorporated herein by reference).

In preferred embodiments, the system further comprises DNA analysis reagents, e.g., PCR amplification reagents and/or flap assay reagents. In particularly preferred embodiments, the system comprises PCR amplification reagents comprising:
i) a plurality of different primer pairs for amplifying a plurality of different target regions, if present in said plasma;
ii) thermostable DNA polymerase;
iii) dNTPs; and
iv) a buffer comprising $Mg^{++}$ In some embodiments, the system further comprises PCR-flap assay reagents. In certain preferred embodiments, the PCR flap assay reagents comprise:
i) a plurality of different primer pairs for amplifying a plurality of different target regions, if present in said plasma;
ii) thermostable DNA polymerase;
iii) dNTPs;
iv) a buffer comprising $Mg^+$
v) a flap endonuclease;
vi) a flap oligonucleotide, and
vi) a hairpin oligonucleotide comprising a region that is complimentary to a portion of said flap oligonucleotide.

In still further embodiments, the system comprises a thermal cycler for conducting PCR amplification and/or PCR flap assay reactions. In preferred embodiments, the thermal cycler is configured to detect signal, e.g., fluorescence, during the course of amplification reactions conducted with the assay reagents.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIGS. 5A-5F show nucleic acid sequences for analysis of methylation using the combination of bisulfite conversion, pre-amplification, and PCR-flap assay detection. Each panel shows one strand of the DNA target region prior to bisulfite treatment and the expected sequence of that region upon conversion with bisulfite reagent, with converted unmethylated C residues shown as 'T's. The primer binding sites for outer primers and for PCR-flap assay inner primers (as would be used for a nested assay design) are shown boxed. Each figure also shows an alignment of the PCR-flap assay primers and flap probe on a segment of the converted sequence. FIGS. 5A-5F show target regions of markers SFMBT2, VAV3, BMP3, NDRG4, and reference DNAs β-actin, and ZDHHC1, respectively. The 'arms' on the flap oligonucleotides used in the PCR-flap assay are as follows: Arm 1 is 5'-CGCCGAGG-3'; Arm 3 is 5'-GACGCGGAG-3'; and Arm 5 is 5'-CCACGGACG-3'.

FIG. 6 shows a table comparing detection of the indicated bisulfite-treated target DNAs pre-amplified using outer primers for different numbers of cycles, followed by PCR-flap assay amplification and detection using nested (inner) primers. Comparative assays used a QuARTS PCR-flap assay directly on the bisulfite-treated DNA, without pre-amplification.

FIG. 7 compares results using nested or non-nested amplification primer configurations as shown in FIGS. 5A-5F, and compares different primer concentrations and different buffers in the PCR pre-amplification step, as described in Example 3.

FIGS. 8A-8C show the results of using different numbers of cycles in the pre-amplification phase of the assay. FIG. 8A shows the number of strands expected for each of the target types in normal plasma samples or in plasma samples spiked with known amounts of target DNAs, with either no pre-amplification, or with 5, 10, 20 or 25 cycles of amplification. FIG. 8B compares the number of strands detection in each reaction under the conditions show, as described in Example 4.

FIG. 9 shows the results of using a non-nested multiplex pre-amplification on DNA isolated from stool, as described in Example 5.

FIGS. 10A-10I show the results of using a non-nested multiplex pre-amplification on DNA isolated from plasma, as described in Example 6.

FIGS. 11A-11C show graphs comparing different plasma isolation conditions on the yield of β-actin DNA (untreated and bisulfite converted after extraction) and the B3GALT6 gene (bisulfite converted after extraction, as described in Example 8.

FIGS. 13A-13F show a table of nucleic acid sequences relating to embodiments herein.

Figure 1:
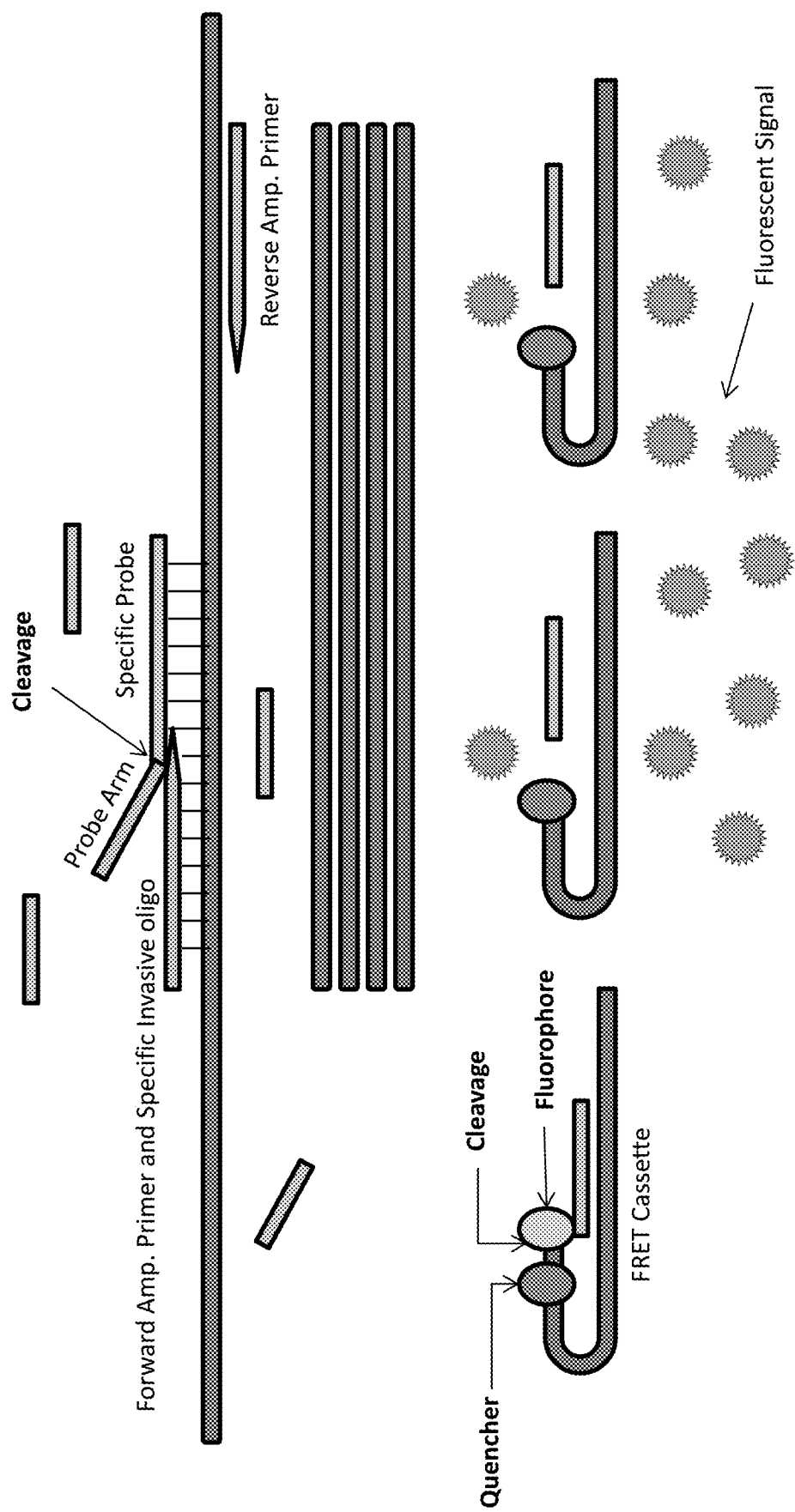
FIG. 1 provides a schematic diagram of a combined PCR-invasive cleavage assay ("PCR-flap assay"), e.g., a QuARTS assay.
Figure 2:
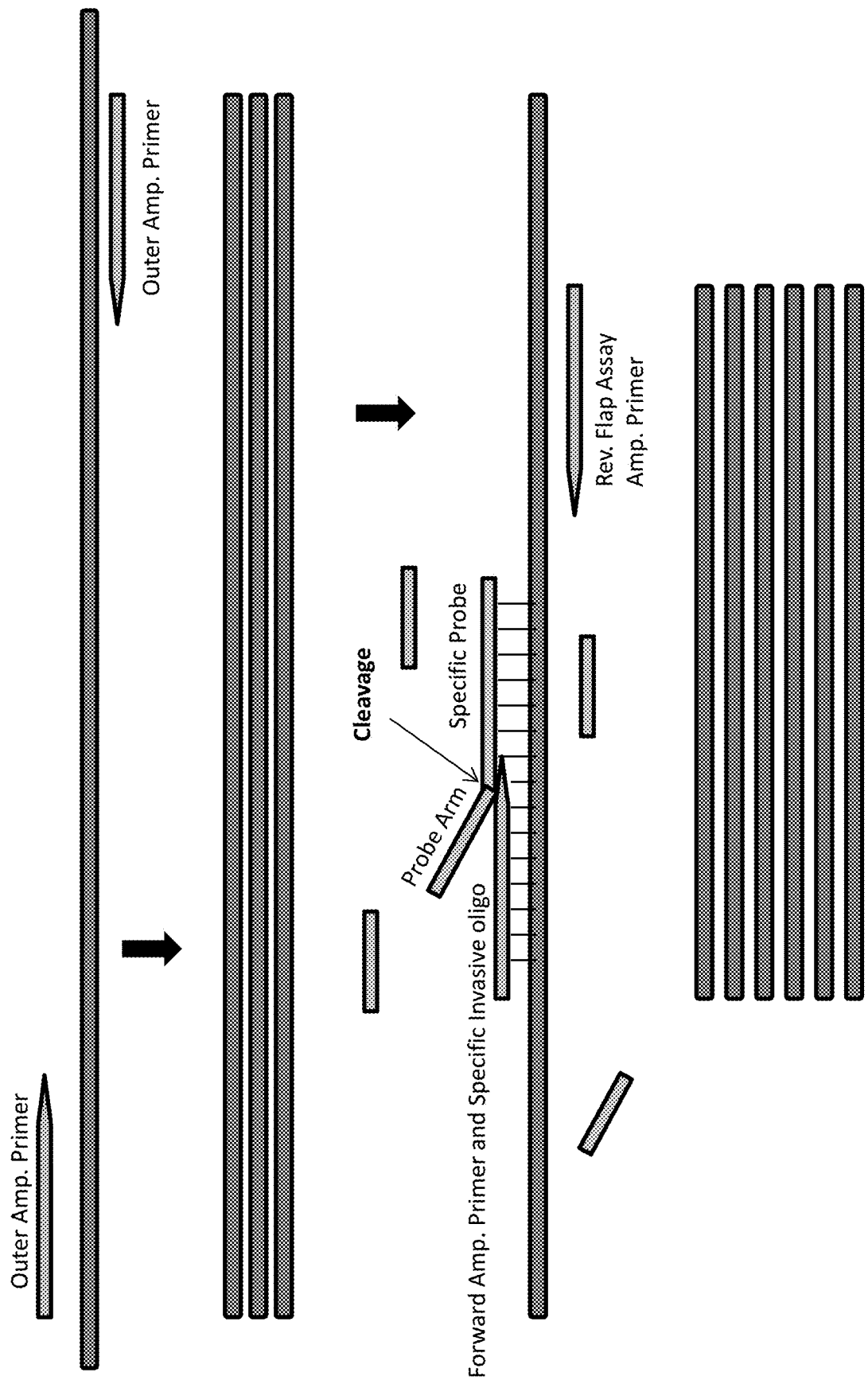
FIG. 2 provides a schematic diagram of nested PCR combined with a PCR-flap assay, showing a first amplification (or pre-amplification) using outer primers, followed by a PCR-flap assay using a second pair of primers having binding sites within the sites of the outer primers. The smaller amplicon produced in the second amplification is shown at the bottom. The FRET-cassette portion of the reaction is not shown.
Figure 3:
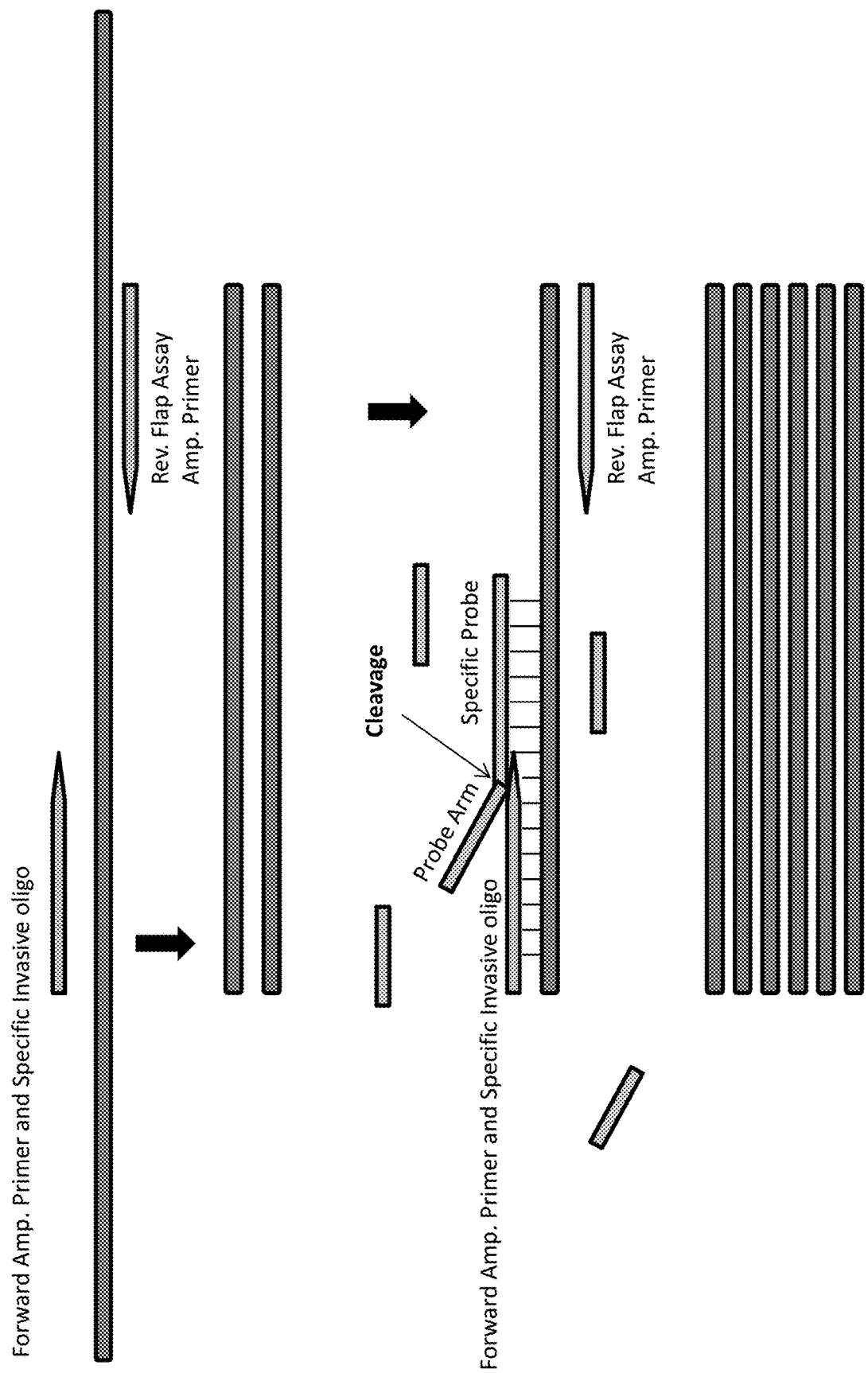
FIG. 3 provides a schematic diagram of a PCR pre-amplification followed by a PCR-flap assay in which the pre-amplification and the PCR-flap assay use the same primer pair, and producing copies of the same amplicon. The FRET-cassette portion of the reaction is not shown.
Figure 4:
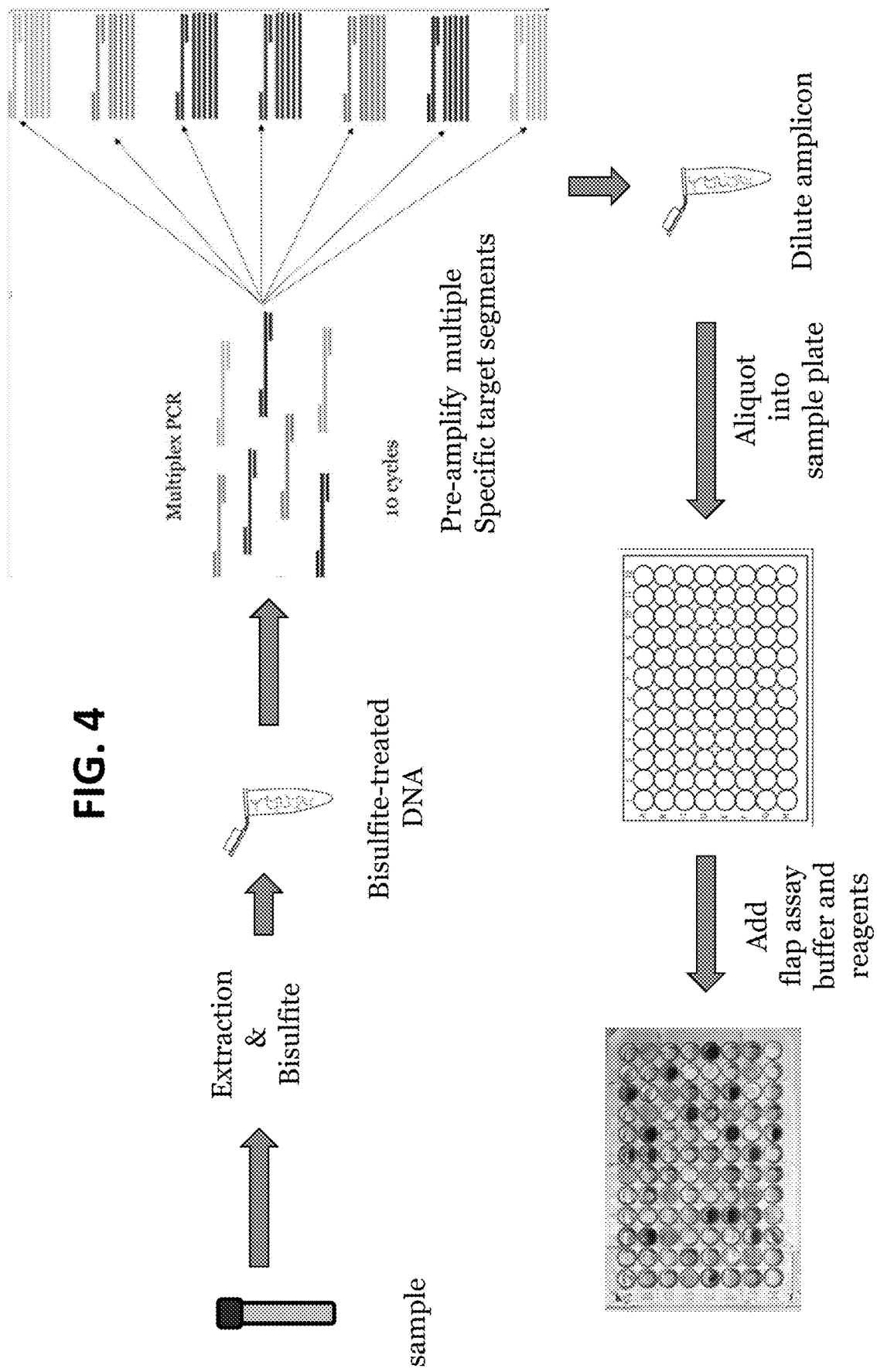
FIG. 4 provides a schematic diagram of a multiplex pre-amplification in which a plurality of different target regions in a sample are amplified in a single multiplexed PCR reaction containing primer pairs for each of the different target regions, followed by individual PCR-flap assay reactions in which each PCR flap assay uses only the primer pair specific for the target locus to be detected in the final PCR-flap assay reaction.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on." The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein in reference to non-target DNA, the term "exogenous" refers to non-target DNA that is isolated and purified from a source other than the source or sample containing the target DNA. For example, purified fish DNA is exogenous DNA with respect to a sample comprising human target DNA, e.g., as described in U.S. Pat. No. 9,212,392, which is incorporated herein by reference. Exogenous DNA need not be from a different organism than the target DNA. For example, purified fish DNA obtained commercially would be exogenous if added to a reaction configured to detect a target nucleic acid in a sample from a particular fish. In preferred embodiments, exogenous DNA is selected to be undetected by an assay configured to detect and/or quantify the target nucleic acid in the reaction in to which the exogenous DNA is added.

As used herein, a "DNA fragment" or "small DNA" or "short DNA" means a DNA that consists of no more than approximately 200 base pairs or nucleotides in length.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically. In some embodiments, an oligonucleotide primer is used with a template nucleic acid and extension of the primer is template dependent, such that a complement of the template is formed.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S.

Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al., (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the "INVADER" flap assay, or invasive cleavage assay, (Hologic, Inc.) described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and in combined PCR/invasive cleavage assays (Hologic, Inc., e.g., in U.S. Patent Publications 2006/0147955 and 2009/0253142), each of which is herein incorporated by reference in its entirety for all purposes); enzyme mismatch cleavage methods (e.g., Variagenics, U.S. Pat. Nos. 6,110,684, 5,958, 692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication 20090253142 A1 (application Ser. No. 12/404,240), incorporated herein by reference in its entirety for all purposes, and as diagrammed in FIG. 1. Because many copies of the FRET cassette are cleaved for each copy of the target amplicon produced, the assay is said to produce "signal amplification" in addition to target amplification. Additional amplification plus invasive cleavage detection configurations, termed the QuARTS method, are described in U.S. Pat. Nos. 8,361,720, 8,715, 937, and 8,916,344, incorporated herein by reference in their entireties for all purposes.

As used herein, the term "PCR-flap assay" is used interchangeably with the term "PCR-invasive cleavage assay" and refers to an assay configuration combining PCR target amplification and detection of the amplified DNA by formation of a first overlap cleavage structure comprising amplified target DNA, and a second overlap cleavage structure comprising a cleaved 5' flap from the first overlap cleavage structure and a labeled hairpin detection oligonucleotide called a "FRET cassette". In the PCR-flap assay as used herein, the assay reagents comprise a mixture containing DNA polymerase, FEN-1 endonuclease, a primary probe comprising a portion complementary to a target nucleic acid, and a hairpin FRET cassette, and the target nucleic acid is amplified by PCR and the amplified nucleic acid is detected simultaneously (i.e., detection occurs during the course of target amplification). PCR-flap assays include the QuARTS assays described in U.S. Pat. Nos. 8,361,720; 8,715,937; and 8,916,344, and the amplification assays of U.S. Pat. No. 9,096,893 (for example, as diagrammed in FIG. 1 of that patent), each of which is incorporated herein by reference in its entirety.

As used herein, the term "PCR-flap assay reagents" refers to one or more reagents for detecting target sequences in a PCR-flap assay, the reagents comprising nucleic acid molecules capable of participating in amplification of a target nucleic acid and in formation of a flap cleavage structure in the presence of the target sequence, in a mixture containing DNA polymerase, FEN-1 endonuclease and a FRET cassette.

As used herein, the term "flap assay reagents" or "invasive cleavage assay reagents" refers to all reagents that are required for performing a flap assay or invasive cleavage assay on a substrate. As is known in the art, flap assays generally include an invasive oligonucleotide, a flap oligonucleotide, a flap endonuclease and, optionally, a FRET cassette, as described above. Flap assay reagents may optionally contain a target to which the invasive oligonucleotide and flap oligonucleotide bind.

As used herein, the term "flap oligonucleotide" refers to an oligonucleotide cleavable in a detection assay, such as an invasive cleavage assay, by a flap endonuclease. In preferred embodiments, a flap oligonucleotide forms an invasive cleavage structure with other nucleic acids, e.g., a target nucleic acid and an invasive oligonucleotide.

As used herein, the term "FRET cassette" refers to a hairpin oligonucleotide that contains a fluorophore moiety and a nearby quencher moiety that quenches the fluorophore. Hybridization of a cleaved flap (e.g., from cleavage of a target-specific probe in a PCR-flap assay) with a FRET cassette produces a secondary substrate for the flap endonuclease, e.g., a FEN-1 enzyme. Once this substrate is formed, the 5' fluorophore-containing base is cleaved from the cassette, thereby generating a fluorescence signal. In preferred embodiments, a FRET cassette comprises an unpaired 3' portion to which a cleavage product, e.g., a portion of a cleaved flap oligonucleotide, can hybridize to from an invasive cleavage structure cleavable by a FEN-1 endonuclease.

A nucleic acid "hairpin" as used herein refers to a region of a single-stranded nucleic acid that contains a duplex (i.e., base-paired) stem and a loop, formed when the nucleic acid comprises two portions that are sufficiently complementary to each other to form a plurality of consecutive base pairs.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor flurophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FEN-1" in reference to an enzyme refers to a non-polymerase flap endonuclease from a eukaryote or archaeal organism, as encoded by a FEN-1 gene. See, e.g., WO 02/070755, and Kaiser M. W., et al. (1999) J. Biol. Chem., 274:21387, which are incorporated by reference herein in their entireties for all purposes.

As used herein, the term "FEN-1 activity" refers to any enzymatic activity of a FEN-1 enzyme.

As used herein, the term "primer annealing" refers to conditions that permit oligonucleotide primers to hybridize to template nucleic acid strands. Conditions for primer annealing vary with the length and sequence of the primer and are generally based upon the $T_m$ that is determined or calculated for the primer. For example, an annealing step in an amplification method that involves thermocycling involves reducing the temperature after a heat denaturation step to a temperature based on the $T_m$ of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "abundance of nucleic acid" refers to the amount of a particular target nucleic acid sequence present in a sample or aliquot. The amount is generally referred to in terms of mass (e.g., µg), mass per unit of volume (e.g., µg/µL); copy number (e.g., 1000 copies, 1 attomole), or copy number per unit of volume (e.g., 1000 copies per mL, 1 attomole per µL). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions prior to incubation or, in the case of PCR, in the initial cycles, in which there is little change in signal.

The term "$C_t$" or "threshold cycle" as used herein in reference to real time detection during an amplification reaction that is thermal cycled refers to the fractional cycle number at which the detected signal (e.g., fluorescence) passes the fixed threshold.

The term "no template control" and "no target control" (or "NTC") as used herein in reference to a control reaction refers to a reaction or sample that does not contain template or target nucleic acid. It is used to verify amplification quality.

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

A sample "suspected of containing" a nucleic acid may contain or not contain the target nucleic acid molecule.

As used herein, the term "sample" is used in its broadest sense. For example, in some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin. Samples may be unpurifed or may be partially or completely purified or otherwise processed.

The present technology is not limited by the type of biological sample used or analyzed. The present technology is useful with a variety of biological samples including, but not limited to, tissue (e.g., organ (e.g., heart, liver, brain, lung, stomach, intestine, spleen, kidney, pancreas, and reproductive organs), glandular, skin, and muscle), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc.), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, pinnipeds, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair, and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Samples may be prepared by any desired or suitable method. In some embodiments, nucleic acids are analyzed directly from bodily fluids, stool, or other samples using the methods described in U.S. Pat. No. 9,000,146, which is herein incorporated by reference in its entirety for all purposes.

The above described examples are not, however, to be construed as limiting the sample (e.g., suspected of comprising a target sequence, gene or template (e.g., the presence or absence of which can be determined using the compositions and methods of the present technology)) types applicable to the present technology.

The terms "nucleic acid sequence" and "nucleic acid molecule" as used herein refer to an oligonucleotide, nucleotide or polynucleotide, and fragments or portions thereof. The terms encompass sequences that include analogs of DNA and RNA nucleotides, including those listed above, and also including, but not limited to, 4-acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, and pyrazolo[3,4-d]pyrimidines such as guanine analogue 6 amino 1H-pyrazolo[3,4d]pyrimidin 4(5H) one (ppG or PPG, also Super G) and the adenine analogue 4 amino 1H-pyrazolo[3,4d]pyrimidine (ppA or PPA). The xanthine analogue 1H-pyrazolo[5,4d]pyrimidin 4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the technology. Other modified bases useful in the present technology include 6-amino-3-prop-1-ynyl-5-hydropyrazolo[3,4-d]pyrimidine-4-one, PPPG; 6-amino-3-(3-hydroxyprop-1-yny)1-5-hydropyrazolo[3,4- d]pyrimidine-4-one, HOPPPG; 6-amino-3-(3-aminoprop-1-ynyl)-5-hydropyrazolo[3,4-d]pyrimidine-4-one, NH2PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl) pyrazolo[3,4-d]pyrimidine, $NH_2$ PPPA; 3-prop-1-ynylpyrazolo[3,4-d]pyrimidine-4,6-diamino, $(NH_2)_2$ PPPA; 2-(4,6-diaminopyrazolo[3,4-d]pyrimidin-3-yl)ethyn-1-ol, $(NH_2)_2$ PPPAOH; 3-(2-aminoethynyl)pyrazolo[3,4-d]pyrimidine-4,6-diamine, $(NH_2)_2$ PPPANH$_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, $NH_2$PC; 5-[4-amino-3-(3-methoxyprop-1-ynyl) pyrazol[3,4-d]pyrimidinyl]-2-(hydroxymethyl)oxolan-3-ol, $CH_3$ OPPPA; 6-amino-1-[4-hydroxy-5-(hydroxymethyl) oxolan-2-yl]-3-(3-methoxyprop-1-ynyl)-5-hydropyrazolo [3,4-d]pyrimidin-4-one, $CH_3$ OPPPG; 4, (4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo [3,4-d]pyrimidine-4-one; 5-(4-hydroxy-but-1-ynyl)-1H-pyrimidine-2,4-dione, Super T; 3-iodo-1H-pyrazolo[3,4-d]pyrimidine-4,6-diamine ($(NH_2)_2$PPAI); 3-bromo-1H-pyrazolo [3,4-d]pyrimidine-4,6-diamine ($(NH_2)_2$ PPABr); 3-chloro-1H-pyrazolo[3,4-d]pyrimidine-4,6-diamine ($(NH_2)_2$PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

A nucleic acid sequence or molecule may be DNA or RNA, of either genomic or synthetic origin, that may be single or double stranded, and represent the sense or antisense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, microRNA, or protein nucleic acid (PNA).

The present technology is not limited by the type or source of nucleic acid (e.g., sequence or molecule (e.g. target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

The terms "nucleotide" and "base" are used interchangeably when used in reference to a nucleic acid sequence, unless indicated otherwise herein. A "nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, LO), all herein incorporated by reference in their entireties.

The term "oligonucleotide" as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer (e.g., oligonucleotides are typically less than 200 residues long (e.g., between 15 and 100 nucleotides), however, as used herein, the term is also intended to encompass longer polynucleotide chains). The exact size will depend on many factors, which in turn depend on the ultimate function or use of the oligonucleotide. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

As used herein, the terms "complementary" or "complementarity" are used in reference to polynucleotides (e.g., a sequence of two or more nucleotides (e.g., an oligonucleotide or a target nucleic acid)) related by the base-pairing rules. For example, the sequence "5'-A-G-T-3'," is complementary to the sequence "3'-T-C-A-5'." Complementarity may be "partial," in which only some of the nucleic acid bases are matched according to the base pairing rules. Or, there may be "complete" or "total" complementarity between the nucleic acid bases. The degree of complementarity between nucleic acid strands has significant effects on the efficiency and strength of hybridization between nucleic acid strands. This is of particular importance in amplification reactions, as well as detection methods that depend upon the association of two or more nucleic acid strands. Either term may also be used in reference to individual nucleotides, especially within the context of polynucleotides. For example, a particular nucleotide within an oligonucleotide may be noted for its complementarity, or lack thereof, to a nucleotide within another nucleic acid sequence (e.g., a target sequence), in contrast or comparison to the complementarity between the rest of the oligonucleotide and the nucleic acid sequence.

The complement of a nucleic acid sequence as used herein refers to an oligonucleotide which, when aligned with the nucleic acid sequence such that the 5' end of one sequence is paired with the 3' end of the other, is in "antiparallel association." Nucleotide analogs, as discussed above, may be included in the nucleic acids of the present technology and include. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "label" refers to any moiety (e.g., chemical species) that can be detected or can lead to a detectable response. In some preferred embodiments, detection of a label provides quantifiable information. Labels can be any known detectable moiety, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent compound (e.g., bioluminescent, phosphorescent or chemiluminescent labels) or a fluorescent compound.

A label may be joined, directly or indirectly, to an oligonucleotide or other biological molecule. Direct labeling can occur through bonds or interactions that link the label to the oligonucleotide, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled.

Labels can be used alone or in combination with moieties that can suppress (e.g., quench), excite, or transfer (e.g., shift) emission spectra (e.g., fluorescence resonance energy transfer (FRET)) of a label (e.g., a luminescent label).

A "polymerase" is an enzyme generally for joining 3'-OH 5'-triphosphate nucleotides, oligomers, and their analogs. Polymerases include, but are not limited to, template-dependent DNA-dependent DNA polymerases, DNA-dependent RNA polymerases, RNA-dependent DNA polymerases, and RNA-dependent RNA polymerases. Polymerases include but are not limited to T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9°N DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs), KOD HiFi DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. Nos. 6,329,178; 6,602, 695; and 6,395,524 (incorporated by reference). These polymerases include wild-type, mutant isoforms, and genetically engineered variants.

A "DNA polymerase" is a polymerase that produces DNA from deoxynucleotide monomers (dNTPs). "Eubacterial DNA polymerase" as used herein refers to the Pol A type DNA polymerases (repair polymerases) from Eubacteria, including but not limited to DNA Polymerase I from *E. coli*, Taq DNA polymerase from *Thermus aquaticus* and DNA Pol I enzymes from other members of genus *Thermus*, and other eubacterial species etc.

As used herein, the term "target" refers to a nucleic acid species or nucleic acid sequence or structure to be detected or characterized.

Accordingly, as used herein, "non-target", e.g., as it is used to describe a nucleic acid such as a DNA, refers to nucleic acid that may be present in a reaction, but that is not the subject of detection or characterization by the reaction. In some embodiments, non-target nucleic acid may refer to nucleic acid present in a sample that does not, e.g., contain a target sequence, while in some embodiments, non-target may refer to exogenous nucleic acid, i.e., nucleic acid that does not originate from a sample containing or suspected of containing a target nucleic acid, and that is added to a reaction, e.g., to normalize the activity of an enzyme (e.g., polymerase) to reduce variability in the performance of the enzyme in the reaction.

As used herein, the term "amplification reagents" refers to those reagents (deoxyribonucleoside triphosphates, buffer, etc.), needed for amplification except for primers, nucleic acid template, and the amplification enzyme. Typically, amplification reagents along with other reaction components are placed and contained in a reaction vessel.

As used herein, the term "control" when used in reference to nucleic acid detection or analysis refers to a nucleic acid having known features (e.g., known sequence, known copy-number per cell), for use in comparison to an experimental target (e.g., a nucleic acid of unknown concentration). A control may be an endogenous, preferably invariant gene against which a test or target nucleic acid in an assay can be normalized. Such normalizing controls for sample-to-sample variations that may occur in, for example, sample processing, assay efficiency, etc., and allows accurate sample-to-sample data comparison. Genes that find use for normalizing nucleic acid detection assays on human samples include, e.g., β-actin, ZDHHC1, and B3GALT6 (see, e.g., U.S. patent application Ser. Nos 14/966,617 and 62/364,082, each incorporated herein by reference.

Controls may also be external. For example, in quantitative assays such as qPCR, QuARTS, etc., a "calibrator" or "calibration control" is a nucleic acid of known sequence, e.g., having the same sequence as a portion of an experimental target nucleic acid, and a known concentration or series of concentrations (e.g., a serially diluted control target for generation of calibration curved in quantitative PCR). Typically, calibration controls are analyzed using the same reagents and reaction conditions as are used on an experimental DNA. In certain embodiments, the measurement of the calibrators is done at the same time, e.g., in the same thermal cycler, as the experimental assay. In preferred embodiments, multiple calibrators may be included in a single plasmid, such that the different calibrator sequences are easily provided in equimolar amounts. In particularly preferred embodiments, plasmid calibrators are digested, e.g., with one or more restriction enzymes, to release calibrator portion from the plasmid vector. See, e.g., WO 2015/066695, which is included herein by reference.

As used herein "ZDHHC1" refers to a gene encoding a protein characterized as a zinc finger, DHHC-type containing 1, located in human DNA on Chr 16 (16q22.1) and belonging to the DHHC palmitoyltransferase family.

As used herein, the term "process control" refers to an exogenous molecule, e.g., an exogenous nucleic acid added to a sample prior to extraction of target DNA that can be measured post-extraction to assess the efficiency of the process and be able to determine success or failure modes. The nature of the process control nucleic acid used is usually dependent on the assay type and the material that is being measured. For example, if the assay being used is for detection and/or quantification of double stranded DNA or mutations in it, then double stranded DNA process controls are typically spiked into the samples pre-extraction. Similarly, for assays that monitor mRNA or microRNAs, the process controls used are typically either RNA transcripts or synthetic RNA. See, e.g., U.S. patent application Ser. No. 62/364,049, filed Jul. 19, 2016, which is incorporated herein by reference, and which describes use of zebrafish DNA as a process control for human samples.

As used herein, the term "zebrafish DNA" is distinct from bulk "fish DNA") e.g., purified salmon DNA) and refers to DNA isolated from *Danio rerio*, or created in vitro (e.g., enzymatically, synthetically) to have a sequence of nucleotides found in DNA from *Danio rerio*. In preferred embodiments, the zebrafish DNA is a methylated DNA added as a detectable control DNA, e.g., a process control for verifying DNA recovery through sample processing steps. In particular, zebrafish DNA comprising at least a portion of the RASSF1 gene finds use as a process control, e.g., for human samples, as described in U.S. patent application Ser. No. 62/364,049.

As used herein the term "fish DNA" is distinct from zebrafish DNA and refers to bulk (e.g., genomic) DNA isolated from fish, e.g., as described in U.S. Pat. No. 9,212,392. Bulk purified fish DNA is commercially available, e.g., provided in the form of cod and/or herring sperm DNA (Roche Applied Science, Mannheim, Germany) or salmon DNA (USB/Affymetrix).

As used herein, the terms "particle" and "beads" are used interchangeable, and the terms "magnetic particles" and "magnetic beads" are used interchangeably and refer to particles or beads that respond to a magnetic field. Typically, magnetic particles comprise materials that have no magnetic field but that form a magnetic dipole when exposed to a magnetic field, e.g., materials capable of being magnetized in the presence of a magnetic field but that are not themselves magnetic in the absence of such a field. The term "magnetic" as used in this context includes materials that are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

As used herein, the term "kit" refers to any delivery system for delivering materials. In the context of nucleic acid purification systems and reaction assays, such delivery systems include systems that allow for the storage, transport, or delivery of reagents and devices (e.g., chaotropic salts, particles, buffers, denaturants, oligonucleotides, filters etc. in the appropriate containers) and/or supporting materials (e.g., sample processing or sample storage vessels, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a sub-portion of the total kit components. The containers may be delivered to the intended recipient together or separately. For example, a first container may contain an materials for sample collection and a buffer, while a second container contains capture oligonucleotides and denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a sub-portion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, on recordable media (e.g., diskette, CD, flash drive, etc.). In some embodiments, instructions direct a user to an online location, e.g., a website for viewing, hearing, and/or downloading instructions. In some embodiments, instructions or other information are provided as an application ("app") for a mobile device.

DETAILED DESCRIPTION OF THE INVENTION

Provided herein is technology relating to the amplification-based detection of nucleic acids and particularly, but not exclusively, to methods for enriching low-DNA, bisulfite-converted samples for analysis.

Biological samples of interest may have vastly different amounts of DNA in them, and even if rich in bulk DNA, may have very low amounts of DNAs of interest, e.g., non-normal DNAs within a background of normal DNA, or human DNA in a background of microbial DNA (or vice versa). To compensate for a low concentration of target DNA, a large sample may sometimes be processed to collect sufficient DNA for a particular assay. However, when it is desirable to subject a sample with a low concentration of target DNA to a number of different assays in parallel, the necessary sample size may become prohibitively large. For example, circulating free DNA in plasma of a subject is typically very low, as it is continuously cleared from the bloodstream, mainly by the liver, and has a half-life of only 10 to 15 minutes. The typical levels of circulating DNA are thus very low, e.g., for healthy individuals, a particular segment of DNA, e.g., from a gene of interest, may be present at about 1,500-2000 copies/mL, while a segment of DNA associated with a tumor may be present at about 5000 copies/mL in a subject with a late stage cancer. Further, tumor-derived cfDNA in plasma is typically fragmented into short strands, e.g., of 200 or fewer base pairs (see, e.g., P. Jiang, et al., Proc. Natl Acad Sci. 112(11): E1317-E1325 (2015), incorporated herein by reference in its entirety).

Such small DNAs are especially hard to purify because they can be lost during typical purification steps, e.g., through inefficiencies in precipitation and/or DNA binding purification steps.

Recovery of the DNA from such blood fraction samples may capture 75%, but often much less is recovered. Thus, depending on the sensitivity of the particular assay for these targets, analysis of multiple DNA markers from plasma can require large amounts of plasma from a subject. Enrichment by targeted pre-amplification of specific target regions can increase the number of markers that can be analyzed using the same starting sample, i.e., without the need to collect correspondingly larger samples (e.g., plasma or blood) from the subject.

Provided herein are embodiments of technologies for extraction of DNA, e.g., cell-free circulating DNA, from plasma samples. In preferred embodiments, the methods provided herein do not comprise organic extraction (e.g., phenol-chloroform extraction), alcohol precipitation, or use of columns, making the methods readily scalable and automatable. In particularly preferred embodiments, essentially the entire isolation procedure—from plasma sample to bead-bound purified DNA ready for elution—is performed at room temperature.

Provided herein are embodiments of technologies for multiplexed pre-amplification particularly suited for analysis of target DNAs that are in low abundance and/or that are fragmented in the samples in which they are found, and that have been treated with bisulfite reagent, e.g., as described in Leontiou, et al., PLoS ONE 10(8): e0135058. doi:10.1371/journal.pone.0135058 (2015). In certain preferred embodiments, the bisulfite treatment comprises use of ammonium hydrogen sulfite, with desulfonation preferably performed on support-bound DNA, as described in U.S. Pat. No. 9,315,853.

Embodiments of the Technology

1. Isolation of Circulating Cell-Free DNA from Plasma

Provided herein is technology related to isolation of fragmented DNA from samples, e.g., blood or plasma samples. In particular, provided herein is technology related to extraction of low-copy, small DNAs, e.g., less than about 200 base pairs in length, from plasma samples, using mixable particles, e.g., silica particles, to bind DNA. Methods are provided herein using two different lysis reagents, added at different times during the lysis treatment of the plasma sample, and using a combination of two different wash buffers in the processing of DNA bound to the particles. In preferred embodiments, the technology provided herein comprises addition of a bulk exogenous non-target DNA, e.g., bulk fish DNA, to the DNA to be isolated for further analysis, preferably added to the plasma prior to or at the first particle-binding step.

2. Pre-Amplification of Target Regions for PCR-Flap Assay Analysis

Provided herein is technology related to providing an increased amount of DNA for analysis in a PCR-flap assay, e.g., a QuARTS assay as diagramed in FIG. 1. In particular, embodiments of the methods and compositions disclosed herein provide for increasing an amount of a DNA target of interest, e.g., from a low-target sample, using a multiplexed pre-amplification step, followed by target-specific detection to further amplify and to detect the target locus of interest.

Re-amplifying DNA segments previously amplified in a targeted manner, e.g., amplification of an aliquot or dilution of the amplicon product of a target-specific PCR, is known to be prone to undesirable artifacts, e.g., high background of undesired DNA products. Thus, analysis of target nucleic acids using sequential rounds of specific PCR is typically conducted under special conditions, e.g., using different primers pairs in the sequential reactions. For example, in "nested PCR" the first round of amplification is conducted to produce a first amplicon, and the second round of amplification is conducted using a primer pair in which one or both of the primers anneal to sites inside the regions defined by the initial primer pair, i.e., the second primer pair is considered to be "nested" within the first primer pair. In this way, background amplification products from the first PCR that do not contain the correct inner sequence are not further amplified in the second reaction. Other strategies to reduce undesirable effects include using very low concentrations of primers in the first amplification.

Multiplex amplification of a plurality of different specific target sequences is typically conducted using relatively standard PCR reagent mixtures, e.g., for Amplitaq DNA polymerase, mixtures comprising 50 mM KCl, 1.5 to 2.5 mM $MgCl_2$, and Tris-HCl buffer at about pH 8.5 are used. As discussed above, if a second amplification is to be performed, the primers are typically present in limited amounts (Andersson, supra). For a subsequent assay, the amplified DNA is diluted or purified, and a small aliquot is then added to a detection assay, e.g., a PCR-flap assay, which uses different buffer and salt conditions than standard PCR (e.g., a buffer comprising MOPS, Tris-HCl pH 8.0, and 7.5 mM $MgCl_2$, and little or no added KCl or other monovalent salt, conditions typically considered unfavorable for PCR due to the low monovalent salt and the relatively high concentration of $Mg^{++}$ (see, e.g., "Guidelines for PCR Optimization with Taq DNA Polymerase" https://www.neb.com/tools-and-resources/usage-guidelines/guidelines-for-pcr-optimization-with-taq-dna-polymerase, which discloses 1.5 mM to 2.0 mM as the optimal $Mg^{++}$ range for Taq DNA polymerase, with optimization to be conducted by supplementing the magnesium concentration in 0.5 increments up to 4 mM. See also "Multiplex PCR: Critical Parameters and Step-by-Step Protocol" O. Henegariu, et al., BioTechniques 23:504-511 (September 1997). A change in reaction conditions between a first amplification and a second amplification (or other detection assay) is often effected by either purifying the DNA from the first amplification reaction or by using sufficient dilution such that the amounts of reaction components carried into the follow-on reaction is negligible.

Embodiments of the present technology are directed to combining bisulfite modification, multiplex PCR amplification, and PCR-flap assay detection for the detection of low-copy number DNAs. During development of embodiments of the technology provided herein, it was discovered that use of a PCR-flap assay buffer with very low KCl and comprising elevated $Mg^{++}$ (e.g., >6 mM, preferably >7 mM, more preferably 7.5 mM), for both the multiplex pre-amplification in the absence of the flap assay reagents (e.g., in the absence of the hairpin oligonucleotide and FEN-1 endonuclease) and for the following PCR-flap assay produced substantially better signal. Further, it was unexpectedly determined that using the same primer pair to amplify a target region in both the pre-amplification and in the subsequent PCR-flap assay reaction produced better results than using a nested arrangement of primers. Use of the PCR-flap assay primers pairs in the initial amplification and in the PCR-flap assay has the advantage of producing signal from very small fragments of target DNA, such as would be expected in remote DNA samples. For example, amplicons of about 50 to 85 base pairs are produced and detected in examples hereinbelow).

In some embodiments, the one or both of the pre-amplification and the PCR-flap assay comprise exogenous, non-target DNA in the reaction mixture, as described, e.g., in U.S. patent application Ser. No. 14/036,649, filed Sep. 25, 2013, which is incorporated herein by reference in its entirety. In certain preferred embodiments, the exogenous non-target DNA comprises fish DNA. While not limiting the invention to any particular mechanism of action, it has been observed that the presence of hairpin oligonucleotides (e.g., hairpin FRET cassettes as used, for example, in some embodiments of invasive cleavage detection assays) may have an inhibiting effect on DNA polymerase present in the same vessel, as assessed by sample and signal amplification. See, e.g., U.S. Patent Publication 2006/0147955 to Allawi, which is incorporated herein by reference for all purposes. Allawi et al. observed that when PCR and invasive cleavage assay components were combined, the hairpin FRET oligonucleotides affected polymerase performance, and the use of purified exogenous non-target DNA, especially genomic DNA, improves the consistency of signal produced in such assays. Thus, in preferred embodiments, purified exogenous non-target DNA is added to samples before and/or while contacting the samples with an enzyme such as a polymerase. The non-target DNA is typically added to the sample or reaction mixture, for example, at a concentration of approximately 2 to 20 ng per µl of reaction mixture, preferably approximately 6 to approximately 7 ng per µl of reaction mixture, when approximately 0.01 to 1.0 U/µL of enzyme, e.g., 0.05 U/µL of enzyme (e.g., a polymerase such as, e.g., Taq polymerase) is used in the assay.

Embodiments of the multiplex pre-amplification as disclosed herein find use with PCR-flap assays such as the QuARTS assay. As diagrammed in FIG. 1, the QuARTS technology combines a polymerase-based target DNA amplification process with an invasive cleavage-based signal amplification process. Fluorescence signal generated by the QuARTS reaction is monitored in a fashion similar to real-time PCR. During each amplification cycle, three sequential chemical reactions occur in each assay well, with the first and second reactions occurring on target DNA templates and the third occurring on a synthetic DNA target labeled with a fluorophore and quencher dyes, thus forming a fluorescence resonance energy transfer (FRET) donor and acceptor pair. The first reaction produces amplified target with a polymerase and oligonucleotide primers, and the second reaction uses a highly structure-specific 5'-flap endonuclease-1 (FEN-1) enzyme reaction to release a 5'-flap sequence from a target-specific oligonucleotide probe that binds to the product of the polymerase reaction, forming an overlap flap substrate. In the third reaction, the cleaved flap anneals to a specially designed oligonucleotide containing a fluorophore and quencher closely linked in a FRET pair such that the fluorescence is quenched (FRET cassette). The released probe flap hybridizes in a manner that forms an overlap flap substrate that allows the FEN-1 enzyme to cleave the 5'-flap containing the fluorophore, thus releasing it from proximity to the quencher molecule. The released fluorophore generates fluorescence signal to be detected. During the second and third reactions, the FEN-1 endonuclease can cut multiple probes per target, generating multiple cleaved 5'-flaps per target, and each cleaved 5' flap can participate in the cleavage of many FRET cassettes, giving rise to additional fluorescence signal amplification in the overall reaction.

In some configurations, each assay is designed to detect multiple genes, e.g., 3 genes reporting to 3 distinct fluorescent dyes. See, e.g., Zou, et al., (2012) "Quantification of Methylated Markers with a Multiplex Methylation-Specific Technology", Clinical Chemistry 58: 2, incorporated herein by reference for all purposes.

These embodiments are further understood by the illustrative examples provided below.

EXPERIMENTAL EXAMPLES

Example 1

DNA Isolation from Cells and Plasma and Bisulfite Conversion

DNA Isolation

For cell lines, genomic DNA was isolated from cell-conditioned media using the "Maxwell® RSC ccfDNA Plasma Kit (Promega Corp., Madison, Wis.). Following the kit protocol, 1 mL of cell-conditioned media (CCM) is used in place of plasma, and processed according to the kit procedure. The elution volume is 100 µL, of which 70 µL are used for bisulfite conversion.

An exemplary procedure for isolating DNA from a 4 mL sample of plasma would be conducted as follows:

To a 4 mL sample of plasma, 300 µL of proteinase K (20 mg/mL) is added and mixed.

Add 3 µL of 1 µg/µL of Fish DNA to the plasma-proteinase K mixture.

Add 2 mL of plasma lysis buffer to plasma.
  Plasma lysis buffer is:
    4.3M guanidine thiocyanate
    10% IGEPAL CA-630 (Octylphenoxy poly(ethyleneoxy)ethanol, branched) (5.3 g of IGEPAL CA-630 combined with 45 mL of 4.8 M guanidine thiocyanate)

Incubate mixtures at 55° C. for 1 hour with shaking at 500 rpm.

Add 3 mL of plasma lysis buffer and mix.

Add 200 µL magnetic silica binding beads [16 µg of beads/µL] and mix again.

Add 2 mL of 100% isopropanol and mix.

Incubate at 30° C. for 30 minutes with shaking at 500 rpm.

Place tube(s) on magnet and let the beads collect. Aspirate and discard the supernatant.

Add 750 µL guanidine hydrochloride-ethyl alcohol (GuHCl-EtOH) wash solution to vessel containing the binding beads and mix.
  GuHCl-EtOH wash solution is:
    3M GuHCl
    57% EtOH.

Shake at 400 rpm for 1 minute.

Transfer samples to a deep well plate or 2 mL microfuge tubes.

Place tubes on magnet and let the beads collect for 10 minutes. Aspirate and discard the supernatant.

Add 1000 µL wash buffer (10 mM Tris HCl, 80% EtOH) to the beads, and incubate at 30° C. for 3 minutes with shaking.

Place tubes on magnet and let the beads collect. Aspirate and discard the supernatant.

Add 500 µL wash buffer to the beads and incubate at 30° C. for 3 minutes with shaking.

Place tubes on magnet and let the beads collect. Aspirate and discard the supernatant.

Add 250 μL wash buffer and incubate at 30° C. for 3 minutes with shaking.

Place tubes on magnet and let the beads collect. Aspirate and discard the remaining buffer.

Add 250 μL wash buffer and incubate at 30° C. for 3 minutes with shaking.

Place tubes on magnet and let the beads collect. Aspirate and discard the remaining buffer.

Dry the beads at 70° C. for 15 minutes, with shaking.

Add 125 μL elution buffer (10 mM Tris HCl, pH 8.0, 0.1 mM EDTA) to the beads and incubate at 65° C. for 25 minutes with shaking.

Place tubes on magnet and let the beads collect for 10 minutes.

Aspirate and transfer the supernatant containing the DNA to a new vessel or tube.

Bisulfite Conversion

I. Sulfonation of DNA Using Ammonium Hydrogen Sulfite
1. In each tube, combine 64 μL DNA, 7 μL 1 N NaOH, and 9 μL of carrier solution containing 0.2 mg/mL BSA and 0.25 mg/mL of fish DNA.
2. Incubate at 42° C. for 20 minutes.
3. Add 120 μL of 45% ammonium hydrogen sulfite and incubate at 660 for 75 minutes.
4. Incubate at 4° C. for 10 minutes.

II. Desulfonation Using Magnetic Beads

Materials

Magnetic beads (Promega MagneSil Paramagnetic Particles, Promega catalogue number AS1050, 16 μg/μL).

Binding buffer: 6.5-7 M guanidine hydrochoride.

Post-conversion Wash buffer: 80% ethanol with 10 mM Tris HCl (pH 8.0).

Desulfonation buffer: 70% isopropyl alcohol, 0.1 N NaOH was selected for the desulfonation buffer.

Samples are mixed using any appropriate device or technology to mix or incubate samples at the temperatures and mixing speeds essentially as described below. For example, a Thermomixer (Eppendorf) can be used for the mixing or incubation of samples. An exemplary desulfonation is as follows:

1. Mix bead stock thoroughly by vortexing bottle for 1 minute.
2. Aliquot 50 μL of beads into a 2.0 mL tube (e.g., from USA Scientific).
3. Add 750 μL of binding buffer to the beads.
4. Add 150 μL of sulfonated DNA from step I.
5. Mix (e.g., 1000 RPM at 30° C. for 30 minutes).
6. Place tube on the magnet stand and leave in place for 5 minutes. With the tubes on the stand, remove and discard the supernatant.
7. Add 1,000 μL of wash buffer. Mix (e.g., 1000 RPM at 30° C. for 3 minutes).
8. Place tube on the magnet stand and leave in place for 5 minutes. With the tubes on the stand, remove and discard the supernatant.
9. Add 250 μL of wash buffer. Mix (e.g., 1000 RPM at 30° C. for 3 minutes).
10. Place tube on magnetic rack; remove and discard supernatant after 1 minute.
11. Add 200 μL of desulfonation buffer. Mix (e.g., 1000 RPM at 30° C. for 5 minutes).
12. Place tube on magnetic rack; remove and discard supernatant after 1 minute.
13. Add 250 μL of wash buffer. Mix (e.g., 1000 RPM at 30° C. for 3 minutes).
14. Place tube on magnetic rack; remove and discard supernatant after 1 minute.
15. Add 250 μL of wash buffer to the tube. Mix (e.g., 1000 RPM at 30° C. for 3 minutes).
16. Place tube on magnetic rack; remove and discard supernatant after 1 minute.
17. Incubate all tubes at 30° C. with the lid open for 15 minutes.
18. Remove tube from magnetic rack and add 70 μL of elution buffer directly to the beads.
19. Incubate the beads with elution-buffer (e.g., 1000 RPM at 40° C. for 45 minutes).
20. Place tubes on magnetic rack for about one minute; remove and save the supernatant.

The converted DNA is then used in pre-amplification and/or flap endonuclease assays, as described below.

Example 2

Multiplex Pre-Amplification—Cycles of Pre-Amplification

Using a nested approach, the effect of the number of PCR cycles was examined by conducting 5, 7 or 10 cycles using the outer primer pairs for each target sample. The PCR-flap assays using inner primers were used to further amplify and to analyze the pre-amplified products.

Experimental conditions:
1. Sample source: DNA extracted from HCT116 cell lines and bisulfite treated as described above;
2. 50 μL pre-amplification PCR reactions.
3. Targets regions tested: NDRG4, BMP3, SFMBT2, VAV3, ZDHHC1, and β-actin (see FIG. 5)
4. Reaction conditions used for both pre-amplification PCR and the PCR-flap assay:
7.5 mM $MgCl_2$,
10 mM MOPS,
0.3 mM Tris-HCl, pH 8.0,
0.8 mM KCl,
0.1 μg/μl BSA,
0.0001% Tween-20,
0.0001% IGEPAL CA-630,
250 μM dNTP)
GoTaq polymerase at 0.025 U/μl (Promega Corp., Madison, Wis.)
Primer pairs for bisulfite-converted NDRG4, BMP3, SFMBT2, VAV3, ZDHHC1, and β-actin, as shown in FIGS. 5A-5F, at 500 nM each primer in both the pre-amplification and the PCR-flap assay.

10 μL of prepared bisulfite-treated target DNA are used in each 50 μL PCR reaction. Pre-amplification cycling was as shown below:

| Pre-Amplification Reaction Cycles: | | |
| --- | --- | --- |
| Stage | Temp/Time | # of Cycles |
| Pre-incubation | 95° C./5' | 1 |
| Amplification 1 | 95° C./30" | varying |
|  | 68° C./30" |  |
|  | 72° C./30" |  |
| Cooling | 40° C./30" | 1 |

After PCR, 10 μL of the amplification reaction was diluted to 100 μL in 10 mM Tris, 0.1 mM EDTA, and 10 μL of the diluted amplification product are used in a standard PCR-flap assay, as described below. Comparative assays used a QuARTS PCR-flap assay directly on the bisulfite-treated DNA, without pre-amplification.

An exemplary QuARTS reaction typically comprises approximately 400-600 nM (e.g., 500 nM) of each primer and detection probe, approximately 100 nM of the invasive oligonucleotide, approximately 600-700 nM of each FAM (e.g., as supplied commercially by Hologic), HEX (e.g., as supplied commercially by BioSearch Technologies, IDT), and Quasar 670 (e.g., as supplied commercially by Bio-Search Technologies) FRET cassettes, 6.675 ng/µL FEN-1 endonuclease (e.g., Cleavase® 2.0, Hologic, Inc.), 1 unit Taq DNA polymerase in a 30 µl reaction volume (e.g., GoTaq® DNA polymerase, Promega Corp., Madison, Wis.), 10 mM 3-(n-morpholino) propanesulfonic acid (MOPS), 7.5 mM $MgCl_2$, and 250 µM of each dNTP.

Exemplary QuARTS cycling conditions are as shown below:

| Stage | Temp/Time | Number of Cycles | Acquisition |
|---|---|---|---|
| QuARTS Reaction Cycle: | | | |
| Pre-incubation | 95° C./3' | 1 | none |
| Amplification 1 | 95° C./20" | 10 | none |
| | 63° C./30" | | none |
| | 70° C./30" | | none |
| Amplification 2 | 95° C./20" | 35 | none |
| | 53° C./1' | | single |
| | 70° C./30" | | none |
| Cooling | 40° C./30" | 1 | none |

The data are shown in FIG. 6, and show that 10 cycles of pre-amplification gave the most consistent determination of the percentage of methylation, as compared to the PCR-flap assay performed without pre-amplification.

Example 3

Nested Primers Vs. Non-Nested Primers; PCR Buffer Vs. PCR-Flap Assay Buffer

Assays were conducted to compare using a nested primer arrangement to the use of the same PCR flap assay primers in both the pre-amplification and the PCR-flap assay steps, and to compare the use of a typical PCR buffer vs. a PCR-flap assay buffer during the pre-amplification step. The PCR-flap assay buffer was used. The typical PCR buffer was 1.5 mM $MgCl_2$, 20 mM Tris-HCl, pH 8, 50 mM KCl, 250 µM each dNTP; and the PCR-flap assay buffer was 7.5 mM $MgCl_2$, 10 mM MOPS, 0.3 mM Tris-HCl, pH 8.0, 0.8 mM KCl, 0.1 µg/µL BSA, 0.0001% Tween-20, 0.0001% IGEPAL CA-630, 250 µM each dNTP. Primer concentrations of 20 nM, 100 nM and 500 nM each primer were also compared.

Experimental conditions:
1. Sample source: DNA extracted from HCT116 cell lines and bisulfite treated;
2. 50 µL PCR reactions.
3. Targets regions tested: NDRG4, BMP3, SFMBT2, VAV3, ZDHHC1, and β-actin
4. GoTaq polymerase at 0.025 U/µL.
5. PCR or PCR-flap assay buffer, as described above,
6. Primer pairs for bisulfite-converted NDRG4, BMP3, SFMBT2, VAV3, ZDHHC1, and β-actin, as shown in FIGS. 5A-5F, at 20 nM, 100 nM and 500 nM each primer.

Pre-amplification cycling was as shown below:

| Stage | Temp/Time | # of Cycles |
|---|---|---|
| Pre-Amplification Reaction Cycle: | | |
| Pre-incubation | 95° C./5' | 1 |
| Amplification 1 | 95° C./30" | 11 |
| | 68° C./30" | |
| | 72° C./30" | |
| Cooling | 40° C./30" | 1 |

10 µL of prepared bisulfite-treated target DNA were used in each 50 µL PCR reaction. After PCR, 10 µL of the pre-amplification reaction was diluted to 100 µL in 10 mM Tris, 0.1 mM EDTA, and 10 µL of the diluted amplification product are used in a standard PCR-flap assay, as described in Example 2.

The data are shown in FIG. 7. The top panel shows expected yields calculated from starting DNA amounts and the second panel shows amounts detected using the primer and buffer conditions indicated. These data show that the highest nM concentrations of primers gave the highest amplification efficiency. Surprisingly, the PCR-flap assay buffer having relatively high $Mg^{++}$ and low KCl (7.5 mM 0.8 mM, respectively), when used in the PCR pre-amplification, gave better results than use of a traditional PCR buffer having lower $Mg^{++}$ and much higher KCl concentration (1.5 mM and 50 mM, respectively). Further, using the PCR-flap assay primers (the "inner" primers and shown in FIGS. 5A-5F) in the pre-amplification PCR worked as well or better than using sets outer and inner primer pairs in a nested PCR arrangement.

Example 4

Testing Cycles of Pre-Amplification in Flap Assay Buffer

Assays were conducted to determine effect of increasing the number of pre-amplification PCR cycles on background in both no target control samples and on samples containing target DNA.

Experimental Conditions:
1. Sample source:
    i) No target control=20 ng/µL fish DNA and/or 10 mM Tris, 0.1 mM EDTA;
    ii) Bisulfite-converted DNA isolated from plasma from a normal patient
    iii) Bisulfite-converted DNA isolated from plasma from a normal patient combined with DNA extracted from HCT116 cell lines and bisulfite treated
2. 50 µL PCR reactions,
3. Targets regions tested: NDRG4, BMP3, SFMBT2, VAV3, ZDHHC1, and β-actin,
4. Reaction conditions used for both pre-amplification and PCR-flap assay:
    7.5 mM $MgCl_2$,
    10 mM MOPS,
    0.3 mM Tris-HCl, pH 8.0,
    0.8 mM KCl,
    0.1 µg/µL BSA,
    0.0001% Tween-20,
    0.0001% IGEPAL CA-630,
    250 µM dNTP)
    GoTaq polymerase at 0.025 U/µl, Primer pairs for bisulfite-converted NDRG4, BMP3, SFMBT2, VAV3, ZDHHC1, and β-actin, as shown in FIGS. 5A-5F, at 500 nM each primer.
Pre-amplification cycling was as shown below:

| Pre-Amplification Reaction Cycle: | | |
|---|---|---|
| Stage | Temp/Time | # of Cycles |
| Pre-incubation | 95° C./5' | 1 |
| Amplification 1 | 95° C./30" | 5, 10, 20, or 25 |
|  | 68° C./30" |  |
|  | 72° C./30" |  |
| Cooling | 40° C./30" | 1 |

After PCR, 10 μL of the amplification reaction was diluted to 100 μL in 10 mM Tris, 0.1 mM EDTA, and 10 μL of the diluted amplification product are used in a standard PCR-flap assay, as described in Example 1.

The data are shown in FIGS. 8A-8C, and showed that no background was produced in the no-target control reactions, even at the highest cycle number. However, the samples pre-amplified for 20 or 25 cycles showed a noticeable decrease in signal in the PCR-flap assay.

Example 5

Multiplex Targeted Pre-Amplification of Large-Volume Bisulfite-Converted DNA

To pre-amplify most or all of the bisulfite treated DNA from an input sample, a large volume of the treated DNA may be used in a single, large-volume multiplex amplification reaction. For example, DNA is extracted from a cell lines (e.g., DFCI032 cell line (adenocarcinoma); H1755 cell line (neuroendocrine), using, for example, the Maxwell Promega blood kit #AS1400, as described above. The DNA is bisulfite converted, e.g., as described in Example 1.

A pre-amplification is conducted in a reaction mixture containing 7.5 mM MgCl$_2$, 10 mM MOPS, 0.3 mM Tris-HCl, pH 8.0, 0.8 mM KCl, 0.1 μg/μL BSA, 0.0001% Tween-20, 0.0001% IGEPAL CA-630, 250 μM dNTP, (e.g., 12 primer pairs/24 primers, in equimolar amounts, or with individual primer concentrations adjusted to balance amplification efficiencies of the different target regions), 0.025 units/μL HotStart GoTaq concentration, and 20 to 50% by volume of bisulfite-treated target DNA (e.g., 10 μL of target DNA into a 50 μL reaction mixture, or 50 μL of target DNA into a 125 μL reaction mixture). Thermal cycling times and temperatures are selected to be appropriate for the volume of the reaction and the amplification vessel. For example, the reactions may be cycled as follows

| Stage | Temp/Time | # of Cycles |
|---|---|---|
| Pre-incubation | 95° C./5' | 1 |
| Amplification 1 | 95° C./30" | 10 |
|  | 64° C./30" |  |
|  | 72° C./30" |  |
| Cooling | 4° C./Hold | 1 |

After thermal cycling, aliquots of the pre-amplification reaction (e.g., 10 μL) are diluted to 500 μL in 10 mM Tris, 0.1 mM EDTA. Aliquots of the diluted pre-amplified DNA (e.g., 10 μL) are used in a QuARTS PCR-flap assay, e.g., as described in Example 2.

Example 6

Multiplex Targeted Pre-Amplification of Bisulfite-Converted DNA from Stool Samples The multiplex pre-amplification methods described above were tested on DNA isolated from human stool samples.
Sample source:
i) 4 DNA samples captured from stool samples (see, e.g., U.S. Pat. No. 9,000,146) and bisulfite-treated according to Example 1, above, the samples having the following pathologies:

| 500237 | Adenoma (AA) |
| 500621 | Adenocarcinoma (ACA) |
| 780116 | Normal |
| 780687 | Normal | ii) No target control=20 ng/μL bulk fish DNA and/or 10 mM Tris, 0.1 mM EDTA;
2. 50 μL PCR reactions,
3. Targets regions tested: NDRG4, BMP3, SFMBT2, VAV3, ZDHHC1, and β-actin,
4. Reaction conditions used for both pre-amplification and PCR-flap assay:
7.5 mM MgCl$_2$,
10 mM MOPS,
0.3 mM Tris-HCl, pH 8.0,
0.8 mM KCl,
0.1 μg/μL BSA,
0.0001% Tween-20,
0.0001% IGEPAL CA-630,
250 μM dNTP)
GoTaq polymerase at 0.025 U/μl,
Primer pairs for bisulfite-converted NDRG4, BMP3, SFMBT2, VAV3, ZDHHC1, and β-actin, as shown in FIGS. 5A-5F, at 500 nM each primer.
Pre-amplification cycling was as shown below:

| Pre-Amplification Reaction Cycle: | | |
|---|---|---|
| Stage | Temp/Time | # of Cycles |
| Pre-incubation | 95° C./5' | 1 |
| Amplification 1 | 95° C./30" | 10 |
|  | 68° C./30" |  |
|  | 72° C./30" |  |
| Cooling | 40° C./30" | 1 |

After PCR, 10 μL of the amplification reaction was diluted to 100 μL in 10 mM Tris, 0.1 mM EDTA, and 10 μL of the diluted amplification product are used in a standard PCR-flap assay, as described in Example 2.

The data are shown in FIG. 9, and show that no background was produced in the no-target control reactions. For samples in which the target markers are not expected to be methylated (normal samples) no signal for methylated markers was detected, while the percent methylation detected in the samples from subjects having adenoma or adenocarcinoma were consistent with the results obtained using a standard non-multiplexed QuARTS PCR-flap assay, i.e., without a separate pre-amplification step.

Example 6

Multiplex Targeted Pre-Amplification of Bisulfite-Converted DNA from Plasma Samples The multiplex pre-amplification methods described above were tested on DNA isolated from human plasma samples and treated with bisulfite, as described in Example 1.

Experimental conditions:
1. Sample source:
   Extracted and bisulfite-treated 75 plasma samples from patients with colorectal cancer or stomach cancer, or from normal patients—2 mL each.
2. 50 µL PCR reactions,
3. Targets regions tested: NDRG4, BMP3, SFMBT2, VAV3, ZDHHC1, and β-actin,
4. Reaction conditions used for both pre-amplification and PCR-flap assay:
   7.5 mM $MgCl_2$,
   10 mM MOPS,
   0.3 mM Tris-HCl, pH 8.0,
   0.8 mM KCl,
   0.1 µg/µL BSA,
   0.0001% Tween-20,
   0.0001% IGEPAL CA-630,
   250 µM dNTP)
   GoTaq polymerase at 0.025 U/µl,
   Primer pairs for bisulfite-converted NDRG4, BMP3, SFMBT2, VAV3, ZDHHC1, and β-actin, as shown in FIGS. 5A-5F, at 500 nM each primer.

Pre-amplification cycling was as shown below:

| Pre-Amplification Reaction Cycle: | | |
| --- | --- | --- |
| Stage | Temp/Time | # of Cycles |
| Pre-incubation | 95° C./5' | 1 |
| Amplification 1 | 95° C./30" | 10 |
|  | 68° C./30" |  |
|  | 72° C./30" |  |
| Cooling | 40° C./30" | 1 |

After PCR, 10 µL of the amplification reaction was diluted to 100 µL in 10 mM Tris, 0.1 mM EDTA, and 10 µL of the diluted amplification product are used in a standard PCR-flap assay, as described in Example 2.

Figure 10I:
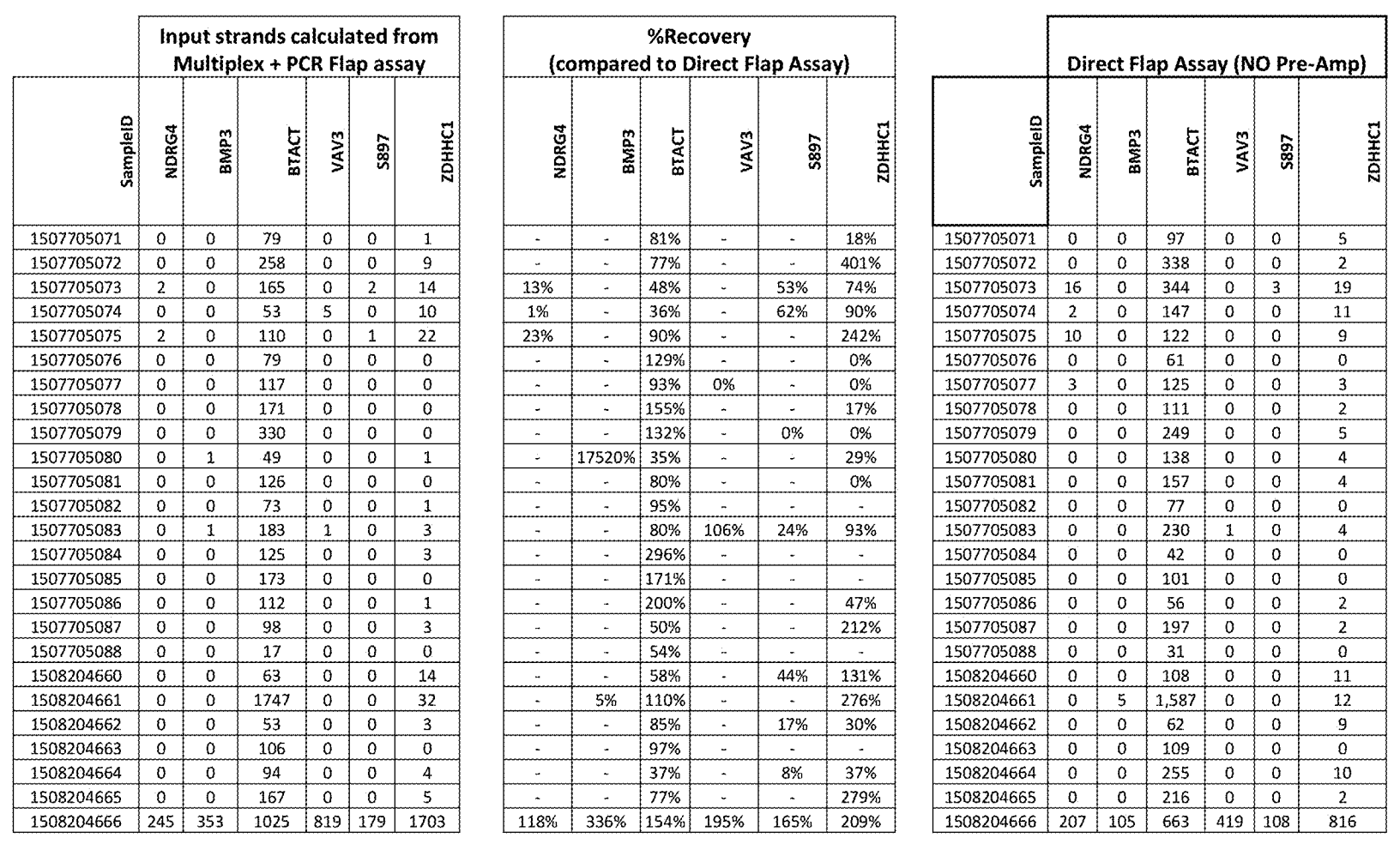

The data are shown in FIGS. 10A-10I. FIGS. 10A-10C compare the results using the multiplex pre-amplification plus the PCR-flap assay to the results from the same samples in which no pre-amplification is performed. FIGS. 10D-10F show the percent methylation calculated for each sample using the multiplex pre-amplification plus the PCR-flap assay, and FIGS. 10G-10I shows the percent recovery of the input strands in the multiplex pre-amplification plus the PCR-flap assay, as compared to the results from the same samples using the PCR-flap assay with no pre-amplification step. Using 3 markers (VAV3, SFMBT2, ZDHHC1) for colorectal cancer, these data showed 92% sensitivity (23/25), at 100% specificity.

Embodiments of the technology disclosed herein offer at least 100-fold or greater sensitivity for detecting DNA from blood, e.g., 2.5 copies from 4 mL of plasma, compared to 250 copies using the QuARTS PCR flap assay without pre-amplification.

Example 7

An Exemplary Protocol for Complete Blood-to-Result Analysis of Plasma DNA

An example of a complete process for isolating DNA from a blood sample for use, e.g., in a detection assay, is provided in this example. Optional bisulfite conversion and detection methods are also described.

I. Blood Processing

Whole blood is collected in anticoagulant EDTA or Streck Cell-Free DNA BCT tubes. An exemplary procedure is as follows:

1. Draw 10 mL whole blood into vacutainers tube (anticoagulant EDTA or Streck BCT), collecting the full volume to ensure correct blood to anticoagulant ratio.
2. After collection, gently mix the blood by inverting the tube 8 to 10 times to mix blood and anticoagulant and keep at room temperature until centrifugation, which should happen within 4 hours of the time of blood collection.
3. Centrifuge blood samples in a horizontal rotor (swing-out head) for 10 minutes at 1500 g (+100 g) at room temperature. Do not use brake to stop centrifuge.
4. Carefully aspirate the supernatant (plasma) at room temperature and pool in a centrifuge tube. Make sure not to disrupt the cell layer or transfer any cells.
5. Carefully transfer 4 mL aliquots of the supernatant into cryovial tubes.
6. Close the caps tightly and place on ice as soon as each aliquot is made. This process should be completed within 1 hour of centrifugation.
7. Ensure that the cryovials are adequately labeled with the relevant information, including details of additives present in the blood.
8. Specimens can be kept frozen at −20° C. for a maximum of 48 hours before transferring to a −80° C. freezer.

II. Preparation of a Synthetic Process Control DNA

Complementary strands of methylated zebrafish DNA are synthesized having the sequences as shown below using standard DNA synthesis methods such as phosphoramidite addition, incorporating 5-methyl C bases at the positions indicated. The synthetic strands are annealed to create a double-stranded DNA fragment for use as a process control.

A. Annealing and Preparation of Concentrated Zebra Fish (ZF-RASS F1 180Mer) Synthetic

| Oligo Name | Oligo Sequence | SEQ ID NO: |
| --- | --- | --- |
| Zebrafish RASSF1 | 5-TCCAC/iMe-dC/GTGGTGCCCACTCTGGACAGGTGGAGCAGAGGGAAGGTGGTG/iMe-dC/GCATGGTGGG/iMe-dC/GAG/iMe-dC/G/iMe-dC/GTG/iMe-dC/ | 71 |

| Oligo Name | Oligo Sequence | SEQ ID NO: |
|---|---|---|
| me synthetic Target Sense Strand | GCCTGGAGGACCC/iMe-dC/GATTGGCTGA/iMe-dC/GTGTAAACCAGGA/iMe-dC/GAGGACATGACTTTCAGCCCTGCAGCCAGACACAGCTGAGCTGGTGTGACCTGTGTGGAGAGTTCATCTGG-3 | |
| Zebrafish RASSF1 me synthetic Target Anti-Sense Strand | 5-CCAGATGAACTCTCCACACAGGTCACACCAGCTCAGCTGTGTCTGGCTGCAGGGCTGAAAGTCATGTCCT/iMe-dC/GTCCTGGTTTACA/iMe-dC/GTCAGCCAAT/iMe-dC/GGGGTCCTCCAGG/iMe-dC/GCA/iMe-dC/G/iMe-dC/GCT/iMe-dc/GCCCACCATG/iMe-dC/GCACCACCTTCCCTCTGCTCCACCTGTCCAGAGTGGGCACCA/iMe-dC/GGTGGA-3 | 72 |

B. Process Control
1. Reconstitute the lyophilized, single stranded oligonucleotides in 10 mM Tris, pH 8.0, 0.1 mM EDTA, at a concentration of 1 µM.
2. Make 10× Annealing Buffer of 500 mM NaCl, 200 mM Tris-HCl pH 8.0, and 20 mM $MgCl_2$.
3. Anneal the synthetic strands In a total volume of 100 µL, combine equimolar amounts of each of the single-stranded oligonucleotides in 1× annealing buffer, e.g., as shown in the table below:

| Component | Stock Conc. | Final Conc. (copies/µl in 1 ml final volume) | Volume added (µL) |
|---|---|---|---|
| Zebrafish RASSF1 me synthetic Target Sense Strand | 1 µM | 1.0E+10 | 16.6 |
| Zebrafish RASSF1 me synthetic Target Anti-Sense Strand | 1 µM | 1.0E+10 | 16.6 |
| Annealing Buffer | 10X | NA | 10.0 |
| Water | NA | NA | 56.8 |
| | | total vol. | 100.0 µL |

4. Heat the annealing mixture to 98° C. for 11-15 minutes.
5. Remove the reaction tube from the heat and spin down briefly to collect condensation to bottom of tube.
6. Incubate the reaction tube at room temp for 10 to 25 minutes.
7. Add 0.9 mL fish DNA diluent (20 ng/mL bulk fish DNA in Te (10 mM Tris-HCl pH8.0, 0.1 mM EDTA)) to adjust to the concentration of zebrafish RASSF1 DNA fragment to $1.0 \times 10^{10}$ copies/µl of annealed, double-stranded synthetic zebrafish RASSF1 DNA in a carrier of genomic fish DNA.
8. Dilute the process control to a desired concentration with 10 mM Tris, pH 8.0, 0.1 mM EDTA, e.g., as described in the table below, and store at either −20° C. or −80° C.

| Initial Concentration | Target Addition | Te | Total Volume | Final Concentration |
|---|---|---|---|---|
| 1.00E+10 copies/µL | 10 µL | 990 µL | 1000 µL | 1.00E+08 copies/µL |
| 1.00E+08 copies/µL | 10 µL | 990 µL | 1000 µL | 1.00E+06 copies/µL |

C. Preparation of 100× Stock Process Control (12,000 Copies/µL Zebra Fish RASSF1 DNA in 200 ng/µL bulk Fish DNA)
1. Thaw reagents
2. Vortex and spin down thawed reagents
3. Add the following reagents into a 50 mL conical tube

| Reagent | Initial Concentration | Final Concentration | Volume to add (mL) |
|---|---|---|---|
| Stock carrier fish DNA | 10 µg/µL | 200 ng/µL | 0.40 |
| Zebra fish (ZF-RASSF1 180 mer) | 1.00E+06 copies/µL | 1.20E+04 copies/µL | 0.24 |
| 10 mM Tris, pH 8.0, 0.1 mM EDTA | NA | NA | 19.36 |
| | | Total Volume | 20.00 |

4. Aliquot into labeled 0.5 mL tubes and store @ −20° C.

C. Preparation of Ix Stock of Process Control (120 Copies/µL Zebra Fish RASSF1 DNA in 2 ng/µL Fish DNA)
1. Thaw reagents
2. Vortex and spin down thawed reagents
3. Add the following reagents into a 50 mL conical tube:

| Reagent | 1 mL | 5 mL | 10 mL |
|---|---|---|---|
| 100× Zebra Fish Process Control | 10 µL | 50 µL | 100 µL |
| 10 mM Tris, pH 8.0, 0.1 mM EDTA | 990 µL | 4950 µL | 9900 µL |

4. Aliquot 0.3 mL into labeled 0.5 mL tubes and store @ −20° C.

III. DNA Extraction from Plasma
1. Thaw plasma, prepare reagents, label tubes, and clean and setup biosafety cabinet for extraction
2. Add 300 µL Proteinase K (20 mg/mL) to one 50 mL conical tube for each sample.
3. Add 2-4 mL of plasma sample to each 50 mL conical tube (do not vortex).
4. Swirl or pipet to mix and let sit at room temp for 5 min.
5. Add 4-6 mL of lysis buffer 1 (LB1) solution to bring the volume up to approximately 8 mL.
   Lb1 formulation:
      0.1 mL of 120 copies/µL of zebrafish RASSF1 DNA process control, as described above;
      0.9-2.9 mL of 10 mM Tris, pH 8.0, 0.1 mM EDTA (e.g., use 2.9 mL for 2 mL plasma samples)

3 mL of 4.3 M guanidine thiocyanate with 10% IGEPAL (from a stock of 5.3 g of IGEPAL CA-630 combined with 45 mL of 4.8 M guanidine thiocyanate)
6. Invert tubes 3 times.
7. Place tubes on bench top shaker (room temperature) at 500 rpm for 30 minutes at room temperature.
8. Add 200 µL of silica binding beads [16 µg of particles/µL] and mix by swirling.
9. Add 7 mL of lysis buffer 2 (LB2) solution and mix by swirling.
LB2 formulation:
4 mL 4.3 M guanidine thiocyanate mixed with 10% IGEPAL
3 mL 100% Isopropanol
(Lysis buffer 2 may be added before, after, or concurrently with the silica binding beads)
10. Invert tubes 3 times.
11. Place tubes on bench top shaker at 500 rpm for 30 minutes at room temperature.
12. Place tubes on capture aspirator and run program with magnetic collection of the beads for 10 minutes, then aspiration. This will collect the beads for 10 minutes then remove all liquid from the tubes.
13. Add 0.9 mL of Wash Solution 1 (3 M guanidine hydrochloride or guanidine thiocyanate, 56.8% EtOH) to resuspend binding beads and mix by swirling.
14. Place tubes on bench top shaker at 400 rpm for 2 minute at room temperature. (All subsequent steps can be done on the STARlet automated platform.)
15. Mix by repeated pipetting then transfer containing beads to 96 deep well plate.
16. Place plate on magnetic rack for 10 min.
17. Aspirate supernatant to waste.
18. Add 1 mL of Wash Solution 2 (80% Ethanol, 10 mM Tris pH 8.0).
19. Mix for 3 minutes.
20. Place tubes on magnetic rack for 10 min.
21. Aspirate supernatant to waste.
22. Add 0.5 mL of Wash Solution 2.
23. Mix for 3 minutes.
24. Place tubes on magnetic rack for 5 min.
25. Aspirate supernatant to waste.
26. Add 0.25 mL of Wash Solution 2.
27. Mix for 3 minutes.
28. Place tubes on magnetic rack for 5 min.
29. Aspirate supernatant to waste.
30. Add 0.25 mL of Wash Solution 2.
31. Mix for 3 minutes.
32. Place tubes on magnetic rack for 5 min.
33. Aspirate supernatant to waste.
34. Place plate on heat block at 70° C., 15 minutes, with shaking.
35. Add 125 µL of elution buffer (10 mM Tris-HCl, pH 8.0, 0.1 mM EDTA).
36. Incubate 65° C. for 25 minutes with shaking.
37. Place plate on magnet and let the beads collect and cool for 8 minutes.
38. Transfer eluate to 96-well plate and store at −80° C. The recoverable/transferable volume is about 100 µL.

IV. Pre-Bisulfite DNA Quantification

To measure DNA in samples using ACTB gene and to assess zebrafish process control recovery, the DNA may be measured prior to further treatment. Setup a QuARTS PCR-flap assay using 10 µL of the extracted DNA using the following protocol:
1. Prepare 10× Oligo Mix containing forward and reverse primers each at 2 µM, the probe and FRET cassettes at 5 µM and dNTP's at 250 µM each. (See below for primer, probe and FRET sequences)

| Oligo | Sequence (5'-3') | Concentration (µM) | SEQ ID NO: |
|---|---|---|---|
| ZF RASSF1 UT forward primer | CGCATGGTGGGCGAG | 2 | 64 |
| ZF RASSF1 UT reverse primer | ACACGTCAGCCAATCGGG | 2 | 65 |
| ZF RASSF1 UT Probe (Arm 3) | CCACGGACG GCGCGTGCGTTT/3C6/ | 5 | 70 |
| Arm 5 FAM FRET | /FAM/TCT/BHQ-1/AGCCGGTTTTCCGGCTGAGACGTCCGTGG/3C6/ | 5 | 81 |
| ACTB forward primer 3 | CCATGAGGCTGGTGTAAAG | 2 | 75 |
| ACTB Reverse primer 3 | CTACTGTGCACCTACTTAATACAC | 2 | 102 |
| ACTB probe with Arm 1 | CGCCGAGGGCGGCCTTGGAG/3C6/ | 5 | 103 |
| Arm 1 QUASAR670 FRET | /Q670/TCT/BHQ-2/AGCCGG1TTTCCGGCTGAGACCTCGGCG/3C6/ | 5 | 80 |
| dNTP mix | | 250 | |

2. Prepare a master mix as follows:

| Component | Volume per reaction (µL) |
|---|---|
| Water | 15.50 |
| 10X oligo Mix | 3.00 |
| 20X QuARTS Enzyme Mix* | 1.50 |
| total volume | 20.0 |

*20X enzyme mix contains 1 unit/µL GoTaq Hot start polymerase (Promega), 292 ng/µL Cleavase 2.0 flap endonuclease(Hologic).

3. Pipette 10 µL of each sample into a well of a 96 well plate.
4. Add 20 µL of master mix to each well of the plate.
5. Seal plate and centrifuge for 1 minutes at 3000 rpm.
6. Run plates with following reaction conditions on an ABI7500 or Light Cycler 480 real time thermal cycler

| QuARTS Assay Reaction Cycle: | | | | Signal |
|---|---|---|---|---|
| Stage | Temp/Time | Ramp Rate (° C. per second) | Number of Cycles | Acquisition |
| Pre-incubation | 95° C./3 min | 4.4 | 1 | No |
| Amplification 1 | 95° C./2 sec | 4.4 | 5 | No |
|  | 63° C./30 sec | 2.2 |  | No |
|  | 70° C./30 sec | 4.4 |  | No |
| Amplification 2 | 95° C./20 sec | 4.4 | 40 | No |
|  | 53° C./1 min | 2.2 |  | Yes |
|  | 70° C./30 sec | 4.4 |  | No |
| Cooling | 40° C./30 sec | 2.2 | 1 | No |

V. Bisulfite Conversion and Purification of DNA
1. Thaw all extracted DNA samples from the DNA extraction from plasma step and spin down DNA.
2. Reagent Preparation:

| Component Abbreviation | Name | Formulation |
|---|---|---|
| BIS SLN | Bisulfite Conversion Solution | 56.6% Ammonium Bisulfite |
| DES SLN | Desulfonation Solution | 70% Isopropyl alcohol, 0.1N NaOH |
| BND BDS | Binding Beads | Maxwell RNA Beads (16 mg/mL), (Promega Corp.) |
| BND SLN | Binding Solution | 7M Guanidine HCl |
| CNV WSH | Conversion Wash | 10 mM Tris-HCl, 80% Ethanol |
| ELU BUF | Elution Buffer | 10 mM Tris, 0.1 mM EDTA, pH 8.0 |

3. Add 5 µL of 100 ng/µL BSA DNA Carrier Solution to each well in a deep well plate (DWP).
4. Add 80 µL of each sample into the DWP.
5. Add 5 µL of freshly prepared 1.6N NaOH to each well in the DWP(s).
6. Carefully mix by pipetting with pipette set to 30-40 µL to avoid bubbles.
7. Incubate at 42° C. for 20 minutes.
8. Add 120 µL of BIS SLN to each well.
9. Incubate at 66° C. for 75 minutes while mixing during the first 3 minutes.
10. Add 750 µL of BND SLN
11. Pre-mix of silica beads (BND BDS) and add of 50 µL of Silica beads (BND BDS) to the wells of DWP.
12. Mix at 30° C. on heater shaker at 1,200 rpm for 30 minutes.
13. Collect the beads on a plate magnet for 5 minutes followed by aspiration of solutions to waste.
14. Add 1 mL of wash buffer (CNV WSH) then move the plate to a heater shaker and mix at 1,200 rpm for 3 minutes.
15. Collect the beads on a plate magnet for 5 minutes followed by aspiration of solutions to waste.
16. Add 0.25 mL of wash buffer (CNV WSH) then move the plate to the heater shaker and mix at 1,200 rpm for 3 minutes.
17. Collect the beads on a plate magnet followed by aspiration of solutions to waste.
18. Add of 0.2 mL of desulfonation buffer (DES SLN) and mix at 1,200 rpm for 7 minutes at 30° C.
19. Collect the beads for 2 minutes on the magnet followed by aspiration of solutions to waste.
20. Add of 0.25 mL of wash buffer (CNV WSH) then move the plate to the heater shaker and mix at 1,200 rpm for 3 minutes.
21. Collect the beads for 2 minutes on the magnet followed by aspiration of solutions to waste.
22. Add of 0.25 mL of wash buffer (CNV WSH) then move the plate to the heater shaker and mix at 1,200 rpm for 3 minutes.
23. Collect the beads for 2 minutes on the magnet followed by aspiration of solutions to waste.
24. Allow the plate to dry by moving to heater shaker and incubating at 70° C. for 15 minutes while mixing at 1,200 rpm.
25. Add 80 µL of elution buffer (ELU BFR) across all samples in DWP.
26. Incubated at 65° C. for 25 minutes while mixing at 1,200 rpm.
27. Manually Transfer eluate to 96 well plate and store at −80° C.
28. The recoverable/transferable volume is about 65 µL.

VI. QuARTS-X for Methylated DNA Detection and Quantification
  A. Multiplex PCR (mPCR) Setup:
  1. Prepare a 10× primer mix containing forward and reverse primers for each methylated marker of interest to a final concentration of 750 nM each. Use 10 mM Tris-HCl, pH 8, 0.1 mM EDTA as diluent, as described in the examples above.
  2. Prepare 10× multiplex PCR buffer containing 100 mM MOPS, pH 7.5, 75 mM $MgCl_2$, 0.08% Tween 20, 0.08% IGEPAL CA-630, 2.5 mM dNTPs.
  3. Prepare multiplex PCR master mix as follows:

| Component | Volume per reaction (µL) |
|---|---|
| Water | 9.62 |
| 10X Primer Mix (0.75 µM each) | 7.5 |
| mPCR Buffer | 7.5 |
| Hot Start GoTaq (5 units/µl) | 0.38 |
| total volume | 25.0 |

4. Thaw DNA and spin plate down.
  5. Add 25 µL of master mix to a 96 well plate.
  6. Transfer 50 µL of each sample to each well.
  7. Seal plate with aluminum foil seal (do not use strip caps)
  8. Place in heated-lid thermal cycler and proceed to cycle using the following profile, for about 5 to 20 cycles, preferably about 10 to 13 cycles:

| Stage | Temp/Time | Number of Cycles |
|---|---|---|
| Pre-incubation | 95° C./5 min | 1 |
| Amplification 1 | 95° C./30 sec | 12 |
|  | 64° C./60 sec |  |
| Cooling | 4° C./hold | 1 |

9. After completion of the thermal cycling, perform a 1:10 dilution of amplicon as follows:
   a. Transfer 180 μL of 10 mM Tris-HCl, pH 8, 0.1 mM EDTA to each well of a deep well plate.
   b. Add 20 μL of amplified sample to each pre-filled well.
   c. Mix the diluted samples by repeated pipetting using fresh tips and a 200 μL pipettor (be careful not to generate aerosols).
   d. Seal the diluted plate with a plastic seal.
   e. Centrifuge the diluted plate at 1000 rpm for 1 min.
   f. Seal any remaining multiplex PCR product that has not been diluted with a new aluminum foil seal. Place at −80° C.

B. QuARTS Assay on Multiplex-Amplified DNA:

1. Thaw fish DNA diluent (20 ng/μL) and use to dilute plasmid calibrators (see, e.g., U.S. patent application Ser. No. 15/033,803, which is incorporated herein by reference) needed in the assay. Use the following table as a dilution guide:

| Initial Plasmid Concentration, copies per μL | Final plasmid Concentration, copies per μL | μL of plasmid to add | μL of diluent to add | total volume, μL |
|---|---|---|---|---|
| 1.00E+05 | 1.00E+04 | 5 | 45 | 50 |
| 1.00E+04 | 1.00E+03 | 5 | 45 | 50 |
| 1.00E+03 | 1.00E+02 | 5 | 45 | 50 |
| 1.00E+02 | 1.00E+01 | 5 | 45 | 50 |

2. Prepare 10× triplex QuARTS oligo mix using the following table for markers A, B, and C (e.g., markers of interest, plus run control and internal controls such as β-actin or B3GALT6 (see, e.g., U.S. patent application Ser. No. 62/364,082, incorporated herein by reference).

| Oligo | Sequence (5'-3') | Concentration (μM) | SEQ ID NO: |
|---|---|---|---|
| Marker A Forward primer | NA | 2 |  |
| Marker A Reverse primer | NA | 2 |  |
| Marker A probe-Arm 1 | NA | 5 |  |
| Marker B Forward primer | NA | 2 |  |
| Marker B Reverse primer | NA | 2 |  |
| Marker B probe-Arm 5 | NA | 5 |  |
| Marker C Forward primer | NA | 2 |  |
| Marker C Reverse primer | NA | 2 |  |
| Marker C probe-Arm 3 | NA | 5 |  |
| A1 HEX FRET | /HEX/ TCT/BHQ-1/AGCCGGTTTTCCGGCTGAGACCTCGGCG/3C6/ | 5 | 79 |
| A5 FAM FRET | /FAM/ TCT/BHQ-1/AGCCGGTTTTCCGGCTGAGACGTCCGTGG/3C6/ | 5 | 81 |
| A3 QUASAR-670 FRET | /Q670/TCT/BHQ-2/AGCCGGTTTTCCGGCTGAGACTCCGCGTC/3C6/ | 5 | 82 |
| dNTP mix |  | 250 |  |

For example, the following might be used to detect bisulfite-treated β-actin, B3GALT6, and zebrafish RASSF1 markers:

| Oligo | Sequence (5'-3') | Concentration (µM) | SEQ ID NO: |
|---|---|---|---|
| ZF RASSF1 BT Forward primer | TGCGTATGGTGGGCGAG | 2 | 67 |
| ZF RASSF1 BT Reverse primer | CCTAATTTACACGTCAACCAATCGAA | 2 | 68 |
| ZF RASSF1 BT probe-Arm 5 | CCACGGACGGCGCGTGCGTTT/3C6/ | 5 | 70 |
| B3GALT6 Forward primer | GGTTTATTTTGGTTTTTTGAGTTTTCGG | 2 | 73 |
| B3GALT6 Reverse primer | TCCAACCTACTATATTTACGCGAA | 2 | 74 |
| B3GALT6 probe-Arm 1 | CGCCGAGGGCGGATTTAGGG/3C6/ | 5 | 76 |
| BTACT Forward primer | GTGTTTGTTTTTTGATTAGGTGTTTAAGA | 2 | 77 |
| BTACT Reverse primer | CTTTACACCAACCTCATAACCTTATC | 2 | 78 |
| BTACT probe-Arm 3 | GACGCGGAGATAGTGTTGTGG/3C6/ | 5 | 79 |
| Arm 1 HEX FRET | /HEX/TCT/BHQ-1/AGCCGGTTTTCCGGCTGAGACCTCGGCG/3C6/ | 5 | 80 |
| Arm 5 FAM FRET | /FAM/TCT/BHQ-1/AGCCGGTTTTCCGGCTGAGACGTCCGTGG/3C6/ | 5 | 81 |
| Arm 3 QUASAR-670 FRET | /Q670/TCT/BHQ-2/AGCCGGTTTTCCGGCTGAGACTCCGCGTC/3C6/ | 5 | 82 |
| dNTP mix | | 2500 | |

3. Prepare a QuARTS flap assay master mix using the following table:

| Component | Volume per reaction (µL) |
|---|---|
| Water | 15.5 |
| 10X Triplex Oligo Mix | 3.0 |
| 20X QuARTS Enzyme mix | 1.5 |
| total volume | 20.0 |

*20X enzyme mix contains 1 unit/µL GoTaq Hot start polymerase (Promega), 292 ng/µL Cleavase 2.0 flap endonuclease(Hologic).

4. Using a 96 well ABI plates, pipette 20 µL of QuARTS master mix into each well.
5. Add 10 µL of appropriate calibrators or diluted mPCR samples.
6. Seal plate with ABI clear plastic seals.
7. Centrifuge the plate using 3000 rpm for 1 minute.
8. Place plate in ABI thermal cycler programmed to run the following thermal protocol then start the instrument

| | QuARTS Reaction Cycle: | | | Signal |
|---|---|---|---|---|
| Stage | Temp/Time | Ramp Rate (° C. per second) | Number of Cycles | Acquisition |
| Pre-incubation | 95° C./3 min | 4.4 | 1 | none |
| Amplification 1 | 95° C./2 sec | 4.4 | 5 | none |
| | 63° C./30 sec | 2.2 | | none |
| | 70° C./30 sec | 4.4 | | none |
| Amplification 2 | 95° C./20 sec | 4.4 | 40 | none |
| | 53° C./1 min | 2.2 | | Yes |
| | 70° C./30 sec | 4.4 | | none |
| Cooling | 40° C./30 sec | 2.2 | 1 | none |

Example 8

Comparison of Chaotropic Salts in First Wash Solution

Figure 11A:
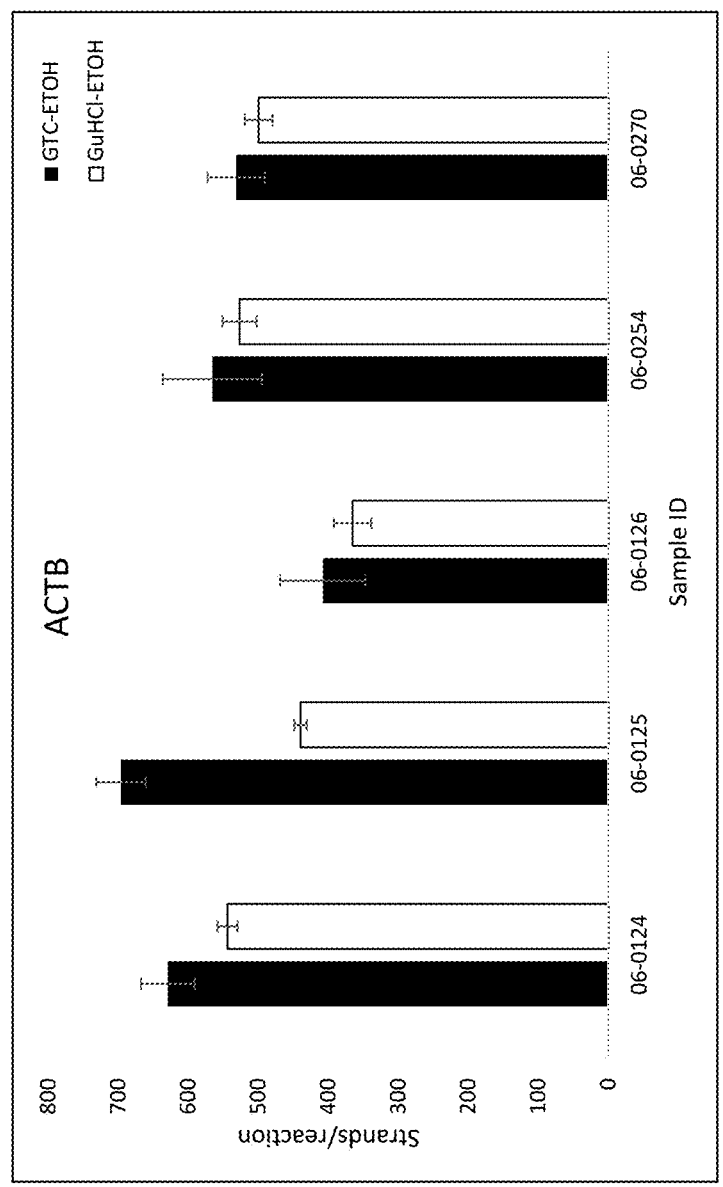
Figure 11B:
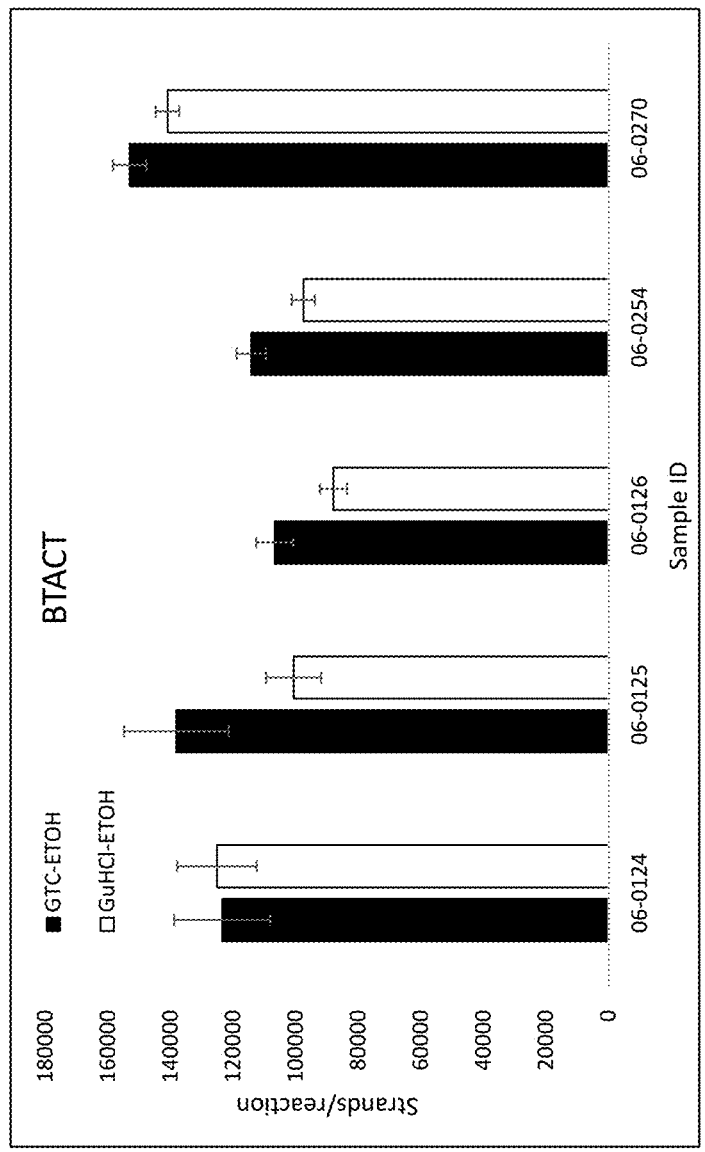

During development of the technology, the effects of using different chaotropic salts, e.g., guanidine thiocyanate vs. guanidine hydrochloride in the first wash solution were compared. DNA was extracted from plasma samples as described in Example 7, with either guanidine thiocyanate-ethyl alcohol or guanidine hydrochloride-ethyl alcohol used as a first wash solution (i.e., 57% ethyl alcohol with either 3 M guanidine hydrochloride or 3 M guanidine thiocyanate). The samples were otherwise processed as described in Example 7 and a portion of the DNA was bisulfite-converted. The amount of resulting unconverted DNA was measured by detection of the process control and β-actin (ACTB) using a QuARTS PCR flap assay, as described above, and the bisulfite-converted DNA was measured by detection of the process control, B3GALT6, and β-actin (BTACT) using a multiplex pre-amplification and QuARTS PCR-flap assay, as described above. The results are shown in FIGS. 11A-11C (process control data not shown). These data show that both solutions produced acceptable DNA yields, with the guanidine thiocyanate-ethanol producing higher yields.

Example 9

Comparison of Ethyl Alcohol with Guanidine Thiocyanate or Guanidine Hydrochloride to Ethyl Alcohol with Buffer in a First Wash Step During development of the technology, the effects of using a mixture of ethyl alcohol (ethanol) with a chaotropic salt solution, e.g., guanidine thiocyanate (GTC) or guanidine hydrochloride (GuHCl) in the first wash step of the plasma DNA extraction described in Example 7, part III i.e., using 57% ethyl alcohol with 3 M guanidine hydrochloride (wash solution 1 in Example 7, part III) or 50% ethyl alcohol with 2.4 M guanidine thiocyanate, was compared to using 80% ethyl alcohol with 10 mM Tris HCl, pH 8.0 (wash solution 2 in Example 7, part III) in the first wash step. The 80% ethanol-Tris buffer solution was used in the subsequent wash steps, as described in Example 7.

Eight replicates were performed for each set of wash conditions. The samples were otherwise processed as described in Example 7 and the DNA was not treated with bisulfite. The amount of resulting DNA was measured by detection of β-actin (ACTB) using a QuARTS PCR flap assay, as described above. The results (mean of DNA strands detected) are shown in the table below. These data show that use of ethyl alcohol with either guanidine thiocyanate or guanidine hydrochloride in the first wash step, followed by additional washes with the ethanol-buffer wash, produced higher yields than the use of the ethanol-buffer wash for all wash steps.

| Wash Condition | Mean | SD | CV |
|---|---|---|---|
| Ethanol-Tris buffer | 1099 | 50.80 | 4.62 |
| Ethanol-GuHCl | 1434 | 76.49 | 5.33 |
| Ethanol-GTC | 1416 | 189.45 | 13.38 |

Example 10

Test of Addition of Lysis Reagent in One Step or Two Step

During development of the technology, the effects of adding the lysis reagent at one or two steps in the isolation procedure were compared. Using aliquots of 2 mL or 4 mL from 6 different plasma samples, the first procedure comprised adding 7 mL of a lysis reagent of 4.3 M guanidine thiocyanate with 10% IGEPAL with proteinase K and a process control as described in Example 1, incubation of the plasma/protease/process control mixture at 55° C. for 60 min, followed by addition of isopropanol. The second procedure comprised adding one aliquot of 3 mL of 4.3 M guanidine thiocyanate with 10% IGEPAL with the protease and process control, and a further aliquot of 4 mL added after the 55° C. incubation, along with the addition of isopropanol. The samples were then further incubated at 30° C. for 30 min., then processed as described in Example 1. A portion of the resulting DNA was bisulfite-converted as described.

Figure 12A:
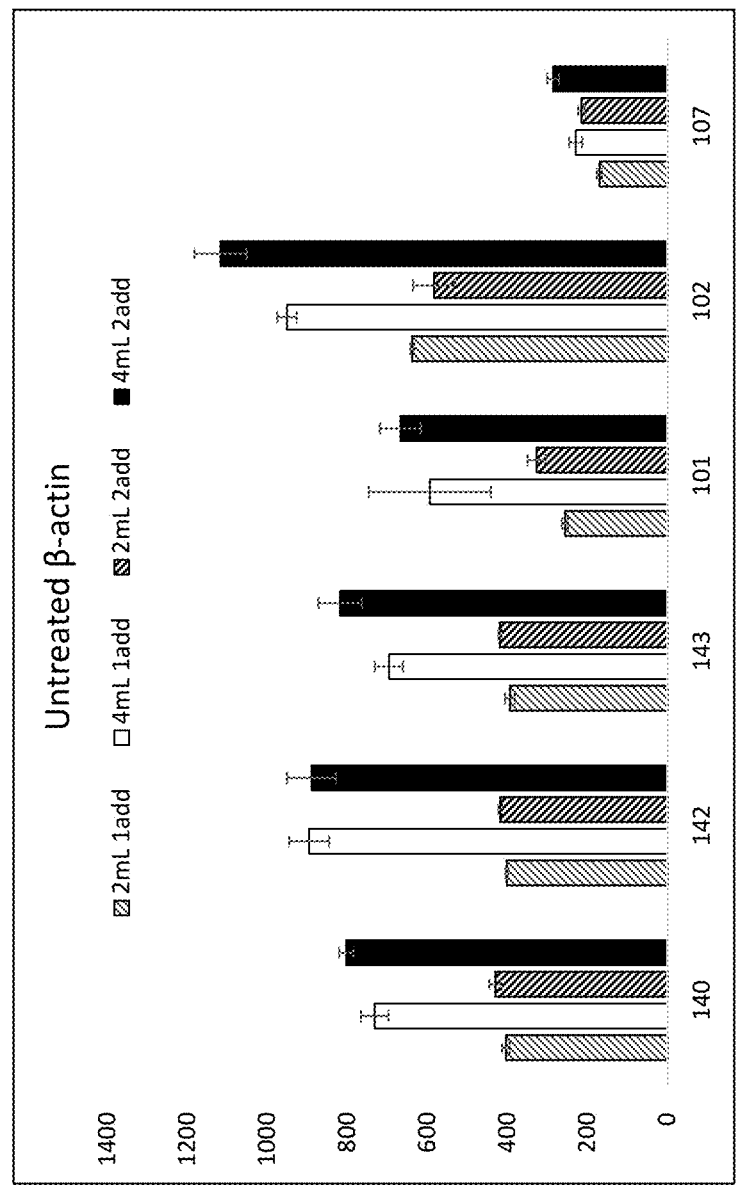
FIGS. 12A-12C show graphs comparing different plasma isolation conditions on the yield of β-actin DNA (untreated and bisulfite converted after extraction) and the B3GALT6 gene (bisulfite converted after extraction, as described in Example 10.
Figure 12B:
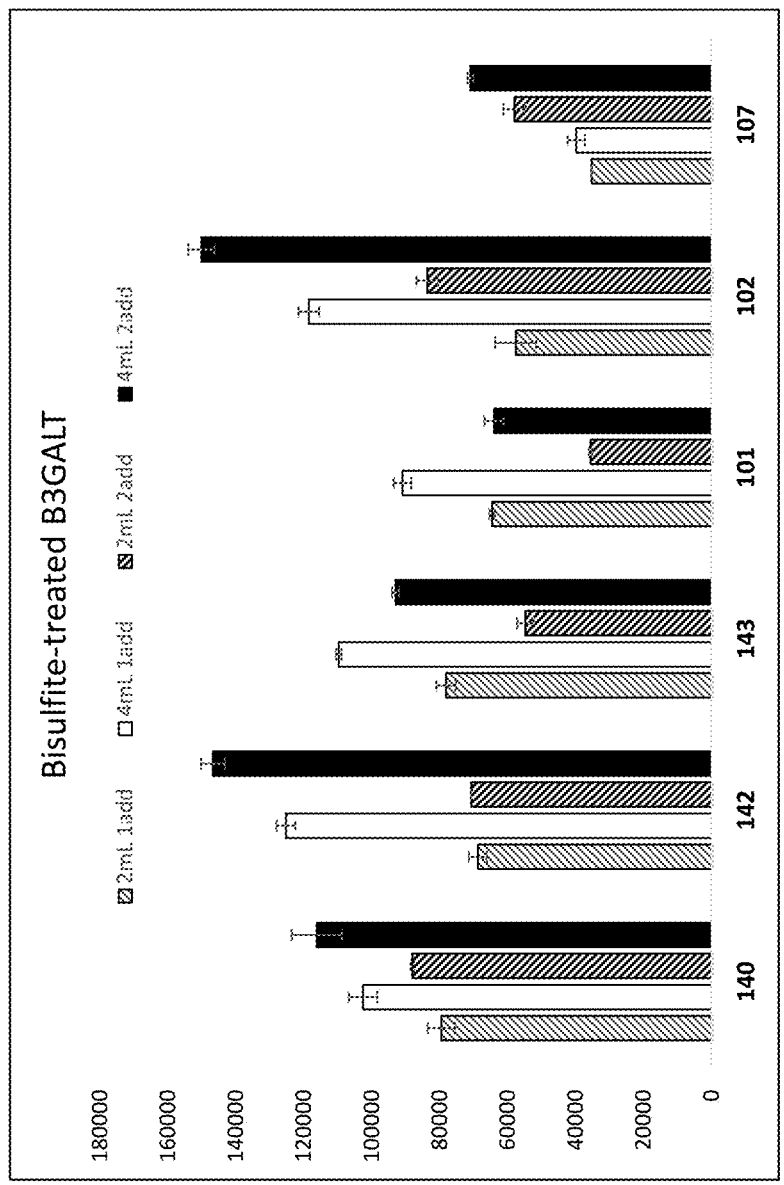
Figure 12C:
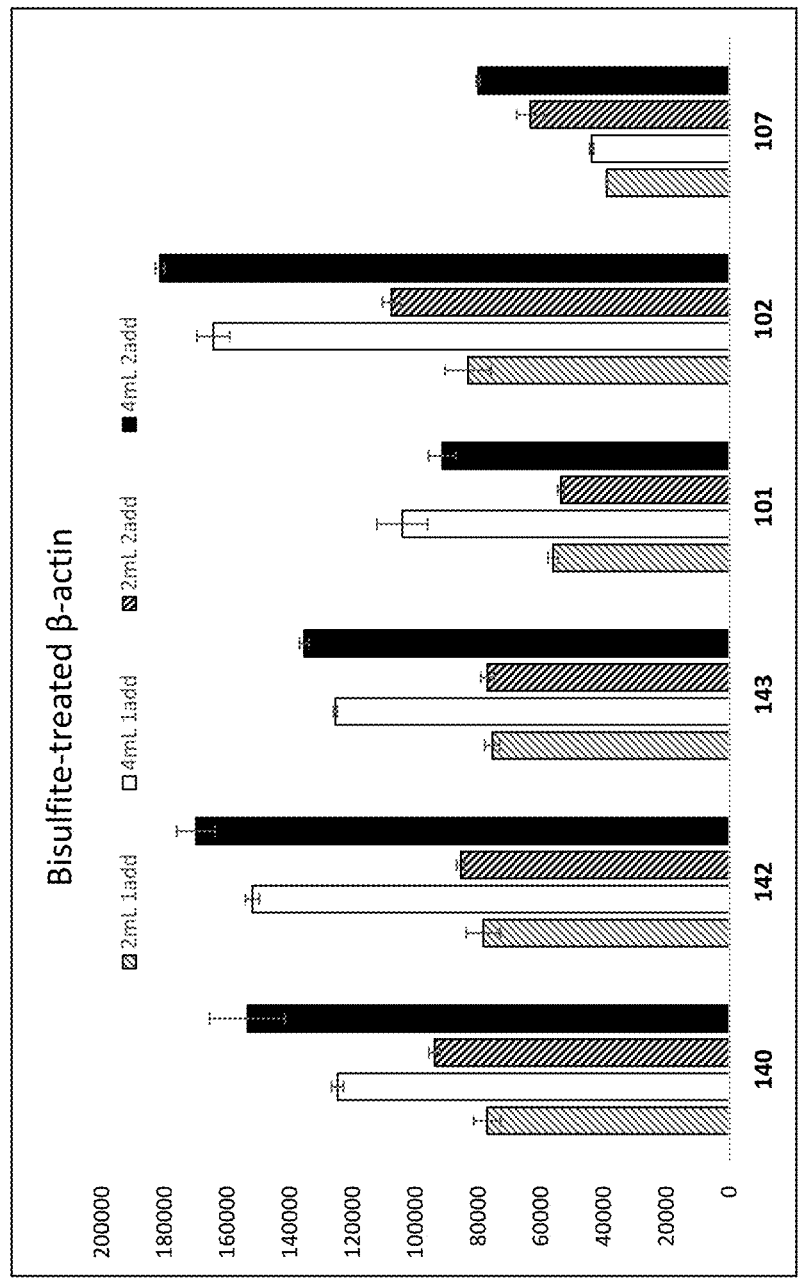

The amount of resulting unconverted DNA was measured by detection of the process control and β-actin (ACTB) using a QuARTS assay, as described above, and the bisulfite-converted DNA was measured by detection of the process control, B3GALT6, and β-actin (BTACT) using a multiplex pre-amplification and QuARTS PCR-flap assay, as described above. The results are shown in FIGS. 12A-12C (process control data not shown). The average fold difference in yield for each tested marker and for the process control (PC) is shown below:

| Average fold difference of 2 additions vs. 1 addition ||||| 
|---|---|---|---|---|
| Unconverted || Bisulfite-converted |||
| PC | ACTB | PC | B3GALT | BTACT |
| 1.07 | 1.12 | 1.04 | 1.12 | 1.20 |

These data show that addition of the lysis reagent in two steps, with the first in the absence of isopropanol and the second added in combination with isopropanol, produces higher yields of detectable DNA.

All publications and patents mentioned in the above specification are herein incorporated by reference in their entireties for all purposes. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A method of analyzing a sample for multiple target nucleic acids in a PCR-flap assay, comprising:
    a) providing a sample comprising DNA suspected of containing one or more of a plurality of different target regions;
    b) treating the sample in an amplification reaction mixture comprising a PCR-flap assay buffer comprising 6 to 10 mM Mg' under conditions wherein the different target regions, if present in the sample, are amplified to form a pre-amplified mixture;
    c) partitioning the pre-amplified mixture into a plurality of different PCR-flap assay reaction mixtures comprising the PCR-flap assay buffer; and
    d) conducting a plurality of PCR-flap assays with the PCR-flap assay reaction mixtures, wherein the different target regions, if present in the sample at step a), are amplified and detected in the PCR-flap assay reaction mixtures.

2. The method of claim 1, wherein the DNA is from a human subject.

3. The method of claim 1, wherein the sample is prepared from a body fluid.

4. The method of claim 1, wherein the body fluid comprises plasma.

5. The method of claim 1, wherein the DNA comprises bisulfite-treated DNA.

6. The method of claim 1, wherein the sample is prepared from cell-free DNA isolated from plasma.

7. The method of claim 1, wherein the amplification reaction comprises at least 3 different primer pairs for amplifying at least 3 different target regions, if present in the sample.

8. The method of claim 1, wherein the amplification reaction comprises at least 4 different primer pairs for amplifying at least 4 different target regions, if present in the sample.

9. The method of claim 1, wherein the pre-amplified mixture is diluted with a diluent prior to partitioning.

10. The method of claim 1, wherein the amplification reaction mixture and/or the plurality of different PCR-flap assay reaction mixtures comprise bulk fish DNA.

11. The method of claim 1, wherein the PCR-flap assay reaction mixtures comprise a FEN-1 endonuclease.

12. The method of claim 1, wherein the PCR-flap assay buffer comprises $MgCl_2$.

13. The method of claim 1, wherein the amplification reaction mixture comprises at least 2 different primer pairs for amplifying the at least 2 different target regions, and wherein each PCR-flap assay reaction mixture comprises an additional amount of a primer pair selected from the at least 2 different primer pairs.

14. The method of claim 13, wherein each PCR-flap assay reaction mixture further comprises:
    i) a flap oligonucleotide, and
    ii) a hairpin oligonucleotide comprising a region that is complimentary to a portion of the flap oligonucleotide.

15. The method of claim 1, wherein the amplification reaction mixture of step b) is exposed to thermal cycling conditions limited to fewer than 20 thermal cycles.

16. The method of claim 15, wherein the hairpin oligonucleotide comprises a fluorophore moiety.

17. The method of claim 1, wherein the plurality of different target regions comprises a reference target region.

18. The method of claim 17, wherein said reference target region comprises β-actin or ZDHHC1.

19. The method of claim 1, wherein the sample comprises a DNA process control.

20. The method of claim 19, wherein the DNA process control comprises a zebrafish RASSF1 sequence.

* * * * *